US007521230B2

(12) United States Patent
Ikezu

(10) Patent No.: US 7,521,230 B2
(45) Date of Patent: Apr. 21, 2009

(54) NUCLEIC ACID ENCODING A BRAIN DERIVED TAU KINASE POLYPEPTIDE AND METHODS OF USE THEREOF

(75) Inventor: Tsuneya Ikezu, Omaha, NE (US)

(73) Assignee: Board of Regents of the University of Nebraska, Omaha, NE (US)

( * ) Notice: Subject to any disclaimer, the term of this patent is extended or adjusted under 35 U.S.C. 154(b) by 111 days.

(21) Appl. No.: 10/271,507

(22) Filed: Oct. 16, 2002

(65) Prior Publication Data

US 2004/0076958 A1 Apr. 22, 2004

(51) Int. Cl.

| | |
|---|---|
| ***C12N 5/00*** | (2006.01) |
| ***C12N 1/20*** | (2006.01) |
| ***C12N 1/00*** | (2006.01) |
| ***C12N 15/00*** | (2006.01) |
| ***C07H 21/02*** | (2006.01) |
| ***C07H 21/04*** | (2006.01) |
| *C12N 9/12* | (2006.01) |

(52) U.S. Cl. ............... 435/325; 435/252.3; 435/254.11; 435/320.1; 435/194; 536/23.1; 536/23.2; 536/23.5; 536/24.31

(58) Field of Classification Search ................ 536/23.1, 536/23.2, 23.5, 24.3, 24.31, 24.33; 435/320.1, 435/194, 419, 325, 252.3, 254.11

See application file for complete search history.

(56) References Cited

U.S. PATENT DOCUMENTS 5,583,034 A * 12/1996 Green et al. .................. 435/6

FOREIGN PATENT DOCUMENTS

WO WO 03/023034 A2 * 3/2003

OTHER PUBLICATIONS

Branden et al. "Introduction to Protein Structure", Garland Publishing Inc., New York, 1991, p. 247.*
Witkowski et al. (1999) Biochemistry 38:11643-11650.*
Nagase et al. GenBank Accession No. AB058758, Jun. 2001.*
Dictionary definition of "codon" at www.encarta.msn.com, last viewed on Jul. 20, 2007.*
Sato et al., "Tau-tubulin kinase 1 (TTBK1), a neuron-specific tau kinase candidate, is involved in tau phosphorylation and aggregation", J. Neurochem. 98:1573-1584, 2006.*
Manning et al., "The Protein Kinase Complement of the Human Genome", Science 298:1912-1916, 1933-1934, 2002.*
GenBank Accession No. AL133375, GI:13897009, Apr. 2001.*
GenBank Accession No. AL133375, GI:13897009, Jul. 2007.*
Crowther Ra et al. "Abnormal tau-containing filaments in neurodegenerative diseases". *Journal of Structural Biology* 2000:130:271-279.
Lau T et al. "Tau protein phosphorylation as a therapeutic target in alzheimer's disease", *Current Topis in Medicinal Chemistry* 2002:2:395-415.
Leevm et al. "Neurodegenerative tauopathiers". *Annu. Rev. Neurosci.* 2001:24:1121-1159.
Mandelkow E: "The tangled tale of tau", *Nature* 1999;402:588-589.
Takahashi, M., et al., "A novel tau-tublin kinase from bovine brain", FEBS Letters, 372: p. 59-64 (1995).

* cited by examiner

*Primary Examiner*—David J Steadman
(74) *Attorney, Agent, or Firm*—Dann, Dorfman, Herrell & Skillman; Robert C. Netter; Kathleen D. Rigaut

(57) ABSTRACT

The present invention provides materials and methods for treating Alzheimer's disease and other tau related neurodegenerative disorders. A tau kinase, Brain Derived Tau Kinase (BDTK) is provided. BDTK can cause hyperphosphorylation of tau protein, which leads to formation of neurofibrillary tangles, which are implicated in the degenerative symptoms of Alzheimer's and other neurodegenerative disorders. Methods of diagnosis and treatment based on the discovery of this novel tau kinase are also provided.

8 Claims, 15 Drawing Sheets

Figure 1A

AAACTGAAAGAGACAGGCGGCATGCAGAATGTGTTGTTCAAGGAATGTTGGAATGTTGAGTTGTTGAGTAA
CCCAACATGTCAGAAGGGGAGTAATGGCCTAATGGGTCCATGTTGGGAAGATGTTTTGATGTTACAGTAAA
GAGTGTCCATCTTATTTGGTAAGCAGTAAAAACCAATGGCAGAGTTTGTCCACAAATGAAAGAAAGGGCCA
AAGAAAGAGAGACACAGATTGAGCCAAAAGATAAAGCATATAGGTGGTGAGGTGAGAATTGCACATGACGG
GTGGTGGGTGCGAGTGTGGGATGGTCCCAGAAGTGGTGGGTGATGGGGACGTATGGGAGGATGGGTACAGG
AGAGGGGGATGAGTTGAGAGGAAGGCGATATAAACATGTAGAGGATGGAGTGGGGAATCAGGCGAGACTGA
TGGGTCAGATGAGGAATTTTAGACATGCTAGGAGTGGGGAAGATAAAGGGTGATGGAGACAGGTGAGTTTT
ATGGGAACAGGTAAGGAGTGATGGGGCTGTGCTGGGAGATGGAGTCAAGCGGGTGGCAGAGAGCTGTAAGG
AGAACCTGAGAGCTGGAGCGGGACAGCCAGAGAGTCCCAGGGCTGGAGGAGAGCGGAGCGGGGCCGTCGGA
ACGTGATGTCAGAGGAGGAGCCGTGATGTCAGAGCGGGCGGCGGGCGGTGATGTCAGGGCTGGTGCTGATG
CTGGCGGCGCGGTGCATTGTGGGCAGCTCCCCGCTCTGCCGCTGCCGCCGCCGTCGCCCAAGGAGGATCGG
GGCCGGGCCGGGCCGGGATGATCCGGGTCGGAAGGCCGCCGCCGCCGGAGGGAGCGGGTCACCCAACGCCG
CACTGAGCCGCCCCCGCCCCGCCCCGGCCCCGGGGGATGCGCCGCCCCGAGCTGCTGCCTCCGCCGCCGCC
GCAGCCGCAGCCGCAGCGGGCACAGAGCAGGTAGATGGCCCCCTCAGGGCAGGCCCGGCGGACACCCCTCC
CTCTGGCTGGCGGATGCAGTGCCTAGCGGCCGCCCTTAAGGACGAAACCAACATGAGTGGGGGAGGGGAGC
AGGCCGACATCCTGCCGGCCAACTACGTGGTCAAGGATCGCTGGAAGGTGGTGAAAAAGATCGGGGGCGGG
GGCTTTGGTGAGATCTACGAGGCCATGGACCTGCTGACCAGGGAGAATGTGGCCCTCAAGGTGGAGTCAGC
CCAGCAGCCCAAGCAGGTCCTCAAGATGGAGGTGGCCGTGCTCAAGAAGTTGCAAGGGAAGGACCATGTGT
GCAGGTTCATTGGCTGTGGCAGGAACGAGAAGTTTAACTATGTAGTGATGCAGCTCCAGGGCCGGAACCTG
GCCGACCTGCGCCGTAGCCAGCCGCGAGGCACCTTCACGCTGAGCACCACATTGCGGCTGGGCAAGCAGAT
CTTGGAGTCCATCGAGGCCATCCACTCTGTGGGCTTCCTGCACCGTGACATCAAGCCTTCAAACTTTGCCA
TGGGCAGGCTGCCCTCCACCTACAGGAAGTGCTATATGCTGGACTTCGGGCTGGCCCGGCAGTACACCAAC
ACCACGGGGGATGTGCGGCCCCCTCGGAATGTGGCCGGGTTTCGAGGAACGGTTCGCTATGCCTCAGTCAA
TGCCCACAAGAACCGGGAGATGGGCCGCCACGACGACCTGTGGTCCCTCTTCTACATGCTGGTGGAGTTTG
CAGTGGGCCAGCTGCCCTGGAGGAAGATCAAGGACAAGGAACAGGTAGGGATGATCAAGGAGAAGTATGAG
CACCGGATGCTGCTGAAGCACATGCCGTCAGAGTTCCACCTCTTCCTGGACCACATTGCCAGCCTCGACTA
CTTCACCAAGCCCGACTACCAGTTGATCATGTCAGTGTTTGAGAACAGCATGAAGGAGAGGGGCATTGCCG
AGAATGAGGCCTTTGACTGGGAGAAGGCAGGCACCGATGCCCTCCTGTCCACGAGCACCTCTACCCCGCCC
CAGCAGAACACCCGGCAGACGGCAGCCATGTTTGGGGTGGTCAATGTGACGCCAGTGCCTGGGGACCTGCT
CCGGGAGAACACCGAGGATGTGCTACAGGGAGAGCACCTGAGTGACCAGGAGAATGCACCCCCAATTCTGC
CCGGGAGGCCCTCTGAGGGGCTGGGCCCCAGTCCCCACCTTGTCCCCCACCCCGGGGGTCCTGAGGCTGAA
GTCTGGGAGGAGACAGATGTCAACCGGAACAAACTCCGGATCAACATCGGCAAAAGCCCCTGTGTGGAGGA
GGAACAGAGCCGAGGCATGGGGGTCCCCAGCTCCCCAGTGCGTGCCCCCCCAGACTCCCCCACAACCCCAG
TCCGTTCTCTGCGCTACCGGAGGGTGAACAGCCCTGAGTCAGAAAGGCTGTCCACGGCGGACGGGCGAGTG
GAGCTACCTGAGAGGAGGTCACGGATGGATCTGCCTGGCTCGCCCTCGCGCCAGGCCTGCTCCTCTCAGCC
AGCCCAGATGCTGTCAGTGGACACAGGCCACGCTGACCGACAGGCCAGTGGCCGCATGGACGTGTCAGCCT
CTGTGGAGCAGGAGGCCCTGAGCAACGCCTTCCGCTCGGTGCCGCTGGCTGAGGAGGAGGATTTCGACAGC
AAAGAGTGGGTCATCATCGACAAGGAGACGGAGCTCAAGGACTTCCCTCCAGGGGCTGAGCCCAGCACATC
GGGCACCACGGATGAGGAGCCCGAGGAGCTGCGGCCACTGCCCGAGGAGGGCGAAGAGCGGCGGCGGCTGG
GGGCAGAGCCCACCGTCCGGCCCCGGGGACGCAGCATGCAGGCGCTGGCGGAGGAGGACCTGCAGCATTTG
CCGCCCCAGCCCCTGCCACCCCAGCTGAGCCAGGGCGATGGCCGTTCCGAGACGTCACAGCCCCCCACGCC
TGGCAGCCCTTCCCACTCACCCCTGCACTCGGACCCCGCCCTCGACGGAGAGAGTCGGACCCCACAGGCC
CACAGAGACAGGTGTTCTCCGTGGCGCCCCCATTTGAGGTGAATGGCCTCCCACGAGCTGTGCCTCTGAGT
CTGCCCTACCAGGACTTCAAAAGAGACCTCTCCGATTACCGAGAACGGGCGCGGTTGCTCAACAGGGTCCG
GAGGGTGGGCTTCTCGCACATGCTGCTCACCACCCCCCAGGTCCCACTGGCTCCTGTTCAGCCTCAGGCTA
ATGGGAAGGAGGAAGAGGAGGAGGAGGAAGATGAGGAAGAGGAAGAAGAGGATGAGGAAGAAGAAGAG
GAGGAAGAGGAAGAGGAGGAGGAAGAAGAGGAGGAGGAGGAAGAGGAGGAGGAGGCTGCAGCGGCAGTTGC
CTTGGGGGAGGTGCTGGGGCCTCGTAGTGGCTCCAGCAGTGAGGGGAGTGAGAGGAGCACTGACCGGAGCC
AGGAGGGTGCCCCGTCCACGCTGCTGGCAGACGATCAGAAGGAGTCCAGGGGCCGGGCCTCCATGGCCGAT
GGGGACCTGGAGCCTGAGGAGGGCTCCAAAACGCTGGTGCTTGTCTCTCCTGGCGACATGAAGAAGTCGCC
CGTCACTGCCGAACTGGCCCCCGACCCCGACCTGGGCACCCTGGCTGCCCTCACTCCTCAGCATGAGCGGC
CCCAGCCCACGGGCAGCCAGCTGGACGTATCTGAGCCAGGCACCCTGTCCTCTGTCCTCAAGTCTGAGCCC
AAGCCCCCGGGGCCTGGGGCAGGGCTGGGGGCCGGGACAGTGACCACAGGGGTCGGGGGCGTGGCAGTCAC

Figure 1B

CTCCTCACCCTTCACCAAAGTTGAGAGGACCTTTGTGCACATTGCGGAGAAAACCCACCTCAACGTCATGT
CTTCCGGTGGACAAGCCTTGCGGTCTGAGGAGTTCAGCGCTGGGGGCGAGCTGGGTCTGGAGCTGGCCTCT
GATGGGGGCGCTGTGGAGGAGGGGGCCCGAGCGCCCCTGGAGAACGGCCTCGCCCTGTCAGGGCTGAATGG
GGCTGAGATAGAGGGCTCTGCCCTGTCTGGGGCCCCCCGGGAAACCCCCTCAGAGATGGCCACAAACTCAC
TGCCCAATGGCCCGGCCCTTGCAGACGGGCCAGCCCCGGTGTCCCCGCTGGAGCCAAGCCCTGAGAAAGTG
GCCACCATCTCCCCCAGACGCCATGCTATGCCAGGCTCTCGCCCCAGGAGCCGTATCCCTGTCCTGCTCTC
TGAGGAGGACACGGGCTCGGAGCCCTCAGGCTCACTGTCGGCCAAAGAGCGGTGGAGCAAGCGGGCTCGGC
CGCAGCAGGACCTGGCGCGGCTGGTGATGGAGAAGAGGCAGGGCCGCCTGCTGTTGCGGCTGGCCTCAGGG
GCCTCGTCCTCCTCCAGTGAGGAGCAGCGCCGTGCCTCTGAGACCCTCTCAGGCACGGGCTCTGAGGAGGA
CACGCCCGCCTCTGAGCCGGCAGCGGCCTTGCCCAGGAAGAGCGGGAGGGCAGCCGCCACCAGGAGCCGGA
TTCCCCGCCCCATTGGCCTCCGCATGCCCATGCCTGTTGCAGCCCAGCAGCCCGCCAGCAGATCCCATGGC
GCGGCCCCAGCATTGGACACAGCCATCACCAGCAGGCTCCAGCTGCAGACGCCCCCAGGGTCGGCCACTGC
TGCTGACCTCCGCCCCAAACAACCTCCTGGCCGCGGCCTGGGCCCAGGGCGAGCCCAAGCCGGAGCCAGGC
CCCCAGCGCCGCGCAGCCCGCGCCTCCCCGCGTCCACATCCGCCGCGCGCAATGCCAGCGCGTCCCCCCGG
AGCCAGTCCCTGTCCCGCAGAGAGAGCCCCTCCCCCTCGCACCAGGCCCGGCCCGGGGTCCCCCCGCCCCG
GGGCGTCCCGCCGGCCCGGGCCCAGCCTGATGGCACCCCCTCCCCCGGGGGCTCCAAGAAAGGACCCAGAG
GGAAACTCCAGGCTCAGCGCGCAACAACCAAAGGCCGGGCAGGAGGCGCGGAGGGCCGGGCTGGGGCCAGA
TAATGACGCCCGCTGCTCTCCGCGGTCCCCCACCCTCACCCCGGCCCCCCACCCGCAGCCGGCCACACTGG
AGCAGCTCCCAGCACAGCCTTACGCGCCCGACGCGCGCCACCCGCGGCCCCAGCTTTCCGCCTGCACCCGC
GAGGACGCGCGCGAGCACACGCGGCGCCCCGCCAGGCCTTAGGGCCCGTGGGGACGCGGCCCCGCGCCGC
GGGGAGGGTCTGCCTCCCCTTCCTCGCCCTGTGTCCTCTCATCCTCCCGCCGCCCGTCAGGCCGGCCAGCC
TCACATCAGTCTCTCCGCCCCGGGGAAGGCTCAGCCACTTTTCATCGAGGACTCCACTTCTGGGGACGCCT
GGTTCGTTCGCCCACCAGGCCTAGGCTACGCTCCATGCTCCCCCAGCAATCTCTGCCTACACCTCCTGCGG
CGCCTTGCCCTCCTCCGACCCCTTTCCAGCCAAAGTCCCCCCACCCCTTCAGAGAAGCAGCCTCAAATTCC
AGAAGTGGAGGCTCCAGCCTCCCCGCGAGGGTCCAGCCCCACAGTCTTCTGGGAGCCATTGTGGCCAGGGA
CGGCCTCTGGACTGCCAGGCTGGGTTGGGGACCCAGGGAACATCGGTCTACTCAGGTGTGAGGGGGCAGGT
CTGACCTGCCCCAAAGTTGGCTCCATCCTGGACAACTCGGTGAGAGGCAGTGGGCAAGTGATCTTGGAGAT
GGGTGGGCAGGTGATTCTGTGGGCAGGGGATGTGCTCCCCTGCACCTCTGGGGTGCAGAAACCTCTTGCCT
CCAGATTTGGGTGGAGCCTCTGTGGGAACCATAGGAAGTGTGTGGGCTGCCTTCCTGGGCAAGTATTTCCC
AGTGGGAAGTTGGAGGGGGCTTTAACAAAGTTTTACTCCCTCCCCTGTTCCCCTGATCTAGTGCTCAGGAC
CCTTCACCATCAGGAATTCCTTCCTGTCATCTAACCTCAGTCCTGCCTACTGCAGTTCCAGCCAACCTGCT
CTTTCCTGAGTTCAAAGCAGGTGGAGACTGGCTGGTTACCATCTTTGCACTGGCCCTTCGGAGATTCGGGG
ACTCAGTTCTGGTGGGGTCACCCTCCCTGTCCTCCCGCCTGTGGAGGGAGGGAGGGCTGGCTCAGGCATC
GTCTCCCGCAATGGGCAGAGAGAGCAGAGACAGGTGGACCAACAGACAGCTGGCCCCTGGAGGCAGAAAGG
CCCTTCTAACTTCCAGATTGTATGCTTGAGTGATGGGTCCCCAGCCCAAGCCCACTCTTCCCTCAGCTCAC
CCTTCAGCCTGTTCCTTCTTGCCCTGACCCCAGCCCGTGCAGCTGCTCTACTCCAGGAATGGATGTGGGA
CTCTTCCTGGGTTCTGGCTCCTGCATAGCTCACCCCACCTCATCATGAGCCTCAACTGCCTACATCTGGGG
CAAGCAGCACACCGGCTGCAGATGGGACAGCCAGCCCTGCCTATCTGGACAGGCCCCTGCAGCCTCTGTCC
CCTGGCCTAGCCTCTCTGTCCTTCCCTGAGTCACAGAGAGCAAGCCAAGACATCCAGGGAAAGAGGAAGAA
AGGCCTTAGTGTGCCCCAGCAGTCTGGCTGCGTCCAGCCACCATCACCCGGAAGGATGCCCACAAGGCAGC
TGACCCTGAAAGCAGCCTCCCCCTCATGGAGAGTCAGCAGCTTGGGCAGCCACTTCCAGGCCAGGGTGGTG
GCTTCTCTGCAGACCAGCTGAGGGGAGGACTCCTGGGTGGACAGCCTTTGACGTCCACCCCACGCTGATGC
AGAAGCTCCCAGAACACTCAGGAAACTTCTCCGGACAGAGCCCTCCTTGTCAACTTGAGGCCCTCCCAAGG
CCCTCTACTGCCCTCTGGGTCCAGCAGAGGGAGTGGAGGAAGGGCCACTGCCTCCCACCTAGAGCTTCTCC
GAATGACAATCAGCTCGTGCCAGGTGGGGACCAGGATATGACTCCTGGTGCCCAGGCCCTGGGCCTGCTCC
TTGCCACCAACCGAACCGTGAATGTAGGGCCCCCAGCCTCACCTCTGCCCCAGGACCAACAACACCCTGGT
TTGGAGCTGGGAGGAAGAAGGGGGCCTGAGAGAGCCCCAGGTCCATTCTACCCCCAGCTTCACTCAGCACT
GGAGCTGGCAGAGACGCAAAACCCAGTCTGCCCTTGGGATTCCAAACCTCCCTAGGGCTCCCAACTGACCT
CAGGCCTCTGAGTCACTGAATGTCACCAGGAGAGGTGGGGGAGGGAAAGTGGCCAGTGGGGAGGGGGTCA
CCTAGGGGACTGCCTCTGTGCCTCTCCCCAGGAAGCATCCAGGGCAGAGGAAGCCACATCTCCCGGTGCCC
CCAACCCCAGCTGCAGCCTCCTCCCCCTGAGCATTCATTCTCTCCACCAGGCCTCCAGGTCCTGAGCCCTT
CCTCTGTAAAAGTGTCACACCACCTCCCTCAGCACTTCCCCATCACAACAACCTATGTCACTGACTCAGAT
GCAGGGTCTGCTCACCCCAACACATGCCTTCCCTCCCCAGCCACACCGTGCACGAAGGGGGCACAGGAGAG
GAGAGGGGCTGTGCCCCAGGCTCCCCATTTCCCAGCTCCTCACAGAGGCCTGGTTTGCTCAGTCTTCTGAA
CTCCAGGGACCAGCCCTGGTGGGCATGGGGTGGGGAGCAGGGAGTTGCCCTTCCCCTCCCTCGGGAAGCCA
CCTAAGAATGTTTACATGCCAAACAGAATGTAACACCCCTCCCCAAGCCCTTCCCAGTCACTGCATGGCCT

Figure 1C

CTGCCCATCCTGCACCTGTCCACCCCACCCCAACACCCTGGAAGCCACTGTCAATGATTAGATCG
GGTCTCGGAAGGGAAGTAGCCATCACACCATTAAAAAGCCTGTGGACCTTTT

Figure 2 – BDTK Polypeptide

MQCLAAALKDETNMSGGGEQADILPANYVVKDRWKVVKKIGGGGFGEIYEAMDLLTRENVALKVESAQQ
PKQVLKMEVAVLKKLQGKDHVCRFIGCGRNEKFNYVVMQLQGRNLADLRRSQPRGTFTLSTTLRLGKQI
LESIEAIHSVGFLHRDIKPSNFAMGRLPSTYRKCYMLDFGLARQYTNTTGDVRPPRNVAGFRGTVRYAS
VNAHKNREMGRHDDLWSLFYMLVEFAVGQLPWRKIKDKEQVGMIKEKYEHRMLLKHMPSEFHLFLDHIA
SLDYFTKPDYQLIMSVFENSMKERGIAENEAFDWEKAGTDALLSTSTSTPPQQNTRQTAAMFGVVNVTP
VPGDLLRENTEDVLQGEHLSDQENAPPILPGRPSEGLGPSPHLVPHPGGPEAEVWEETDVNRNKLRINI
GKSPCVEEEQSRGMGVPSSPVRAPPDSPTTPVRSLRYRRVNSPESERLSTADGRVELPERRSRMDLPGS
PSRQACSSQPAQMLSVDTGHADRQASGRMDVSASVEQEALSNAFRSVPLAEEEDFDSKEWVIIDKETEL
KDFPPGAEPSTSGTTDEEPEELRPLPEEGEERRRLGAEPTVRPRGRSMQALAEEDLQHLPPQPLPPQLS
QGDGRSETSQPPTPGSPSHSPLHSGPRPRRRESDPTGPQRQVFSVAPPFEVNGLPRAVPLSLPYQDFKR
DLSDYRERARLLNRVRRVGFSHMLLTTPQVPLAPVQPQANGKEEEEEEEDEEEEEEEDEEEEEEEEEEE
EEEEEEEEEEEEAAAAVALGEVLGPRSGSSSEGSERSTDRSQEGAPSTLLADDQKESRGRASMADGDLE
PEEGSKTLVLVSPGDMKKSPVTAELAPDPDLGTLAALTPQHERPQPTGSQLDVSEPGTLSSVLKSEPKP
PGPGAGLGAGTVTTGVGGVAVTSSPFTKVERTFVHIAEKTHLNVMSSGGQALRSEEFSAGGELGLELAS
DGGAVEEGARAPLENGLALSGLNGAEIEGSALSGAPRETPSEMATNSLPNGPALADGPAPVSPLEPSPE
KVATISPRRHAMPGSRPRSRIPVLLSEEDTGSEPSGSLSAKERWSKRARPQQDLARLVMEKRQGRLLLR
LASGASSSSSEEQRRASETLSGTGSEEDTPASEPAAALPRKSGRAAATRSRIPRPIGLRMPMPVAAQQP
ASRSHGAAPALDTAITSRLQLQTPPGSATAADLRPKQPPGRGLGPGRAQAGARPPAPRSPRLPASTSAA
RNASASPRSQSLSRRESPSPSHQARPGVPPPRGVPPARAQPDGTPSPGGSKKGPRGKLQAQRATTKGRA
GGAEGRAGAR

6B

Tau/BDTK Phosphorylation Assay 100 80 60 40 20 0

0 50 100 150 200

Time (min)

BDTK1
Tau2
BDTK2
Tau1

6A (No signal from autoradiography)

BDTK(52-319) derived from original KIAA1855 failed to phoshporylate Tau protein as well as kinase itself.

Figure 7

7A. NeuN

7B. BDTK Antisense

Figure 9
A
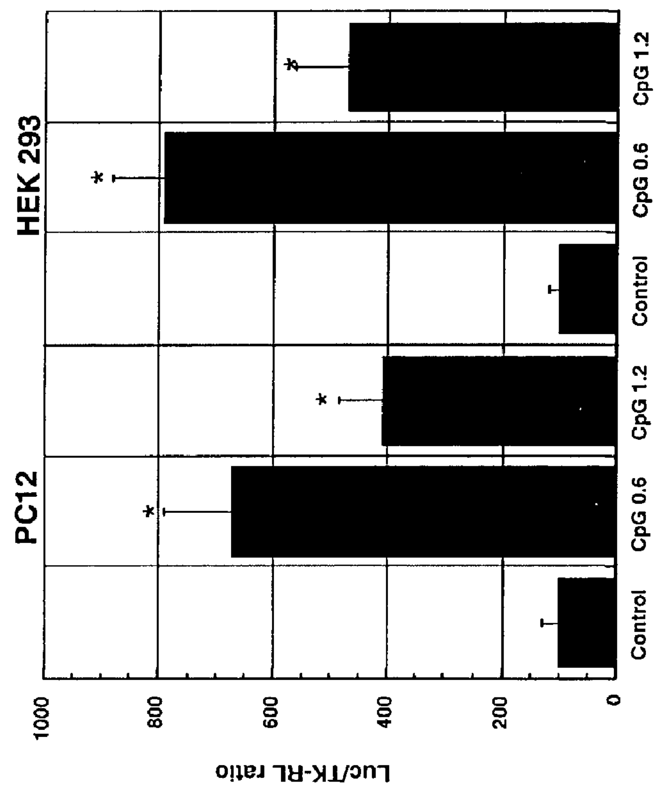
B
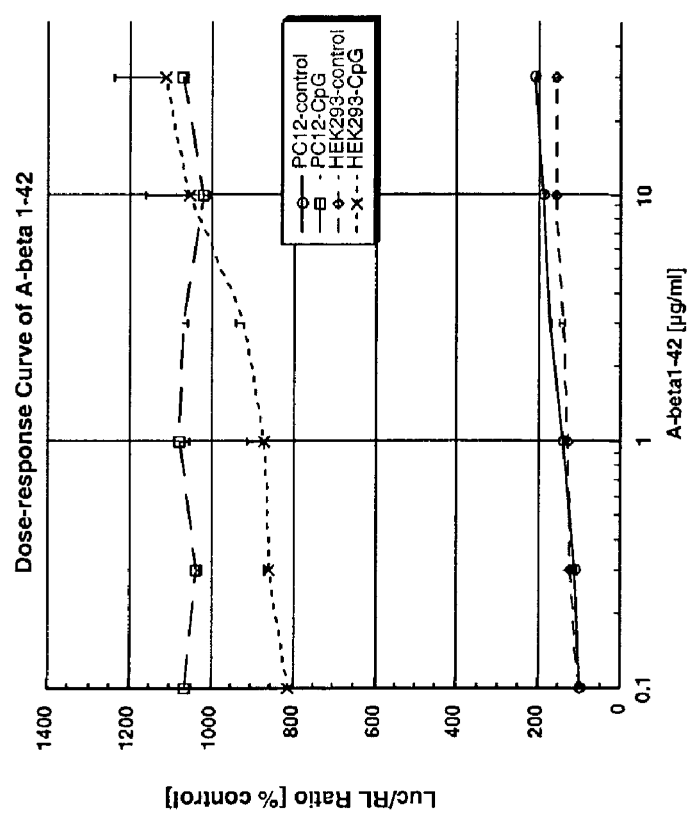

NUCLEIC ACID ENCODING A BRAIN DERIVED TAU KINASE POLYPEPTIDE AND METHODS OF USE THEREOF

FIELD OF THE INVENTION

This invention relates to the field of molecular biology and neurodegeneration. More specifically, the present invention provides materials and methods for altering tau protein phosphorylation to treat Alzheimer's disease and other tau related neurodegenerative disorders.

BACKGROUND OF THE INVENTION

Several publications are referenced in this application by author name, year and journal of publication in parentheses in order to more fully describe the state of the art to which this invention pertains. Several patents are also referenced throughout the specification. The disclosure of each of these publications and patent documents is incorporated by reference herein.

Approximately 4 million Americans have Alzheimer's Disease, and almost 45,000 Americans per year die of the disease (Hoyert, et al., 2001, Final Data for 1999, National Vital Statistics Report, 49: 6). One in ten persons over the age of 65, and nearly half of those over 85 have Alzheimer's (Alzheimer's Association, 2002). Alzheimer's disease is the most common form of dementia in today's elderly population (Mandelkow, E., 1999, Nature, 402: 588-589). The symptoms of Alzheimer's generally begin with a subtle decline in memory, and progress to include changes in personality, impaired learning ability, a decline in language function, the deterioration of visuospatial skills, and motor dysfunction. Eventually, the disease may cause extrapyramidal side effects (EPS), myoclonus, psychosis, seizures, aphasia, and primitive reflexes. This progression of symptoms is a result of increasing brain damage (Lau et al., 2002).

Beta-amyloid deposition is an established diagnostic marker of Alzheimer's disease, and is believed to be the primary cause of the disease. Neurofibrillary tangles (NFTs), which are comprised primarily of hyperphosphorylated tau protein and ubiquinated proteins are correlated with Alzheimer's disease progression, symptoms, and disabilities. Thus hyperphosphorylated tau protein is a distinguishing feature in degenerative disease progression of Alzheimer's and other neurodegenerative disorders.

Tau proteins are microtubule associated proteins that are abundant in the central nervous system, and are predominantly expressed in axons. Human tau proteins are encoded by a single gene consisting of 16 exons on chromosome 17q21, and six central nervous system isoforms are generated by alterative mRNA splicing.

The primary function of tau is to bind to, and stabilize microtubules, thereby promoting microtubule polymerization. The microtubule binding domains of tau are localized to the c-terminal portions of tau. Tau also contains numerous phosphorylation domains, many of which flank the microtubule binding domains. Phosphorylation is believed to play a significant role in microtubule binding by tau (Lee, et al., 2001, Annual Review of Neuroscience, 201: 1121-1159).

Aberrant phosphorylation of tau is observed in many neurodegenerative disorders. In addition to Alzheimer's disease, tau-positive neurofibrillary pathology has been linked to Amyotrophic lateral sclerosis/parkinsonism-dementia complex, Argyrophilic grain dimentia, Corticobasal degeneration, Creutzfeldt-Jakob disease, Dementia pugilistic, Diffuse neurofibrillary tangles with calcification, Down's syndrome, Frontotemporal dementia with parkinsonism linked to chromosome 17a, Gerstmann-Straussler-Scheinker disease, Hallervorden-Spatz disease, Myotonic dystrophy, Niemann-Pick disease, Non-Guamanian motor neuron disease with nerofibrillary tangles, Pick's disease, Postencephilitic parkinsonism, Prion protein cerebral amyloid angiopathy, Progressive subcortical gliosis, Progressive supranuclear palsy, Subacute sclerosing panencephalitis, and tangle only dementia. Neurodegenerative disorders which are tau related are known in the art as "tauopathies." (Lee, et al., supra).

Hyperphosphorylation of tau causes tau to dissociate from microtubules, and form tau protein aggregates which are the primary component of NFTs. Thus, identifying those protein kinases and protein phosphatases which regulate tau phosphorylation holds major promise for finding new treatments and therapeutic targets for ameliorating the symptoms of Alzheimer's and other neurodegenerative disorders.

Protein kinases implicated in tau regulation include mitogen-activated protein kinase (MAPK), glycogen synthase kinase 3β (GSK-3β), cyclin-dependent kinase 2 (cdk2), cdk5, $Ca^{2+}$/calmodulin-dependent protein kinase II, and MT affinity regulating kinase (Lee et al., supra). A great deal of research has focused on GSK-3β and cdk5. GSK-3β is ubiquitously expressed, and is known to be involved in cytoskeletal protein phosphorylation, cell cycle regulation, and cell death. Cdk5 is composed of p35 and p25 heterodimer, and is also ubiquitously expressed. The p25 component of cdk5 is unregulated in the brains of Alzheimer's Disease patients. Both GSK-3β and cdk5 are known to phosphorylate tau in vitro, but the link between these kinases, the formation of NFTs, and the progression of Alzheimer's and other tau related neurodegenerative disorders is still unclear (Lau, et al., 2002, Current Topics in Medicinal Chemistry, 2: 395-415.)

As those skilled in the treatment of Alzheimer's disease and tauopathies appreciate, a need exists for improved therapeutic agents for the treatment of these disorders. Identification of a human brain specific kinase which has a clear link to Alzheimer's disease and other tauopathies, provides an ideal target for the development of diagnostics and therapeutics for these pathologies.

SUMMARY OF THE INVENTION

In accordance with the present invention, methods and compositions for treating treat Alzheimer's disease and other tau related neurodegenerative disorders are provided. Specifically, a human brain specific tau kinase, Brain Derived Tau Kinase (BDTK) is disclosed, as well as methods of diagnosing and treating Alzheimer's disease and other tau related neurodegenerative disorders using the BDTK gene and it's promoter.

One embodiment of the invention comprises an isolated, enriched, or purified nucleic acid molecule encoding a BDTK polypeptide. A nucleic acid molecule encoding a BDTK protein includes any nucleic acid molecule which encodes any protein which is a variant or derivative of BDTK and which retains BDTK function. Most preferably, a BDTK nucleic acid molecule is the polynucleotide of SEQ ID NO:1, or a polynucleotide which encodes SEQ ID NO:2.

Also provided in accordance with the invention is a polynucleotide which encodes an isolated kinase domain of BDTK which has tau kinase activity. Preferably, a polynucleotide encoding the isolated kinase domain encodes amino acids 34-290 (SEQ ID NO:3), or 38-319 (SEQ ID NO:4) of the BDTK polypeptide. Most preferably, the polynucleotide encodes the isolated kinase domain of BDTK set forth as SEQ ID NO:3 (34-290).

Also encompassed within the present invention are polynucleotides which encode BDTK binding fragments. BDTK binding fragments are fragments of BDTK which can bind tau or BDTK, but which do not have kinase activity. Preferably, a polynucleotide encoding a BDTK binding fragment encodes amino acids 52-319 (SEQ ID NO:5), or 52-501 (SEQ ID NO:6) of the BDTK polypeptide.

Also provided in accordance with the invention are oligonucleotides, including probes and primers, that specifically hybridize with the nucleic acid sequences set forth above.

In a further aspect of the invention, recombinant DNA molecules comprising the nucleic acid molecules set forth above, operably linked to a vector are provided. The invention also encompasses host cells comprising a vector encoding the BDTK polypeptide of the invention.

Also encompassed within the present invention are BDTK promoter elements which can modulate transcription of BDTK. Preferably these promoter elements facilitate transcription of BDTK. Most preferably, the BDTK promoter elements comprise SEQ ID NO:7 or SEQ ID NO:8.

In another embodiment of the invention, BDTK promoter constructs are provided in which the BDTK promoter is operably linked to a heterologous gene encoding a gene product, such as a reporter gene or a gene encoding a toxic protein, such that the BDTK promoter controls the expression of the heterologous gene product. Suitable reporter genes for this purpose include, without limitation, luciferase, β-galactosidase, chloramphenicol acetyltransferase and green fluorescent protein. Nucleic acids encoding suitable toxic proteins include without limitation ricin, pseudomonas exotoxin, and diphtheria toxin. In a preferred embodiment, the BDTK promoter element comprises SEQ ID NO:7 or SEQ ID NO:8.

In a further aspect of the invention, antisense molecules which modulate BDTK expression are provided. Preferably, these antisense molecules inhibit BDTK expression.

One embodiment of the invention comprises an isolated, enriched, or purified BDTK polypeptide. A BDTK polypeptide includes any polypeptide which is a variant or derivative of BDTK and which retains BDTK function. Most preferably, a BDTK polypeptide is the polypeptide encoded by SEQ ID NO:1, or is the polypeptide of SEQ ID NO:2.

Also provided in accordance with the invention is an isolated kinase domain of BDTK which has kinase activity. Preferably the BDTK kinase domain has tau kinase activity. Preferably, an isolated BDTK kinase domain comprises amino acids 34-290 (SEQ ID NO:3), or 38-319 (SEQ ID NO:4) of the BDTK polypeptide. Most preferably, the isolated kinase domain of BDTK is the sequence set forth as SEQ ID NO:3 (34-290).

In another aspect of the invention, an antibody immunologically specific for BDTK is provided. Such antibodies may be monoclonal or polyclonal, and include recombinant, chimerized, humanized, antigen binding fragments of such antibodies, and anti-idiotypic antibodies.

In another aspect of the invention, recombinant organisms, or transgenic organisms which have a new combination of genes or nucleic acid molecules are provided.

In another aspect of the invention, methods for detecting BDTK mRNA or protein expression in a biological sample are provided. Exemplary methods comprise mRNA analysis, for example by RT-PCR, and immunological methods, for example contacting a sample with a detectably labeled antibody immunologically specific for BDTK and determining the presence of BDTK expression as a function of the amount of detectably labeled antibody bound by the sample relative to control cells. In a preferred embodiment, these assays may be used in diagnostic tests for Alzheimer's disease or other tau related neurodegenerative disorders.

In another aspect of the invention, reporter assays for determining modulation of BDTK expression are provided. These assays utilize a BDTK promoter operably linked to a nucleic acid encoding a reporter molecule to determine BDTK gene expression modulated by this promoter.

In a further aspect of the invention, methods for rational drug design are provided. These include without limitation, screening for possible modulators of BDTK expression or function. In an exemplary screening method, a small molecule is administered, and the level BDTK expression or activity is measured to determine if the small molecule inhibits or enhances BDTK expression or activity. In one embodiment, the small molecule is an antisense molecule and BDTK expression or activity is inhibited.

In a further aspect of the invention methods for treating a tau related disorder, preferably Alzheimer's disease are provided. Exemplary methods comprise administration of a therapeutic amount of a BDTK modulator. Preferably, the therapeutic modulator is a small molecule. Small molecules can include antibodies, oligonucleotides, proteins, peptides, and/or antisense molecules, and combinations thereof. Most preferably, the small molecule is an antisense molecule.

In a further aspect of the invention, methods of combination therapy for Alzheimer's disease or other tau related disorders are disclosed. Methods of treating such disorders may include without limitation (1) administering two or more agents which target BDTK activity or expression, or (2) administering one or more therapeutic agents which target BDTK activity or expression, in combination with one or more distinct therapeutic agents which target a different tau kinase, or distinct Alzheimer or tau-related neurodegenerative disorder targets.

In a further aspect of the invention, kits for diagnosis or therapy are provided. An exemplary kit comprises a BDTK protein, polynucleotide, or antibody. The kits may also include a pharmaceutically acceptable carrier and/or excipient, a suitable container, and instructions for administration.

BRIEF DESCRIPTION OF THE DRAWINGS

FIGS. 1A-1C depict the full length polynucleotide (SEQ ID NO: 1) which encodes Brain Derived Tau Kinase (BDTK), including the upstream promoter region, which is underlined.

FIG. 2 depicts the full length amino acid sequence (SEQ ID NO: 2) of Brain Derived Tau Kinase (BDTK), which is 1321 amino acids in length. The BDTK kinase domain (amino acids 34-290) is underlined.

Figure 7:
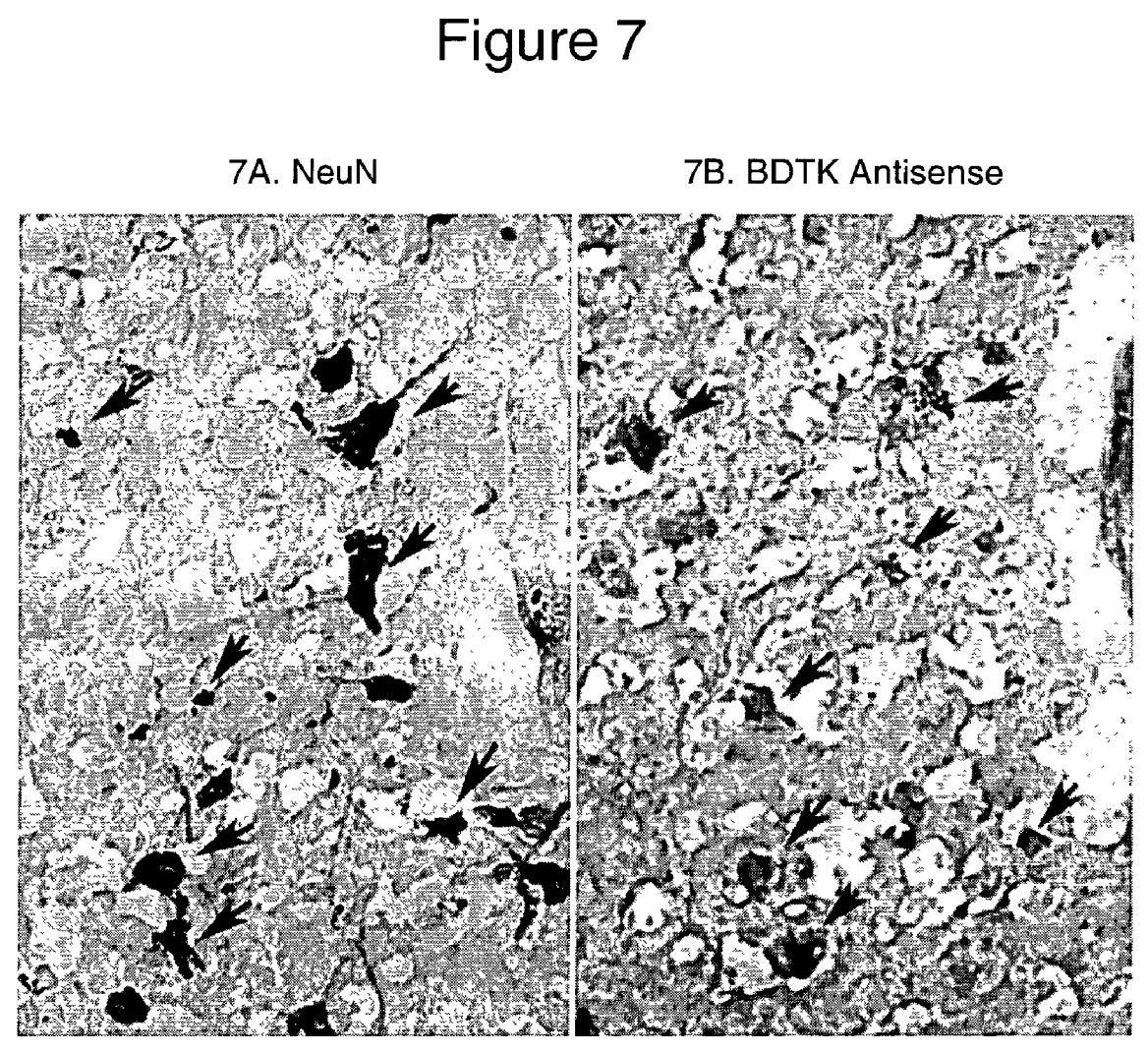

FIGS. 7A-7B are a pair of micrographs showing the results from situ hybridization experiments. Ten μm thickness brain slices were prepared from fresh frozen human brain cortex and were subjected to BDTK sense or antisense RNA probe hybridization. As shown in the right panel (7B), BDTK antisense probe specifically stains neuronal cell bodies, which are co-registered with neuronal cell body marker NeuN as shown in left panel(7A). Arrows indicate NeuN-positive neurons which express BDTK mRNA. The sense probe shows no specific staining in the adjacent section (data not shown). This data indicates that BDTK is mainly expressed in neurons.

FIGS. 9A-9B depict a luciferase assay used to determine promoter activity. To conduct this assay, 1.2 kb and 0.6 kb promoter sequence were inserted into pGL3-control vector (Promega, named as CpG1.2 and CpG0.6, respectively). The luciferase constructs were co-transfected with reference reporter gene (thymidine kinase promoter TK-RL plasmid, Promega) into PC12 and HEK293 cells using lipofection method (GenePorter, Gene Therapy Systems, Inc.). At 48 hours after DNA transfection, each luciferase activity was measured using Dua1-luciferase kit (Promega). (9A) Both 0.6 kb (CpG0.6) and 1.2 kb (CpG1.2) promoter has significantly higher promoter activity compared to control vector without DNA insert. BDTK promoter activity was observed in both cell lines. (9B) CpG1.2-luciferase vector was tested for its promoter activity by increasing dose of extracellular beta-amyloid peptide (A-beta) 1-42 (0-30 μg/ml) for 24 hours. CpG1.2 luciferase activities (PC12-CpG or HEK-CPG) are 8- to 10-fold higher than control activities (PC12-control or HEK293-control) without beta-amyloid stimulation. Beta-amyloid weakly stimulated CpG1.2-luciferase activity in HEK 293 cells but not in PC12 cells. This data demonstrates that the BDTK 5'-flanking region has promoter activity, in vitro.

DETAILED DESCRIPTION OF THE INVENTION

Figure 3:
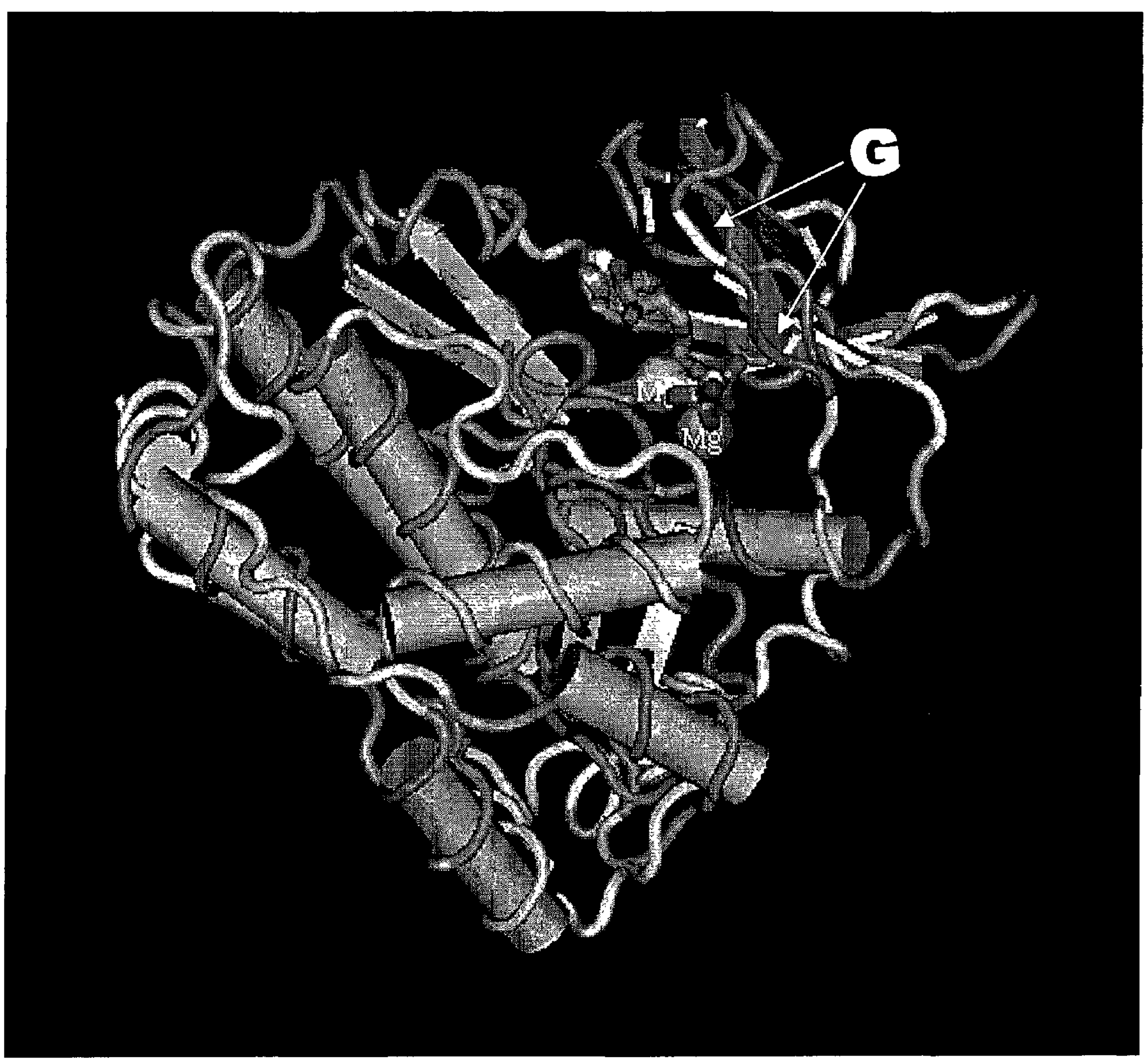
FIG. 3 is a three dimensional model of the BDTK protein, including the kinase domain. The two glycine residues in bold are important for their association with Mg2+ at the catalytic site.

The formation of Neurofibrillary tangles (NFTs) in the brains of patients with Alzheimer Disease and other neurodegernative disorders is correlated with disease symptoms and facilitates diagnosis of such disorders. Neurofibrillary tangles are primarily composed of phosphorylated tau protein. Accordingly, those molecules which play a role in tau phosphorylation provide therapeutic targets for the development of agents to treat such diseases.

In accordance with the present invention, a human brain specific tau kinase is provided. A commercial DNA bank was screened for a sequence which (1) is human specific, (2) is expressed in the brain, and (3) has a hypothetical protein kinase domain. The partial sequence identified did not encode a protein with kinase activity and was further evaluated for mRNA expression in the brains of Alzheimer's Disease and control patients. Cloning of the full length DNA sequence was subsequently performed using 5' rapid amplification of cDNA ends (RACE). Further homology and binding assays revealed that the previously unidentified N Terminal domain has kinase activity.

The Brain Derived Tau Kinase (BDTK) of the invention is a 1321 amino acid protein, responsible for the hyperphosphorylation of tau which leads to formation of neurofibrillary tangles. The kinase domain of BDTK spans amino acids 34-290, and possesses demonstrable phosphorylating activity. Two promoter regions of BDTK are also provided in accordance with the invention (see SEQ ID NO:7 and 8).

BDTK is specific to the human brain and is a tau kinase. Tau protein normally binds to microtubules, however upon hyperphosphorylation, tau dissociates from microtubules and forms Neurofibrillary tangles.

Accordingly, BDTK nucleic acids, proteins and antibodies thereto, according to this invention, may be used to identify compounds which modulate tau phosphorylation, and also to identify other proteins that are involved the control of tau phosphorylation and subsequent deleterious neurofibrillary tangle formation.

I. Definitions

The following definitions are provided to facilitate an understanding of the present invention:

"BDTK function" or "BDTK biological properties" include tau binding kinase activity, preferably tau phosphorylation activity. BDTK function can also mean immunological cross-reactivity with an antibody reactive with the polypeptide of SEQ I.D. No. 2, or sharing an epitope with the polypeptide of SEQ I.D. No. 2 (as determined for example by immunological cross-reactivity between the two polypeptides.) Preferably, BDTK activity is kinase activity. Most preferably BDTK activity is tau phosphorylation activity.

"BDTK essential function" is protein kinase activity, preferably tau phosphorylation activity.

"BDTK phosphorylation domain" refers to the kinase domain of a BDTK polypeptide. Preferably a BDTK phosphorylation domain is a protein sequence from the N-terminus of BDTK and has tau kinase activity. Preferably, an isolated BDTK phosphorylation domain comprises amino acids 34-290 (SEQ ID NO:3), or 38-319 (SEQ ID NO:4) of the BDTK polypeptide. Most preferably, the isolated phosphorylation domain of BDTK is the sequence set forth as SEQ ID NO:3 (34-290).

"Tauopathies" are generally known in the art, and refer to neurodegenerative disorders characterized by neurofibrillary tangles, which are primarily composed of hyperphosphorylated tau proteins.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the functional and novel characteristics of the sequence.

The term "nucleic acid molecule" describes a polymer of deoxyribonucleotides (DNA) or ribonucleotides (RNA). The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

The term "significant" here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes the sequence from naturally occurring enrichment events, such as viral infection, or tumor type growths, in which the level of one mRNA may be naturally increased relative to other species of mRNA.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated. The term is also chosen to distinguish clones already in existence which may encode BDTK but which have not been isolated from other clones in a library of clones. Thus, the term covers clones encoding BDTK which are isolated from other non-BDTK clones. Thus the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The terms "natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, or 80% or 85% or 90% or 95%, and often, more than 90%, or more than 95% of the nucleotides of the sequence match over the defined length of the nucleic acid sequence referred to using a specific SEQ ID NO. To the extent such allelic variations, analogues, fragments, derivatives, mutants, and modifications, including alternative nucleic acid processing forms and alternative post-translational modification forms result in derivatives of BDTK that retain any of the biological properties of BDTK, they are included within the scope of this invention.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989):

$$T_m=81.5°\text{ C.}+16.6\text{ Log }[\text{Na+}]+0.41(\%\ G+C)-0.63\ (\%\text{ formamide})-600/\#bp\text{ in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6× SSC, 5× Denhardt's solution, 0.5% SDS and 100 μg/ml denatured salmon sperm DNA at 42° C., and washed in 2× SSC and 0.5% SDS at 55° C. for 15 minutes. A high stringency hybridization is defined as hybridization in 6× SSC, 5× Denhardt's solution, 0.5% SDS and 100 μ/ml denatured salmon sperm DNA at 42° C., and washed in 1× SSC and 0.5% SDS at 65° C. for 15 minutes. A very high stringency hybridization is defined as hybridization in 6× SSC, 5× Denhardt's solution, 0.5% SDS and 100 μg/ml denatured salmon sperm DNA at 42° C., and washed in 0.1× SSC and 0.5% SDS at 65° C. for 15 minutes.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides, which include probes and/or primers are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the BDTK nucleic acid molecule such that the latter is transcribed into mRNA. Host cell machinery then translates mRNA into a polypeptide.

Those skilled in the art would recognize that a nucleic acid vector can contain many other nucleic acid elements besides the promoter element and the BDTK nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, periplasm or peroxisome localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism", or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, a recombinant organism can also be a recombinant cell, which may be a eukaryotic or a prokaryotic organism.

Amino acid residues described herein are preferred to be in the "L" isomeric form. However, residues in the "D" isomeric form may be substituted for any L-amino acid residue, provided the desired properties of the polypeptide are retained. All amino-acid residue sequences represented herein conform to the conventional left-to-right amino-terminus to carboxy-terminus orientation.

Amino acid residues are identified in the present application according to the three-letter or one-letter abbreviations in the following Table:

TABLE 1

| Amino Acid | 3-letter Abbreviation | 1-letter Abbreviation |
|---|---|---|
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| Glycine | Gly | G |
| L-Histidine | His | H |
| L-Isoleucine | Ile | I |
| L-Leucine | Leu | L |

TABLE 1-continued

| Amino Acid | 3-letter Abbreviation | 1-letter Abbreviation |
|---|---|---|
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |
| L-Lysine | Lys | K |

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

By the use of the term "enriched" in reference to a polypeptide it is meant that the specific amino acid sequence constitutes a significantly higher fraction (2-5 fold) of the total of amino acid sequences present in the cells or solution of interest than in normal or diseased cells or in the cells from which the sequence was taken. This could be caused by a person by preferential reduction in the amount of other amino acid sequences present, or by a preferential increase in the amount of the specific amino acid sequence of interest, or by a combination of the two. However, it should be noted that "enriched" does not imply that there are no other amino acid sequences present, just that the relative amount of the sequence of interest has been significantly increased.

The term "significant" here is used to indicate that the level of increase is useful to the person making such an increase, and generally means an increase relative to other amino acid sequences of about at least 2 fold, more preferably at least 5 to 10 fold or even more. The term also does not imply that there are no amino acid sequences from other sources. The other source amino acid may, for example, comprise amino acid sequences encoded by a yeast or bacterial genome, or a cloning vector such as pUC19. The term is meant to cover only those situations in which a person has intervened to elevate the proportion of the desired nucleic acid.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2-5 fold greater, e.g., in terms of mg/ml). Purification of at least one order of magnitude, preferably two or three orders, and more preferably four or five orders of magnitude is expressly contemplated. Thus the term "substantially pure" refers to a preparation comprising at least 50-60% by weight the compound of interest (e.g., polypeptide, protein, etc.). More preferably, the preparation comprises at least 75% by weight, and most preferably 90-99% by weight, the compound of interest. Purity is measured by methods appropriate for the compound of interest (e.g. chromatographic methods, agarose or polyacrylamide gel electrophoresis, HPLC analysis, mass spectrometry and the like).

"Natural allelic variants", "mutants" and "derivatives" of particular sequences of amino acids refer to amino acid sequences that are closely related to a particular sequence but which may possess, either naturally or by design, changes in sequence or structure. By closely related, it is meant that at least about 75%, or 80% or 85% or 90% or 95%, and often, more than 90%, or more than 95% of the amino acids of the sequence match over the defined length of the amino acid sequence referred to using a specific SEQ ID NO.

Different "variants" of BDTK exist in nature. These variants may be alleles characterized by differences in the nucleotide sequences of the gene coding for the protein, or may involve different RNA processing or post-translational modifications. The skilled person can produce variants having single or multiple amino acid substitutions, deletions, additions or replacements. These variants may include inter alia: (a) variants in which one or more amino acids residues are substituted with conservative or non-conservative amino acids, (b) variants in which one or more amino acids are added to the BDTK protein, (c) variants in which one or more amino acids include a substituent group, and (d) variants in which BDTK is fused with another peptide or polypeptide such as a fusion partner, a protein tag or other chemical moiety, that may confer useful properties to BDTK, such as, for example, an epitope for an antibody, a polyhistidine sequence, a biotin moiety and the like. Other BDTK proteins of the invention include variants in which amino acid residues from one species are substituted for the corresponding residue in another species, either at the conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to the person having ordinary skill in the art.

To the extent such allelic variations, analogues, fragments, derivatives, mutants, and modifications, including alternative nucleic acid processing forms and alternative post-translational modification forms result in derivatives of BDTK that retain any of the biological properties of BDTK, they are included within the scope of this invention.

"Mature protein" or "mature polypeptide" shall mean a polypeptide possessing the sequence of the polypeptide after any processing events that normally occur to the polypeptide during the course of its genesis, such as proteolytic processing from a polyprotein precursor. In designating the sequence or boundaries of a mature protein, the first amino acid of the mature protein sequence is designated as amino acid residue 1. As used herein, any amino acid residues associated with a mature protein not naturally found associated with that protein that precedes amino acid 1 are designated amino acid −1, −2, −3 and so on. For recombinant expression systems, a methionine initiator codon is often utilized for purposes of efficient translation. This methionine residue in the resulting polypeptide, as used herein, would be positioned at −1 relative to the mature BDTK protein sequence.

A low molecular weight "peptide analog" or "peptidomimetic" shall mean a natural or mutant (mutated) analog of a protein, comprising a linear or discontinuous series of fragments of that protein and which may have one or more amino acids replaced with other amino acids and which has altered, enhanced or diminished biological activity when compared with the parent or nonmutated protein.

The term "biological activity" is a function or set of functions performed by a molecule in a biological context (i.e., in an organism or an in vitro surrogate or facsimile model). The biological activity of BDTK is preferably kinase activity, and most preferably phosphorylation of the tau protein.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by the trained artisan, and are contemplated to be within the scope of this definition.

A "clone" or "clonal cell population" is a population of cells derived from a single cell or common ancestor by mitosis.

A "cell line" is a clone of a primary cell or cell population that is capable of stable growth in vitro for many generations.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')2 and F(v).

With respect to antibodies, the term "immunologically specific" refers to antibodies that bind to one or more epitopes of a protein or compound of interest, but which do not substantially recognize and bind other molecules in a sample containing a mixed population of antigenic biological molecules.

A "sample" or "patient sample" or "biological sample" generally refers to a sample which may be tested for a particular molecule, preferably BDTK polynucleotide, polypeptide, or antibody. Samples may include but are not limited to cells, including neural cells, tissue, including brain tissue, and body fluids, including cerebral-spinal fluid, blood, serum, plasma, urine, saliva, pleural fluid and the like.

As used herein, a "targeted gene" or "knock-out" is a DNA sequence introduced into the germline or a non-human animal by way of human intervention, including but not limited to, the methods described herein. The targeted genes of the invention include DNA sequences which are designed to specifically alter cognate endogenous alleles.

II. BDTK Nucleic Acid Molecules, Probes, and Primers and Methods of Preparing the Same Encompassed by the invention are nucleic acid molecules which encode an isolated, enriched, or purified BDTK polypeptide, including allelic variations, analogues, fragments, derivatives, mutants, and modifications of the same.

BDTK polynucleotides may include variants which are at least about 75%, or 80% or 85% or 90% or 95%, and often, more than 90%, or more than 95% homologous over the full length sequence. BDTK polynucleotides also may be 60% or 65% or 70% or 75% or 80% or 85% or 90% or 95% or 97% or 98% or 99% or greater than 99% homologous over the full length sequence. BDTK polynucleotides also include variants which (1) (a) must comprise at least 10 or 15 or 20 or 25 contiguous residues from the BDTK kinase domain, or (b) which are 60% or 65% or 70% or 75% or 80% or 85% or 90% or 95% or 97% or 98% or 99% homologous to the BDTK kinase domain, and (2) (a) which are at least about 75%, or 80% or 85% or 90% or 95%,or more than 90%, or more, than 95% homologous over the full length sequence, or (b) 60% or 65% or 70% or 75% or 80% or 85% or 90% or 95% or 97% or 98% or 99% homologous, over the full length sequence. All homology may be computed by algorithms known in the art, such as BLAST, described in Altschul et al. (1990), J. Mol. Biol. 215:403-10, or the Smith-Waterman homology search algorithm as implemented in MPSRCH program (Oxford Molecular). Someone of ordinary skill in the art would readily be able to determine the ideal gap open penalty and gap extension penalty for a particular nucleic acid sequence. Exemplary search parameters for use with the MPSRCH program in order to identify sequences of a desired sequence identity are as follows: gap open penalty: −16; and gap extension penalty: −4.

Degenerate variants are also encompassed by the instant invention. The degeneracy of the genetic code permits substitution of certain codons by other codons which specify the same amino acid and hence would give rise to the same protein. The nucleic acid sequence can vary substantially since, with the exception of methionine and tryptophan, the known amino acids can be coded for by more than one codon. Thus, portions or all of the BDTK gene could be synthesized to give a nucleic acid sequence significantly different from that shown in SEQ ID NO:1. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid formula shown in SEQ ID NO:1 or a derivative thereof. Any nucleotide or polynucleotide may be used in this regard, provided that its addition, deletion or substitution does not alter the amino acid sequence of SEQ ID NO:2 which is encoded by the nucleotide sequence. For example, the present invention is intended to include any nucleic acid sequence resulting from the addition of ATG as an initiation codon at the 5'-end of the BDTK nucleic acid sequence or its functional derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the BDTK genes and fragments thereof permitted by the genetic code are, therefore, included in this invention.

Nucleic acid sequences encoding BDTK may be isolated from appropriate biological sources using methods known in the art. In a preferred embodiment, a cDNA clone is isolated from a cDNA expression library of human origin. In an alternative embodiment, utilizing the sequence information provided by the cDNA sequence, genomic clones encoding BDTK may be isolated. Alternatively, cDNA or genomic clones having homology with BDTK may be isolated from other species, such as mouse, using oligonucleotide probes corresponding to predetermined sequences within the BDTK gene.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable *E. coli* host cell. Genomic clones of the invention encoding the human or mouse BDTK gene may be maintained in lambda phage FIX II (Stratagene).

Specific probes for identifying such sequences as the BDTK encoding sequence may be between 15 and 40 nucleotides in length. For probes longer than those described above, the additional contiguous nucleotides are provided within the sequences encoding BDTK.

In accordance with the present invention, nucleic acids having the appropriate level of sequence homology with the sequences encoding BDTK may be identified by using hybridization and washing conditions of appropriate stringency as previously set forth herein.

The nucleic acid molecules described herein include cDNA, genomic DNA, RNA, and fragments thereof which may be single- or double-stranded. Thus, oligonucleotides are provided having sequences capable of hybridizing with at least one sequence of a nucleic acid sequence, such as selected segments of the sequences encoding BDTK. Also contemplated in the scope of the present invention are methods of use for oligonucleotide probes which specifically hybridize with the DNA from the sequences encoding BDTK under high stringency conditions. Primers capable of specifically amplifying the sequences encoding BDTK are also provided. As mentioned previously, such oligonucleotides are useful for detecting, isolating and amplifying sequences encoding BDTK.

Nucleic acid molecules encoding the oligonucleotides of the invention may be prepared by two general methods: (1) synthesis from appropriate nucleotide triphosphates, or (2) isolation from biological sources. Both methods utilize protocols well known in the art. The availability of nucleotide sequence information, such as the DNA sequences encoding BDTK or SEQ ID NO:1, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be used directly or purified according to methods known in the art, such as high performance liquid chromatography (HPLC). Long, double-stranded polynucleotides must be synthesized in stages, due to the size limitations inherent in current oligonucleotide synthetic methods. Thus, for example, a 2.4 kb double-stranded molecule may be synthesized as several smaller segments of appropriate sequence. Complementary segments thus produced may be annealed such that each segment possesses appropriate cohesive termini for attachment of an adjacent segment. Adjacent segments may be ligated by annealing cohesive termini in the presence of DNA ligase to construct an entire 2.4 kb double-stranded molecule. A synthetic DNA molecule so constructed may then be cloned and amplified in an appropriate vector.

III. BDTK Proteins and Methods of Making the Same

Encompassed by the invention are isolated, purified, or enriched BDTK polypeptides, including allelic variations, analogues, fragments, derivatives, mutants, and modifications of the same which retain BDTK function. BDTK function is defined above, and includes kinase activity, preferably tau phosphorylation activity, or immunological cross-reactivity with an antibody reactive with the polypeptide of SEQ I.D. No. 2, or sharing an epitope with the polypeptide of SEQ I.D. No. 2 (as determined for example by immunological cross-reactivity between the two polypeptides.) Most preferably, BDTK activity is kinase activity, and most preferably tau phosphorylation activity.

BDTK polypeptides or proteins may include variants which are at least about 75%, or 80% or 85% or 90% or 95%, and often, more than 90%, or more than 95% homologous over the full length sequence. BDTK polypeptides also may be 60% or 65% or 70% or 75% or 80% or 85% or 90% or 95% or 97% or 98% or 99% or greater than 99% homologous over the full length sequence. BDTK polypeptides also include variants which (1) (a) must comprise at least 10 or 15 or 20 or 25 contiguous residues from the BDTK kinase domain, or (b) which are 60% or 65% or 70% or 75% or 80% or 85% or 90% or 95% or 97% or 98% or 99% homologous to the BDTK kinase domain, and (2) (a) which are at least about 75%, or 80% or 85% or 90% or 95%,or more than 90%, or more than 95% homologous over the full length sequence, or (b) 60% or 65% or 70% or 75% or 80% or 85% or 90% or 95% or 97% or 98% or 99% homologous over the full length sequence. All homology may be computed by algorithms known in the art, such as BLAST, described in Altschul et al. (1990), J. Mol. Biol. 215:403-10, or the Smith-Waterman homology search algorithm as implemented in MPSRCH program (Oxford Molecular). Someone of ordinary skill in the art would readily be able to determine the ideal gap open penalty and gap extension penalty for a particular protein sequence. Exemplary search parameters for use with the MPSRCH program in order to identify sequences of a desired sequence identity are as follows: gap open penalty: −12; and gap extension penalty: −2.

A full-length or truncated BDTK protein of the present invention may be prepared in a variety of ways, according to known methods. The protein may be purified from appropriate sources, e.g., transformed bacterial or animal cultured cells or tissues, by immunoaffinity purification. Additionally, the availability of nucleic acid molecules encoding BDTK enables production of the protein using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of full length or truncated BDTK may be produced by expression in a suitable prokaryotic or eukaryotic system. For example, part or all of a DNA molecule, such as Sequence I.D. No. 1, may be inserted into a plasmid vector adapted for expression in a bacterial cell, such as *E. coli*. Such vectors comprise the regulatory elements necessary for expression of the DNA in the host cell (e.g. *E. coli*) positioned in such a manner as to permit expression of the DNA in the host cell. Such regulatory elements required for expression include promoter sequences, transcription initiation sequences and, optionally, enhancer sequences.

The BDTK produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

The BDTK proteins of the invention, prepared by the aforementioned methods, may be analyzed according to standard procedures. For example, such proteins may be subjected to amino acid sequence analysis, according to known methods.

IV. BDTK Peptide Analogs and Pentidomimetics, and Methods of Making the Same

A peptide analog of the present invention can be made by exclusively solid phase techniques, by partial solid-phase techniques, by fragment condensation, by classical solution coupling, or, as long as the analog consists of only amino acids among the twenty naturally occurring amino acids corresponding to codons of the genetic code, by employing recombinant DNA techniques. Suitable host organisms for this purpose include, without limitation, *E. coli, B. subtilis, S. cerevisiae, S. pombe* and *P. pastoris*. Alternatively, insect or mammalian cells may be utilized.

Methods of making a polypeptide of known sequence by recombinant DNA techniques are well-known in the art. See, e.g., U.S. Pat. No. 4,689,318, which is incorporated herein by reference.

Methods for chemical synthesis of polypeptides are also well-known in the art and, in this regard, reference is made, by way of illustration, to the following literature: Yamashino and Li, *J Am Chem Soc* 100:5174-5178, 1978; Stewart and Young, Solid Phase Peptide Synthesis (WH Freeman and Co. 1969); Brown et al., JCS Peritin I, 1983, 1161-1167; M. Bodanszky et al., *Bioorg Chem* 2:354-362, 1973; U.S. Pat. Nos. 4,689,318; 4,632,211; 4,237,046; 4,105,603; 3,842,067; and 3,862,925, all of which are incorporated herein by reference.

V. BDTK Antibodies and Methods of Making the Same

The present invention also provides methods of making and methods of using antibodies capable of immunospecifically binding to BDTK or fragments thereof. Polyclonal antibodies directed toward BDTK protein may be prepared according to standard methods. In a preferred embodiment, monoclonal antibodies are prepared, which react immunospecifically with the various epitopes of the BDTK protein. Preferably, antibodies which bind to an epitope in the BDTK kinase domain are provided. Monoclonal antibodies have been prepared according to general methods of Kohler and Milstein, following standard protocols.

Purified BDTK, or fragments thereof, may be used to produce polyclonal or monoclonal antibodies which also may serve as sensitive detection reagents for the presence and accumulation of BDTK (or complexes containing BDTK) in mammalian cells. Recombinant techniques enable expression of fusion proteins containing part or all of the BDTK protein. The full length protein or fragments of the protein may be used to advantage to generate an array of monoclonal antibodies specific for various epitopes of the protein, thereby providing even greater sensitivity for detection of the protein in cells.

Antibodies according to the present invention may be modified in a number of ways. Indeed the term "antibody" should be construed as covering any binding substance having a binding domain with the required specificity. Thus, the invention covers antibody fragments, derivatives, functional equivalents, and homologues of antibodies, including synthetic molecules and molecules whose shape mimics that of an antibody enabling it to bind an antigen or epitope.

Exemplary antibody fragments, capable of binding an antigen or other binding partner, are Fab fragment consisting of the VL, VH, C1 and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Humanized antibodies in which CDRs from a non-human source are grafted onto human framework regions, typically with alteration of some of the framework amino acid residues, to provide antibodies which are less immunogenic than the parent non-human antibodies, are also included within the present invention.

Polyclonal or monoclonal antibodies that immunospecifically interact with BDTK protein can be utilized for identifying and purifying BDTK. For example, antibodies may be utilized for affinity separation of proteins with which they immunospecifically interact. Antibodies may also be used to immunoprecipitate proteins from a sample containing a mixture of proteins and other biological molecules. Other uses of anti-BDTK antibodies are described below.

VI. Methods of Using BDTK Polynucleotides, Polyioetides, and Antibodies for Screening and Diagnostic Assays BDTK-encoding nucleic acids may be used for a variety of purposes in accordance with the present invention. BDTK-encoding DNA, RNA, or fragments thereof may be used as probes to detect the presence of and/or expression of genes encoding BDTK proteins. Methods in which BDTK-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The BDTK-encoding nucleic acids of the invention may also be utilized as probes to identify related genes from other animal species. As is well known in the art, hybridization stringencies may be adjusted to allow hybridization of nucleic acid probes with complementary sequences of varying degrees of homology. Thus, BDTK-encoding nucleic acids may be used to advantage to identify and characterize other genes of varying degrees of relation to BDTK, thereby enabling further characterization of the hyperphosphorylation of tau in neurodegenerative conditions. Additionally, they may be used to identify genes encoding proteins that interact with BDTK (e.g., by the "interaction trap" technique), which should further accelerate identification of the components involved in the hyperphosphorylation of tau during neurofibrillary tangle formation.

Polyclonal or monoclonal antibodies immunologically specific for BDTK may be used in a variety of assays designed to detect and quantitate the protein. Such assays include, but are not limited to: (1) flow cytometric analysis; (2) immunochemical localization of BDTK in neural cells; and (3) immunoblot analysis (e.g., dot blot, Western blot) of extracts from various cells. Additionally, as described above, anti-BDTK can be used for purification of BDTK (e.g., affinity column purification, immunoprecipitation).

From the foregoing discussion, it can be seen that BDTK-encoding nucleic acids, BDTK expressing vectors, BDTK proteins and anti-BDTK antibodies of the invention can be used to detect BDTK gene expression in neural cells and alter BDTK protein expression for purposes of assessing the genetic and protein interactions involved in neurodegenerative and tau regulated diseases.

Exemplary approaches for detecting BDTK nucleic acid or polypeptides/proteins include:

a) comparing the sequence of nucleic acid in the sample with the BDTK nucleic acid sequence to determine whether the sample from the patient contains mutations; or b) determining the presence, in a sample from a patient, of the polypeptide encoded by the BDTK gene and, if present, determining whether the polypeptide is full length, and/or is mutated, and/or is expressed at the normal level; or c) using DNA restriction mapping to compare the restriction pattern produced when a restriction enzyme cuts a sample of nucleic acid from the patient with the restriction pattern obtained from normal BDTK gene or from known mutations thereof; or, d) using a specific binding member capable of binding to a BDTK nucleic acid sequence (either normal sequence or known mutated sequence), the specific binding member comprising nucleic acid hybridizable with the BDTK sequence, or substances comprising an antibody domain with specificity for a native or mutated BDTK nucleic acid sequence or the polypeptide encoded by it, the specific binding member being labeled so that binding of the specific binding member to its binding partner is detectable; or, e) using PCR involving one or more primers based on normal or mutated BDTK gene sequence to screen for normal or mutant BDTK gene in a sample from a patient.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair are nucleic acid sequences, they will be of a length to hybridize to each other under conditions of the assay, preferably greater than 10 nucleotides long, more preferably greater than 15 or 20 nucleotides long.

In most embodiments for screening for BDTK expression associated with tau hyperphosphorylation and degenerative tau related disorders, the BDTK nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are becoming increasingly important in the art.

Thus any of the aforementioned techniques may be used as a diagnostic tool for detecting Alzheimer's disease or other tau related neurodegenerative disorders in a patient sample.

VII. Methods of Using BDTK Polynucleotides for Antisense and Gene Therapy

Nucleic acid molecules, or fragments thereof, encoding BDTK may also be utilized to control the production of BDTK, thereby regulating the amount of protein available to participate in tau phosphorylation. Alterations in the physiological amount of BDTK protein may dramatically affect the activity of other protein factors involved in tau hyperphosphorylation associated with neurodegenerative disorders.

Antisense nucleic acid molecules which may be targeted to translation initiation sites and/or splice sites to inhibit the expression of the BDTK genes or production of their encoded proteins are also provided. Antisense oligonucleotides may be designed to hybridize to the complementary sequence of nucleic acid, pre-mRNA or mature mRNA, interfering with the production of polypeptides encoded by a given DNA sequence (e.g. either native BDTK polypeptide or a mutant form thereof), so that its expression is reduced or prevented altogether. In addition to the BDTK coding sequence, antisense techniques can be used to target control sequences of the BDTK gene, e.g. in the 5' flanking sequence of the BDTK coding sequence, whereby the antisense oligonucleotides can interfere with BDTK control sequences. The construction of antisense sequences and their use is described in Peyman and Ulman, Chemical Reviews, 90:543-584, (1990), Crooke, Ann. Rev. Pharmacol. Toxical., 32:329-376, (1992), and Zamecnik and Stephenson, Proc. Natl. Acad. Sci., 75:280-284, (1974). Such antisense molecules are typically between 15 and 30 nucleotides in length and often span the translational start site of the BDTK mRNA molecules.

Alternatively, antisense constructs may be generated which contain the entire BDTK cDNA in reverse orientation.

Alternatively, vectors such as viral vectors, can be used to introduce BDTK encoding nucleic acid constructs into a wide variety of different target cells. Typically the vectors are exposed to the target cells so that transformation can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically. In an alternative embodiment, where it is desirable to eliminate BDTK expressing cells, vectors encoding a toxic protein operably linked to the BDTK promoter may be utilized. Expression of the toxic protein triggers cell death in the recipient cells.

A variety of vectors, both viral vectors and plasmid vectors are known in the art, see U.S. Pat. No. 5,252,479 and WO 93/07282. In particular, a number of viruses have been used as gene transfer vectors, including papovaviruses, such as SV40, vaccinia virus, herpes viruses including HSV and EBV, and retroviruses.

VIII. Transgenic Organisms

The availability of BDTK encoding nucleic acids enables the production of strains of laboratory mice carrying part or all of the BDTK gene or mutated sequences thereof. Such mice may provide an in vivo model for assessing the mechanisms of Alzheimer's disease and other tau related neurodegenerative disorders. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the transcription suppressor role of BDTK.

A transgenic mouse carrying the human BDTK gene is generated by genomic integration of exogenous genomic sequence encoding human BDTK. These transgenic animals are useful for drug screening studies as animal models for human diseases and for eventual treatment of disorders or diseases associated with biological activities modulated by BDTK.

The term "animal" is used in this context to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene.

The DNA used for altering a target gene may be obtained by a wide variety of techniques that include, but are not limited to, isolation from genomic sources, preparation of cDNAs from isolated mRNA templates, direct synthesis, or a combination thereof.

A type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated BDTK genes to selectively inactivate the wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its nonhomologous insertion with effective herpes drugs such as gancyclovir (GANC) or (1-(2-deoxy-2-fluoro-B-D arabinofluranosyl)-5-iodouracil, (FIAU). By this counter selection, the number of homologous recombinants in the surviving transformants can be increased.

Therapeutic agents for the treatment or prevention of Alzheimer's disease and other tau related neurodegenerative disorders may be screened in studies using BDTK transgenic mice.

IX. Methods of Using BDTK for Rational Drug Design

The identification of the BDTK gene and its association with neurodegenerative disorders paves the way for aspects of the present invention to provide the use of materials and methods, such as are disclosed and discussed above, for establishing the contribution of this protein to the hyperphosphorylation of tau which leads to neurofibrillary tangle formation and the degenerative symptoms of Alzheimer's and other tau related disorders.

Such knowledge should facilitate planning of appropriate therapeutic and/or prophylactic measures to treat to reduce the degenerative symptoms associated with Alzheimer's disease and other tau related neurodegenerative disorders.

According to another aspect of the invention, methods of screening agents to identify suitable drugs for inhibiting or augmenting BDTK function are provided.

The BDTK polypeptide or fragment employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between a BDTK polypeptide or fragment and the agent being tested, or examine the degree to which the formation of a complex between a BDTK polypeptide or fragment and a known ligand is interfered with by the agent being tested.

Another technique for drug screening provides high throughput screening for compounds having suitable binding affinity to the BDTK polypeptides and is described in detail in Geysen, PCT published application WO 84/03564, published on Sep. 13, 1984. Briefly stated, large numbers of different, small peptide test compounds are synthesized on a solid substrate, such as plastic pins or some other surface. The peptide test compounds are reacted with BDTK polypeptide and washed. Bound BDTK polypeptide is then detected by methods well known in the art.

Purified BDTK can be coated directly onto plates for use in the aforementioned drug screening techniques. However, non-neutralizing antibodies to the polypeptide can be used to capture antibodies to immobilize the BDTK polypeptide on the solid phase.

This invention also contemplates the use of competitive drug screening assays in which neutralizing antibodies capable of specifically binding the BDTK polypeptide compete with a test compound for binding to the BDTK polypeptide or fragments thereof. In this manner, the antibodies can be used to detect the presence of any peptide which shares one or more antigenic determinants of the BDTK polypeptide.

A further technique for drug screening involves the use of host eukaryotic cell lines or cells (such as described above) which have a nonfunctional BDTK gene. These host cell lines or cells are defective at the BDTK polypeptide level. The host cell lines or cells are grown in the presence of drug compound. The rate of growth of the host cells is measured to determine if the compound is capable of regulating the growth of BDTK defective cells.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, one first determines the three-dimensional structure of a protein of interest (e.g., BDTK polypeptide) or, for example, of the BDTK-tau complex, by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides (e.g., BDTK polypeptide) may be analyzed by an alanine scan (Wells, 1991) Meth. Enzymol. 202:390-411. In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved BDTK polypeptide activity or stability or which act as inhibitors, agonists, antagonists, etc. of BDTK polypeptide activity. By virtue of the availability of cloned BDTK sequences, sufficient amounts of the BDTK polypeptide may be made available to perform such analytical studies as x-ray crystallography. In addition, the knowledge of the BDTK protein sequence provided herein will guide those employing computer modeling techniques in place of, or in addition to x-ray crystallography.

X. Assays for Altered Gene Expression (Promoter/Reporter Constructs)

According to another aspect of the invention, methods of screening drugs for therapy, i.e., promoting or inhibiting BDTK expression are provided.

The BDTK sequence elements employed in drug screening assays may either be free in solution, affixed to a solid support or within a cell.

An exemplary two step method entails identifying agents which bind to the BDTK promoter elements of the invention followed by biological assays wherein binding agents so identified are used in reporter gene assays to assess whether they modulate the activity of the BDTK promoter as a function of reporter gene expression levels.

Reporter genes suitable for this purpose include, without limitation, β-galactosidase, luciferase, chloramphenicol acetyltransferase (CAT), and green fluorescent protein (GFP).

Methods for operably linking the coding regions for the reporter genes to the promoter sequence elements of the invention are well known to those of ordinary skill in the art.

Following introduction of such DNA constructs into recipient host cells, the cells may be contacted with agents suspected of affecting BDTK promoter activity. Agents capable of altering expression of the reporter gene may prove efficacious in regulating BDTK promoter activity, thereby having therapeutic advantage in the treatment of Alzheimer's disease and other tau related neurodegenerative disorders.

XI. BDTK Pharmaceuticals, including Polynucleotide and Peptide Therapies

The BDTK polypeptides/proteins, antibodies, peptides, BDTK antisense molecules and vector constructs of the invention can be formulated in pharmaceutical compositions. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Administration of the pharmaceutical preparation is preferably in a "prophylactically effective amount" or a "therapeutically effective amount" (as the case may be, although prophylaxis may be considered therapy), this being sufficient to show benefit to the individual. Specifically a therapeutic effect can be an effect which decreases the rate of progression of the heurodegenerative symptoms associated with Alzheimer's disease and other tau related neurological disorders. Preferably, a therapeutic effect stops the progression of the neurodegenerative symptoms associated with Alzheimer's disease and other tau related neurological disorders. Most preferably, a prophylactic effect prevents the onset of the neurodegenerative symptoms associated with Alzheimer's disease and other tau related neurological disorders.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

XII. Kits and Articles of Manufacture

Any of the aforementioned products are methods can be incorporated into a kit which may contain a polynucleotide, an oligonucleotide, a polypeptide, a peptide, an antibody, a label, marker, or reporter, a pharmaceutically acceptable carrier, a physiologically acceptable carrier, instructions for use, a contain, a vessel for administration, an assay substrate, or any combination thereof.

Sequences

The following sequences have been utilized in the present invention:

```
Full length BDTK polynucleotide
                                                         (SEQ ID NO:1)
aaactgaaag agacaggcgg catgcagaat gtgttgttca aggaatgttg gaatgttgag  60

ttgttgagta acccaacatg tcagaagggg agtaatggcc taatgggtcc atgttgggaa 120

gatgttttga tgttacagta aagagtgtcc atcttatttg gtaagcagta aaaaccaatg 180

gcagagtttg tccacaaatg aaagaaaggg ccaaagaaag agagacacag attgagccaa 240

aagataaagc atataggtgg tgaggtgaga attgcacatg acgggtggtg ggtgcgagtg 300

tgggatggtc ccagaagtgg tgggtgatgg ggacgtatgg gaggatgggt acaggagagg 360

gggatgagtt gagaggaagg cgatataaac atgtagagga tggagtgggg aatcaggcga 420

gactgatggg tcagatgagg aattttagac atgctaggag tggggaagat aaagggtgat 480

ggagacaggt gagttttatg ggaacaggta aggagtgatg gggctgtgct gggagatgga 540
```

-continued

```
gtcaagcggg tggcagagag ctgtaaggag aacctgagag ctggagcggg acagccagag 600
agtcccaggg ctggaggaga gcggagcggg gccgtcggaa cgtgatgtca gaggaggagc 660
cgtgatgtca gagcgggcgg cgggcggtga tgtcagggct ggtgctgatg ctggcggcgc 720
ggtgcattgt gggcagctcc ccgctctgcc gctgccgccg ccgtcgccca aggaggatcg 780
gggccgggcc gggccgggat gatccgggtc ggaaggccgc cgccgccgga gggagcgggt 840
cacccaacgc cgcactgagc cgccccccgcc ccgccccggc cccgggggat gcgccgcccc 900
gagctgctgc ctccgccgcc gccgcagccg cagccgcagc gggcacagag caggtagatg 960
gccccctcag ggcaggcccg gcggacaccc ctccctctgg ctggcggatg cagtgcctag 1020
cggccgccct taaggacgaa accaacatga gtgggggagg ggagcaggcc gacatcctgc 1080
cggccaacta cgtggtcaag gatcgctgga aggtggtgaa aaagatcggg ggcgggggct 1140
ttggtgagat ctacgaggcc atggacctgc tgaccaggga gaatgtggcc ctcaaggtgg 1200
agtcagccca gcagcccaag caggtcctca agatggaggt ggccgtgctc aagaagttgc 1260
aagggaagga ccatgtgtgc aggttcattg gctgtggcag gaacgagaag tttaactatg 1320
tagtgatgca gctccagggc cggaacctgg ccgacctgcg ccgtagccag ccgcgaggca 1380
ccttcacgct gagcaccaca ttgcggctgg gcaagcagat cttggagtcc atcgaggcca 1440
tccactctgt gggcttcctg caccgtgaca tcaagccttc aaactttgcc atgggcaggc 1500
tgccctccac ctacaggaag tgctatatgc tggacttcgg gctggcccgg cagtacacca 1560
acaccacggg ggatgtgcgg ccccctcgga atgtggccgg gtttcgagga acggttcgct 1620
atgcctcagt caatgcccac aagaaccggg agatgggccg ccacgacgac ctgtggtccc 1680
tcttctacat gctggtggag tttgcagtgg gccagctgcc ctggaggaag atcaaggaca 1740
aggaacaggt agggatgatc aaggagaagt atgagcaccg gatgctgctg aagcacatgc 1800
cgtcagagtt ccacctcttc ctggaccaca ttgccagcct cgactacttc accaagcccg 1860
actaccagtt gatcatgtca gtgtttgaga acagcatgaa ggagaggggc attgccgaga 1920
atgaggcctt tgactgggag aaggcaggca ccgatgccct cctgtccacg agcacctcta 1980
ccccgcccca gcagaacacc cggcagacgg cagccatgtt tggggtggtc aatgtgacgc 2040
cagtgcctgg ggacctgctc cgggagaaca ccgaggatgt gctacaggga gagcacctga 2100
gtgaccagga gaatgcaccc ccaattctgc ccgggaggcc ctctgagggg ctgggcccca 2160
gtccccacct tgtcccccac ccgggggtc ctgaggctga agtctgggag gagacagatg 2220
tcaaccggaa caaactccgg atcaacatcg gcaaaagccc ctgtgtggag gaggaacaga 2280
gccgaggcat gggggtcccc agctccccag tgcgtgcccc cccagactcc ccccacaaccc 2340
cagtccgttc tctgcgctac cggagggtga acagccctga gtcagaaagg ctgtccacgg 2400
cggacgggcg agtggagcta cctgagagga ggtcacggat ggatctgcct ggctcgccct 2460
cgcgccaggc ctgctcctct cagccagccc agatgctgtc agtggacaca ggccacgctg 2520
accgacaggc cagtggccgc atggacgtgt cagcctctgt ggagcaggag gccctgagca 2580
acgccttccg ctcggtgccg ctggctgagg aggaggattt cgacagcaaa gagtgggtca 2640
tcatcgacaa ggagacggag ctcaaggact tccctccagg ggctgagccc agcacatcgg 2700
gcaccacgga tgaggagccc gaggagctgc ggccactgcc cgaggagggc gaagagcggc 2760
ggcggctggg ggcagagccc accgtccgge cccggggacg cagcatgcag gcgctggcgg 2820
aggaggacct gcagcatttg ccgccccagc ccctgccacc ccagctgagc cagggcgatg 2880
gccgttccga gacgtcacag ccccccacgc ctggcagccc ttcccactca cccctgcact 2940
```

-continued

```
cgggaccccg ccctcgacgg agagagtcgg accccacagg cccacagaga caggtgttct  3000
ccgtggcgcc cccatttgag gtgaatggcc tcccacgagc tgtgcctctg agtctgccct  3060
accaggactt caaaagagac ctctccgatt accgagaacg ggcgcggttg ctcaacaggg  3120
tccggagggt gggcttctcg cacatgctgc tcaccacccc ccaggtccca ctggctcctg  3180
ttcagcctca ggctaatggg aaggaggaag aggaggagga ggaggaagat gaggaagagg  3240
aagaagagga tgaggaagaa gaagaggagg aagaggaaga ggaggaggaa gaagaggagg  3300
aggaggaaga ggaggaggag gctgcagcgg cagttgcctt gggggaggtg ctggggcctc  3360
gtagtggctc cagcagtgag gggagtgaga ggagcactga ccggagccag gagggtgccc  3420
cgtccacgct gctggcagac gatcagaagg agtccagggg ccgggcctcc atggccgatg  3480
gggacctgga gcctgaggag ggctccaaaa cgctggtgct tgtctctcct ggcgacatga  3540
agaagtcgcc cgtcactgcc gaactggccc ccgaccccga cctgggcacc ctggctgccc  3600
tcactcctca gcatgagcgg ccccagccca cgggcagcea gctggacgta tctgagccag  3660
gcaccctgtc ctctgtcctc aagtctgagc ccaagccccc ggggcctggg gcagggctgg  3720
gggccgggac agtgaccaca ggggtcgggg gcgtggcagt cacctcctca cccttcacca  3780
aagttgagag gacctttgtg cacattgcgg agaaaaccca cctcaacgtc atgtcttccg  3840
gtggacaagc cttgcggtct gaggagttca gcgctggggg cgagctgggt ctggagctgg  3900
cctctgatgg gggcgctgtg gaggaggggg cccgagcgcc cctggagaac ggcctcgccc  3960
tgtcagggct gaatggggct gagatagagg gctctgccct gtctggggcc ccccgggaaa  4020
ccccctcaga gatggccaca aactcactgc ccaatggccc ggcccttgca gacgggccag  4080
ccccggtgtc cccgctggag ccaagccctg agaaagtggc caccatctcc cccagacgcc  4140
atgctatgcc aggctctcgc cccaggagcc gtatccctgt cctgctctct gaggaggaca  4200
cgggctcgga gccctcaggc tcactgtcgg ccaaagagcg gtggagcaag cgggctcggc  4260
cgcagcagga cctggcgcgg ctggtgatgg agaagaggca gggccgcctg ctgttgcggc  4320
tggcctcagg ggcctcgtcc tcctccagtg aggagcagcg ccgtgcctct gagaccctct  4380
caggcacggg ctctgaggag gacacgcccg cctctgagcc ggcagcggcc ttgcccagga  4440
agagcgggag ggcagccgcc accaggagcc ggattccccg ccccattggc ctccgcatgc  4500
ccatgcctgt tgcagcccag cagcccgcca gcagatccca tggcgcggcc ccagcattgg  4560
acacagccat caccagcagg ctccagctgc agacgccccc agggtcggcc actgctgctg  4620
acctccgccc caaacaacct cctggccgcg gcctgggccc agggcgagcc caagccggag  4680
ccaggccccc agcgccgcge agcccgcgcc tccccgcgtc cacatccgcc gcgcgcaatg  4740
ccagcgcgtc cccccggagc cagtccctgt cccgcagaga gagcccctcc ccctcgcacc  4800
aggcccggcc cggggtcccc ccgccccggg gcgtcccgcc ggcccgggcc cagcctgatg  4860
gcacccccctc ccccgggggc tccaagaaag gacccagagg gaaactccag gctcagcgcg  4920
caacaaccaa aggccgggca ggaggcgcgg agggccgggc tggggccaga taatgacgcc  4980
cgctgctctc cgcggtcccc caccctcacc ccggcccccc acccgcagcc ggccacactg  5040
gagcagctcc cagcacagcc ttacgcgccc gacgcgcgcc acccgcggcc ccagctttcc  5100
gcctgcaccc gcgaggacgc gcgcgagcac acgcggcgcc ccgccaggcc ttagggcccg  5160
tgggggacgc ggccccgcgc cgcggggagg gtctgcctcc ccttcctcgc cctgtgtcct  5220
ctcatcctcc cgccgcccgt caggccggcc agcctcacat cagtctctcc gccccgggga  5280
aggctcagcc acttttcatc gaggactcca cttctgggga cgcctggttc gttcgcccac  5340
```

-continued

```
caggcctagg ctacgctcca tgctccccca gcaatctctg cctacacctc ctgcggcgcc 5400
ttgccctcct ccgacccctt tccagccaaa gtccccccac cccttcagag aagcagcctc 5460
aaattccaga agtggaggct ccagcctccc cgcgagggtc cagccccaca gtcttctggg 5520
agccattgtg gccagggacg gcctctggac tgccaggctg ggttggggac ccagggaaca 5580
tcggtctact caggtgtgag gggcaggtc tgacctgccc caaagttggc tccatcctgg 5640
acaactcggt gagaggcagt gggcaagtga tcttggagat gggtgggcag gtgattctgt 5700
gggcagggga tgtgctcccc tgcacctctg gggtgcagaa acctcttgcc tccagatttg 5760
ggtggagcct ctgtgggaac cataggaagt gtgtgggctg ccttcctggg caagtatttc 5820
ccagtgggaa gttggagggg gctttaacaa agttttactc cctcccctgt tcccctgatc 5880
tagtgctcag gacccttcac catcaggaat tccttcctgt catctaaect cagtcctgcc 5940
tactgcagtt ccagccaacc tgctctttcc tgagttcaaa gcaggtggag actggctggt 6000
taccatcttt gcactggccc ttcggagatt cggggactca gttctggtgg ggtcaccctc 6060
cctgtcctcc cgcctgtggg agggagggag ggctggctca ggcatcgtct cccgcaatgg 6120
gcagagagag cagagacagg tggaccaaca gacagctggc cctggaggc agaaaggccc 6180
ttctaacttc cagattgtat gcttgagtga tgggtcccca gcccaagccc actcttccct 6240
cagctcaccc ttcagcctgt tccttcttgc cctgacccca gcccgtgcag ctgctctact 6300
ccaggaatgg atgtggggac tcttcctggg ttctggctcc tgcatagctc accccacctc 6360
atcatgagcc tcaactgcct acatctgggg caagcagcac accggctgca gatgggacag 6420
ccagccctgc ctatctggac aggcccctgc agcctctgtc ccctggccta gcctctctgt 6480
ccttccctga gtcacagaga gcaagccaag acatccaggg aaagaggaag aaaggcctta 6540
gtgtgcccca gcagtctggc tgcgtccagc caccatcacc cggaaggatg cccacaaggc 6600
agctgaccct gaaagcagcc tccccctcat ggagagtcag cagcttgggc agccacttcc 6660
aggccagggt ggtggcttct ctgcagacca gctgagggga ggactcctgg gtggacagcc 6720
tttgacgtcc accccacgct gatgcagaag ctcccagaac actcaggaaa cttctccgga 6780
cagagccctc cttgtcaact tgaggccctc ccaaggccct ctactgccct ctgggtccag 6840
cagagggagt ggaggaaggg ccactgcctc ccacctagag cttctccgaa tgacaatcag 6900
ctcgtgccag gtggggacca ggatatgact cctggtgccc aggccctggg cctgctcctt 6960
gccaccaacc gaaccgtgaa tgtagggccc ccagcctcae ctctgcccca ggaccaacaa 7020
caccctggtt tggagctggg aggaagaagg gggcctgaga gagccccagg tccattctac 7080
ccccagcttc actcagcact ggagctggca gagacgcaaa acccagtctg cccttgggat 7140
tccaaacctc cctagggctc ccaactgacc tcaggcctct gagtcactga atgtcaccag 7200
gagaggtggg ggagggaaag tgggccagtg gggagggggt cacctagggg actgcctctg 7260
tgcctctccc caggaagcat ccagggcaga ggaagccaca tctcccggtg cccccaaccc 7320
cagctgcagc ctcctccccc tgagcattca ttctctccac caggcctcca ggtcctgagc 7380
ccttcctctg taaaagtgtc acaccacctc cctcagcact tccccatcac aacaacctat 7440
gtcactgact cagatgcagg gtctgctcac cccaacacat gccttccctc cccagccaca 7500
ccgtgcacga agggggcaca ggagaggaga ggggctgtgc cccaggctcc ccatttccca 7560
gctcctcaca gaggcctggt ttgctcagtc ttctgaactc cagggaccag ccctggtggg 7620
catggggtgg ggagcaggga gttgcccttc ccctccctcg ggaagccacc taagaatgtt 7680
tacatgccaa acagaatgta acacccctcc ccaagccctt cccagtcact gcatggcctc 7740
```

-continued

```
tgcccatcct gcacctgtcc accccacccc aacaccctgg aagccactgt caatgattaa  7800

atcgggtctc ggaagggaag tagccatcac accattaaaa agcctgtgga cctttt 7856

BDTK Amino Acid Seguence
                                                        (SEQ ID NO:2)
MQCLAAALKDETNMSGGGEQADILPANYVVKDRWKVVKKIGGGGFGEIYEAMDLLTRENVA

LKVESAQQPKQVLKMEVAVLKKLQGKDHVCRFIGCGRNEKFNYVVMQLQGRNLADLRRSQP

RGTFTLSTTLRLGKQILESIEAIHSVGFLHRDIKPSNFAMGRLPSTYRKCYMLDFGLARQY

TNTTGDVRPPRNVAGFRGTVRYASVNAHKNREMGRHDDLWSLFYMLVEFAVGQLPWRKIKD

KEQVGMIKEKYEHRMLLKHMPSEFHLFLDHIASLDYFTKPDYQLIMSVFENSMKERGTAEN

EAFDWEKAGTDALLSTSTSTPPQQNTRQTAAMFGVVNVTPVPGDLLRENTEDVLQGEHLSD

QENAPPILPGRPSEGLGPSPHLVPHPGGPEAEVWEETDVNRNKLRINTGKSPCVEEEQSRG

MGVPSSPVRAPPDSPTTPVRSLRYRRVNSPESERLSTADGRVELPERRSRMDLPGSPSRQA

CSSQPAQMLSVDTGHADRQASGRMDVSASVEQEALSNAFRSVPLAEEEDFDSKEWVIIDKE

TELKDFPPGAEPSTSGTTDEEPEELRPLPEEGEERRRLGAEPTVRPRGRSMQALAEEDLQH

LPPQPLPPQLSQGDGRSETSQPPTPGSPSHSPLHSGPRPRRRESDPTGPQRQVFSVAPPFE

VNGLPRAVPLSLPYQDFKRDLSDYRERARLLNRVRRVGFSHMLLTTPQVPLAPVQPQANGK

EEEEEEEEDEEEEEEDEEEEEEEEEEEEEEEEEEEEEEAAAAVALGEVLGPRSGSSSEGS

ERSTDRSQEGAPSTLLADDQKESRGRASMADGDLEPEEGSKTLVLVSPGDMKKSPVTAELA

PDPDLGTLAALTPQHERPQPTGSQLDVSEPGTLSSVLKSEPKPPGPGAGLGAGTVTTGVGG

VAVTSSPFTKVERTFVHIAEKTHLNVMSSGGQALRSEEFSAGGELGLELASDGGAVEEGAR

APLENGLALSGLNGAEIEGSALSGAPRETPSEMATNSLPNGPALADGPAPVSPLEPSPEKV

ATISPRRHANPGSRPRSRIPVLLSEEDTGSEPSGSLSAKERWSKRARPQQDLARLVMEKRQ

GRLLLRLASGASSSSSEEQRRASETLSGTGSEEDTPASEPAAALPRKSGRAAATRSRIPRP

IGLRMPMPVAAQQPASRSHGAAPALDTAITSRLQLQTPPGSATAADLRPKQPPGRGLGPGR

AQAGARPPAPRSPRLPASTSAARNASASPRSQSLSRRESPSPSHQARPGVPPPRGVPPARA

QPDGTPSPGGSKKGPRGKLQAQRATTKGRAGGAEGRAGAR
```

Materials and Methods

The following materials and methods are provided to facilitate the practice of the present invention.

5'-Rapid Amplification of cDNA Ends (5'-RACE)

Human brain total RNA was extracted by Trizol (Invitrogen) reagent according to the manufacturer's procedure. 5'-RACE was performed using GeneRacer kit (Invitrogen). Briefly, 2 μg of total RNA was dephosphorylated by calf intestinal alkaline phosphatase (CIP), followed by removal of mRNA cap structure by tobacco acid pyrophosphatase (TAP). The dephosphorylated and decapped RNA was ligated with RNA oligo (CGACUGGAGCACGAGGACACUGACAUGGACUGAAGGAGUAGAAA) (SEQ ID NO:9) by T4 RNA ligase. The ligated mRNA was reverse-transcribed by avian myeloblastosis virus reverse-transcriptase (AMV-RT) using GSβ-1 primer (TGGCCTCGATGGACTCCAAGATCTGCTT) (SEQ ID NO:10). Generated cDNA ends were amplified by proof-reading pfu DNA polymerase (Pfu Turbo, Stratagene) using 5' primer (CGACTGGAGCACGAGGACACTGA) (SEQ ID NO:11) and GSβ-1 primer. The PCR program was 94° C. for 2 min, followed by 5 cycles of (94° C. for 30 sec and 72° C. for 3 min), 5 cycles of (94° C. for 30 sec and 70° C. for 3 min), 25 cycles of (94° C. for 30 sec, 65° C. for 30 sec, and 72° C. for 3 min), and 72° C. for 15 min. The PCR product was further amplified by Pfu Turbo using 5' Nested primer (GGACACTGACATGGACTGAAGGAGTA) (SEQ ID NO:12) and GSP-1-Nest (CAAGATCTGCTTGCCCAGCCGCAA) (SEQ ID NO:13). The PCR program was 94° C. for 2 min, followed by 25 cycles of (94° C. for 30 sec, 65° C. for 30 sec, and 72° C. for 2 min), and 72° C. for 15 min. The nested PCR reaction yielded 300 and 550 bp products. Each PCR product was separately purified using low-melting gel electrophoresis and subcloned into pCR4-TOPO vector using the TOPO TA cloning kit and TOP10 *E. coli* (both from Invitrogen). The subcloned plasmids were sequenced and the 550 bp PCR product had the correct 5'-cDNA ends of BDTK. The full sequence was obtained by T3 and T7 primer sequencing. The isolated gene sequence was aligned with deposited human genome sequence at chromosome 6 (GENBANK accession AL133375) and the full sequence was deduced.

Generation of Recombinant BDTK-enhanced Green Fluorescent Protein (EGFP) Fusion Genes His-tagged BDTK(52-319) gene was generated by amplifying the KIAA1855 gene in pBluescript (pBS) by Pfu Turbo using the primers 23264:GGAATTCCATATGGACCTGCTGACCAGGGA (SEQ ID NO:14) and 23265: AAGGATCCCAG-GAGGGCATCGGTGCCT (SEQ ID NO:15). The PCR product was digested with Nde I and BamH I and subcloned into the pET-28a vector (Novagen) using the Nde I-BamH I sites. His-tagged BDTK(52-501) gene was generated by amplifying the KIAA1855 gene by Pfu Turbo using 23264 and 23266 (GAAGTCCTTGAGCTCCGTCTC)(SEQ ID NO:16). The PCR product was digested with Nde I and Sac I, and subcloned into pET-28a vector using the Nde I-Sac I sites. BDTK (38-319) was generated by hybridizing a set of oligos (23990:

TATTCTTAAGAA-GATCGGGGGCGGGGGCTTTGGTGAAATC-TACGAGGC (SEQ ID NO:17) and 23991:

TAGCCTCGTAGATTTCACCAAAGC-CCCCGCCCCCGATCTTCTTAAGAA)(SEQ ID NO:18). The hybridized oligos were phosphorylated by T4 polynucleotide kinase and subcloned into Nde I-digested and dephosphorylated pET-28a-BDTK(52-319) by T4 DNA ligase. The direction of the ligation was confirmed by PCR. BDTK(52-1216)-EGFP fusion gene was generated by digestion of KIAA1855 gene in pBS with Sal I and Sac II, which was subcloned into pEGFP-N2 vector (Clontech) at Sal I-Sac II sites.

Purification of Recombinant BDTK Mutants

His-tagged BDTK(38-319), BDTK(52-319), BDTK(52-501) proteins were induced by 0.5 mM IPTG in BL21(DE3) pLysS *E. coli*, which appeared as inclusion body. The *E. coli* pellet was solubilized in BugBuster reagent (1 ml/1 g pellet) containing 25 U/ml of Benzonase (all from Novagen) and 0.5 mM dithiothreitol (DTT) and incubated for 20 min at room temperature. The samples were centrifuged at 15,000 g for 30 min at 4° C. The supernatant was discarded and pellets were resuspended in BugBuster containing 200 μg/ml of lysozyme (Sigma) and incubated for 5 min at room temperature. The samples were centrifuged at 15,000 g for 30 min at 4° C. The pellets were solubilized in 8M urea containing 100 mM $NaHPO_4$ and 10 mM Tris-Cl (pH 8.0), and centrifuged. The supernatant was mixed with Ni-NTA His-bind resins (Novagen) and incubated for 15 min at room temperature. The resin was washed 3 times with 8M urea containing 100 mM $NaHPO_4$ and 10 mM Tris-Cl (pH 6.3) and the bound molecules were eluted with 8M urea containing 100 mM $NaHPO_4$, and 10 mM Tris-Cl (pH 4.5). The eluted samples were pooled and dialyzed against dialysis buffer (50% glycerol, 10 mM Tris-Cl, pH 7.5, 1 mM EDTA, 0.1% Triton-X 100, and 1 mM DTT). The dialyzed samples were centrifuged at 15,000 g for 30 min at 4° C. and the purified proteins in the supernatant were quantified by Coomassie brilliant blue staining. BDTK(38-1216)-EGFP gene and control EGFP gene were stably transfected in human embryonic kindney (HEK) 293 cells by lipofection and G418 selection (600 μ/ml). The cells were used for the following tau-binding assays.

Purification of Recombinant Tau Proteins

The tau mutant genes (human Tau 1-441, 1-244, and 245-441), which were a generous gift of Dr. Hemant Paudel were purified as described (Crowther R A, et al. FEBS lett 337:135, 1994). The tau polypeptide used is Genbank Accession NM_005910. Briefly, recombinant tau gene in pET-3a vector was transformed into BL21(DE3)pLysE *E. coli* and recombinant proteins induced by the addition of 0.5 mM IPTG. *E. coli* was pelleted by centrifugation and resuspended in extraction buffer (50 mM piperazine-N, N'-bis-2-ethanesulphonic acid, pH 6.9, 1 mM DTT, 0.1 mM EDTA, 0.1 mM phenylmethylsulphonyl fluoride (PMSF), 1 μM leupeptine, and 1 μM pepstatin). The samples were sonicated and centrifuged at 10,000 g for 15 min. The supernatant was brought to 0.5M NaCl and incubated in a boiling water bath for 10 min. The samples were centrifuged at 10,000 g for 15 min and the supernatant was dialyzed against dialysis buffer (20 mM Hepes, pH 6.9, 50 mM NaCl, 2 mM DTT, 1 mM EGTA, 1 mM MgSO4, and 0.1 mM PMSF. n-20, 0.3M sucrose, and 0.3% BSA) for 4 hr at 4° C. This procedure typically purified the tau proteins to 30-50% purity.

Binding Study

Freshly purified BDTK(39-319), BDTK(52-319), and BDTK(52-501) (2 μg each) were bound on Ni-NTA His-bind resins and incubated with 2 μg of purified tau mutants (1-441, 1-244, and 245-441) in binding buffer (50 mM Tris-Cl, pH 7.4, 50 mM NaCl, 0.05% Tween-20, 0.3M sucrose, and 0.3% BSA) for 4 hr at 4 C. The resin was washed three times with binding buffer and subjected to SDS-PAGE and immunoblotting. Anti-tau monoclonal antibodies (Tau-1 for N-terminal tau, Chemicon, and T46 for C-terminal tau, Zymed) and anti-His-tag monoclonal antibody (Santa Cruz Biotech) were used for the detection of tau mutants and BDTK mutants, respectively. BDTK(38-1216)-EGFP fusion protein and GFP were purified by immunoprecipitation using anti-GFP polyclonal (Novus) and protein G-sepharose fast flow (Amersham Pharmacia). The purified proteins were subjected to tau binding assays using anti-tau antibodies and anti-GFP monoclonal antibody (Clontech).

Kination Study

Purified recombinant human tau (Calbiochem) was phosphorylated by purified BDTK(38-319) and BDTK(52-319) in vitro. Briefly, 1 μg of tau protein and 1 μg of BDTK mutants were incubated in buffer A (50 mM Tris-Cl, pH 7.5, 5mM Mg acetate, 1 mM EDTA, 1 mM DTT, 0.1 mM ATP, 2 μCi [γ-$^{32}$P] ATP) or buffer B (100 mM Mes-Na, pH 6.5, 5 mM Mg acetate, 1 mM EGTA, 1 mM DTT, 0.2 mM ATP, and 2 μCi [γ-$^{32}$P]ATP). The reaction was stopped at 30, 60, 120, and 180 minutes by addition of Laemmli sampling buffer. Samples were then subjected to SDS-PAGE and autoradiography.

mRNA In Situ Hybridization

BDTK probe vector was generated by the digestion of KIAA1855 gene in PBS by Bsm I, followed by blunt-ending by Pfu Turbo, and self-ligation. Digoxigenin-conjugated sense (915 nt) and antisense (517 nt) RNA probes were generated using T7 and T3 RNA polymerase, respectively. After titration of the probe, equal amounts of sense and antisense BDTK probe were hybridized to fresh frozen human brain sections (10 μm thickness, frontal cortex). The hybridized RNA probes were detected by alkaline phosphatase conjugated anti-digoxigenin monoclonal antibody (Roche) and visualized by chemogenic changes of NBT/BCIP substrates. The serial section was also immunohistochemically stained for NeuN (Chemicon), which is a marker for neuronal cell bodies.

CpG Island Methylation Assays

The CpG island where BDTK gene transcription starts was tested for its methylation status using methylation-sensitive restriction digestion and PCR detection. Briefly, genomic DNA extracted from human cortex was methylated with CpG methylase (Sss I methylase) and S-adenosylmethionine (New England Biolabs) or left unmethylated, in vitro. After the reaction, samples were subjected to restriction digestion using Aci I, Nci I, and Ava I, which digest unmethylated but not methylated GC-rich sequences. The samples were also subjected to restriction digestion with Sma I and EcoR I which are methylation insensitive. After restriction digestion, DNA samples were precipitated and subjected to PCR using Herculase DNA polymerase (Stratagene), which is optimized for amplification of high GC-rich sequence in the presence of 6% DMSO. A set of primers (25020: TCAGAGGAGGAGCCGTGATG (SEQ ID NO:19) and 25021: AGTGGGGAGGAGCAAAGTG (SEQ ID NO:20)) was used for the following PCR program: 98° C. for 3 min, followed by 10 cycles of (98° C. for 40 sec, 60° C. for 30 sec, and 72° C. for 1 min), 25 cycles of (98° C. for 40 sec, 60° C. for 30 sec, and 72° C. for 1 min plus 10 sec per cycle), and 72° C. for 10 min. The PCR product (500 bp) was separated onto 1% agarose gel and the PCR bands were densitometrically quantified. CpG methylated genomic DNA protected from Aci I, Nci I, or Ava I digestion serves as a positive control for the PCR reaction.

Reporter Assays for BDTK Promoter Region

A luciferase assay was used to determine promoter activity. To conduct this assay, 1.2 kb and 0.6 kb promoter sequence were inserted into pGL3-control vector (Promega, named as CpG1.2 and CpG0.6, respectively). The luciferase constructs were co-transfected with reference reporter gene (thymidine kinase promoter TK-RL plasmid, Promega) into PC12 and HEK293 cells using lipofection method (GenePorter, Gene Therapy Systems, Inc.). At 48 hours after DNA transfection, each luciferase activity was measured using Dua1-luciferase kit (Promega). Both 0.6 kb (CpG0.6) and 1.2 kb (CpG1.2) promoter has significantly higher promoter activity compared to control vector without DNA insert. BDTK promoter activity was observed in both cell lines. CpG1.2-luciferase vector was tested for its promoter activity by increasing dose of extracellular beta-amyloid peptide (A-beta) 1-42 (0-30 μg/ml) for 24 hours. CpG1.2 luciferase activities (PC12-CpG or HEK-CpG) are 8- to 10-fold higher than control activities (PC12-control or HEK293-control) without beta-amyloid stimulation. Beta-amyloid weakly stimulated CpG1.2-luciferase activity in HEK 293 cells but not in PC12 cells.

```
1.2 kb Promoter Region:
                                                    (SEQ ID NO: 7):
aaactgaaag agacaggcgg catgcagaat gtgttgttca aggaatgttg gaatgttgag  60

ttgttgagta acccaacatg tcagaagggg agtaatggcc taatgggtcc atgttgggaa  120

gatgttttga tgttacagta aagagtgtcc atcttatttg gtaagcagta aaaaccaatg  180

gcagagtttg tccacaaatg aaagaaaggg ccaaagaaag agagacacag attgagccaa  240

aagataaagc atataggtgg tgaggtgaga attgcacatg acgggtggtg ggtgcgagtg  300

tgggatggtc ccagaagtgg tgggtgatgg ggacgtatgg gaggatgggt acaggagagg  360

gggatgagtt gagaggaagg cgatataaac atgtagagga tggagtgggg aatcaggcga  420

gactgatggg tcagatgagg aattttagac atgctaggag tggggaagat aaagggtgat  480

ggagacaggt gagttttatg ggaacaggta aggagtgatg gggctgtgct gggagatgga  540

gtcaagcggg tggcagagag ctgtaaggag aacctgagag ctggagcggg acagccagag  600

agtcccaggg ctggaggaga gcggagcggg gccgtcggaa cgtgatgtca gaggaggagc  660

cgtgatgtca gagcgggcgg cgggcggtga tgtcagggct ggtgctgatg ctggcggcgc  720

ggtgcattgt gggcagctcc ccgctctgcc gctgccgccg ccgtcgccca aggaggatcg  780

gggccgggcc gggccgggat gatccgggtc ggaaggccgc cgccgccgga gggagcgggt  840

cacccaacgc cgcactgagc cgccccccgcc ccgccccggc cccgggggat gcgccgcccc  900

gagctgctgc ctccgccgcc gccgcagccg cagccgcagc gggcacagag caggtgaggc  960

ggggcggggc gggccggggt cggggcgggg gctccttcgt gggctcaggg ggctccgcct  1020

ggctcgcctc ccagcgcagc cttcttgggc tcccctccgc gctgctgtcg ccgcccgctg  1080

ggctgggacg ctggcctaca ccgcctgggc cgcgccgagg cctggagccg ctccctgtcc  1140

cagcacacaa gacctccctc cccaacccgt cctccgggca ctttgctcct ccccactc    1198

0.6 kb Promoter region:
                                                 (SEQ ID NO: 8):
tcagaggagg agccgtgatg tcagagcggg cggcgggcgg tgatgtcagg gctggtgctg  60

atgctggcgg cgcggtgcat tgtgggcagc tccccgctct gccgctgccg ccgccgtcgc  120

ccaaggagga tcggggccgg gccgggccgg gatgatccgg gtcggaaggc cgccgccgcc  180

ggagggagcg ggtcacccaa cgccgcactg agccgccccc gccccgcccc ggccccgggg  240

gatgcgccgc cccgagctgc tgcctccgcc gccgccgcag ccgcagccgc agcgggcaca  300

gagcaggtga ggcggggcgg ggcgggccgg ggtcggggcg ggggctcctt cgtgggctca  360
```

-continued

```
gggggctccg cctggctcgc ctcccagcgc agccttcttg ggctcccctc cgcgctgctg 420

tcgccgcccg ctgggctggg acgctggcct acaccgcctg ggccgcgccg aggcctggag 480

ccgctccctg tccccagcac acagacctcc ctccccaacc cgtcctccgg gcactttgct 540

cctccccact c                                                      551
```

CpG Promoter Assay

A luciferase/CPG methylation assay was conducted to determine if the promoters are regulated by CPG methylation. 1.2 kb and 0.6 kb promoter sequence were inserted into pGL3-control vector (Promega, named as CpG1.2 and CpG0.6, respectively). The luciferase constructs were methylated by CpG methylase (New Englash Biolabs) or untreated, and co-transfected with reference reporter gene (thymidine kinase promoter TK-RL plasmid, Promega) into PC12 using lipofection method (GenePorter, Gene Therapy Systems, Inc.). At 48 hours after DNA transfection, each luciferase activity was measured using Dua1-luciferase kit (Promega). Both unmethylated 0.6 kb (CpG0.6) and 1.2 kb (CpG1.2) promoter has significantly higher promoter activity (3.56 and 12.6 fold increase, respectively) compared to control vector without DNA insert. However, both CpG methylated 0.6 and 1.2 kb promoter lose its transcriptional activity (99.88% and 99.95% inhibition compared to umethylated CpG promoter, respectively). This data demonstrated that the BDTK promoter activity is regulated by the methylation of its CpG island.

Assays for BDTK Peptide Inhibitors

Figure 10:
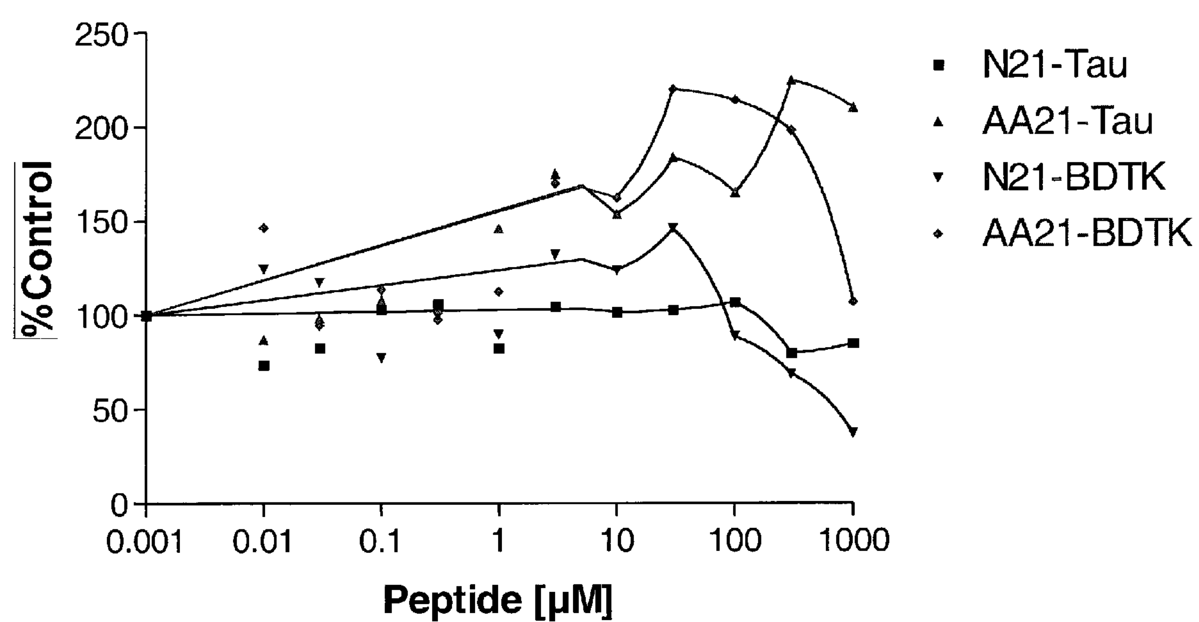
FIG. 10 depicts the effect of BDTK N-terminal peptide on its kinase activity. BDTK peptides may be used to inhibit BDTK activity. Two synthetic peptides (N21: KDRWKVVK-KIGGGGFGEIYEA (SEQ ID NO:21), and AA21: KDRWKVWKKIAGAGFGEIYEA (SEQ ID NO:22)) are synthesized to test if N21 and A21, wherein the conserved glycine residues are substituted with alanine, has inhibitory effect of BDTK kinase activity in vitro. Increasing amounts of peptides (0-1 mM) were tested for BDTK and tau phosphorylation, in vitro. N21 peptide showed inhibitory effect from 100 μM-1 mM up to 70% inhibition of BDTK phosphorylation (N21-BDTK). N21 peptide showed inhibitory effect from 100 μM-1 mM up to 70% inhibition of BDTK phosphorylation (N21-BDTK). N21 peptide also partially inhibited tau phosphorylation from 300 μM to 1 μM (N21-tau). In contrast, AA21 mutated peptide increased both BDTK (AA21-BDTK, from 30 to 300 μM) and tau phosphorylation (AA21-tau, from 30 μM to 1 μM) in dose response manner. These data suggest the potential use of N21 derivative as BDTK inhibitor, and the importance of the two glycine residues for the inhibitory effect.
Figure 11:
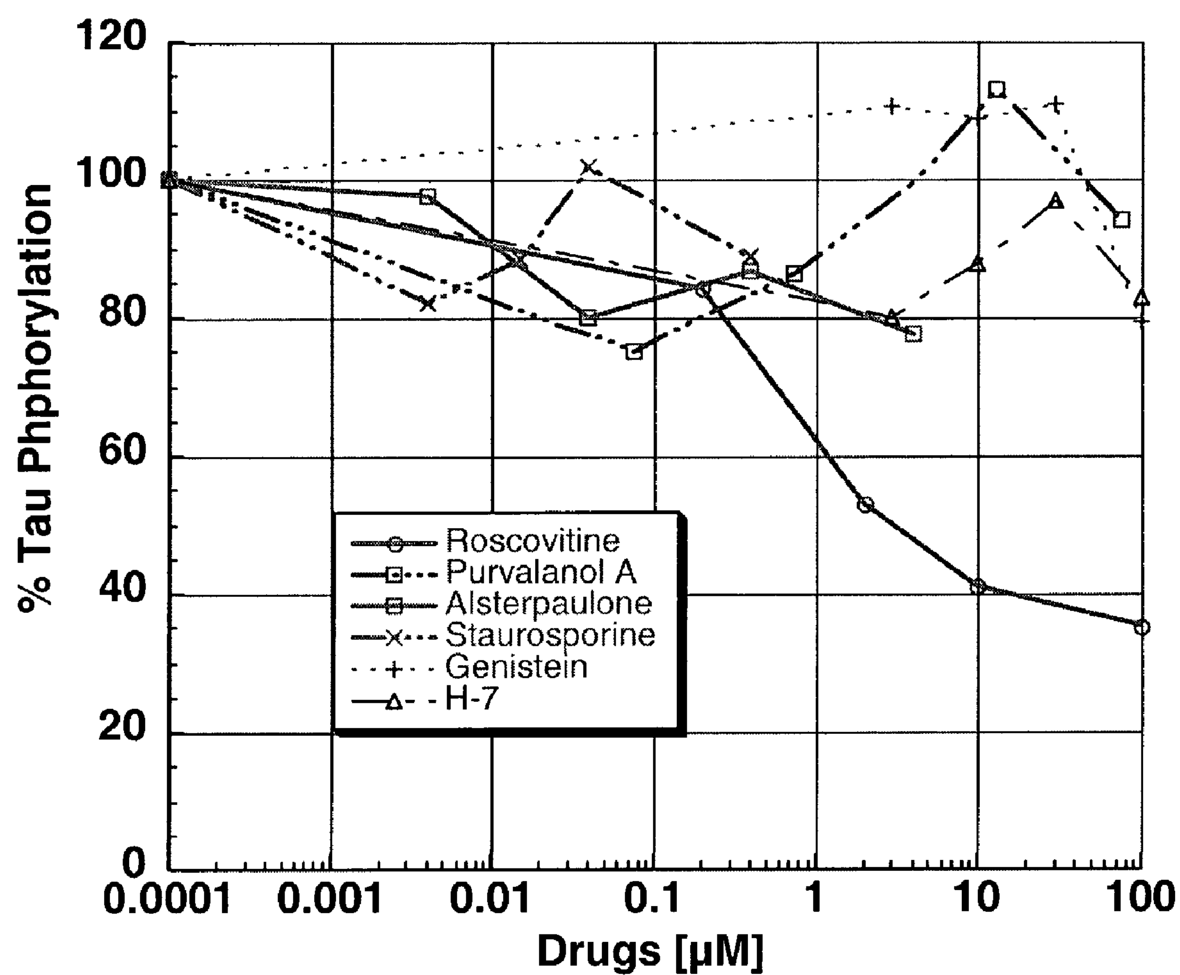
FIG. 11 depicts the effect of known protein kinase inhibitors on BDTK kinase activity. 0.2-100 μM of roscovitine (IC50: 130 μM for GSK-3beta and 160 nM for CDK-5), 75 nM-75 μM of puralanol A (IC50: 13 μM for GSK-3beta and 75 nM for CDK-5), 4 nM-4 μM of alterpaullone (IC50: 40 nM for GSK-3beta and 4 nM for CDK-5), 4 nM-400 μM of staurosporine (IC50: 15 nM for GSK-3beta and 4 nM for CDK-5), 3-100 )μM of genistein (control tyrosine kinase inhibitor), and 3-100 μM of H-7 (control protein kinase A inhibitor, all from Calbiochem) were tested for their effect on BDTK-mediated tau phosphorylation. Only rosovitine inhibited tau phosphorylation in dose-response manner (IC50 is about 3 μM), which is 43-fold lower than IC50 of GSK-3beta (130 μM) but 19-fold higher than that of CDK-5 (160 nM).
Figure 12:
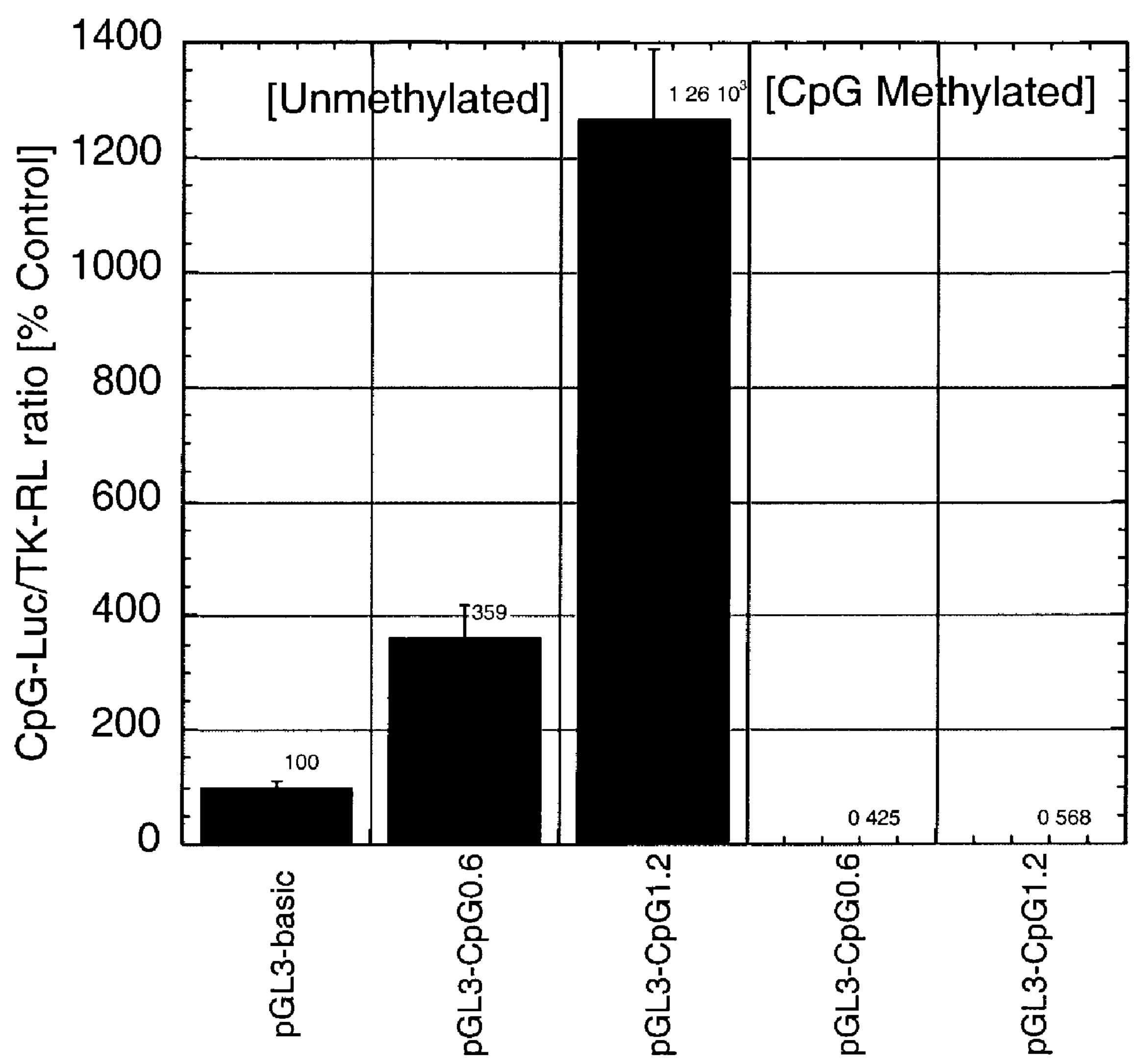
FIG. 12 depicts a luciferase reporter assay of BDTK promoter with or without CpG methylation. 1.2 kb and 0.6 kb promoter sequence were inserted into pGL3-control vector (Promega, named as CpG1.2 and CpG0.6, respectively). The luciferase constructs were methylated by CpG methylase (New Englash Biolabs) or untreated, and co-transfected with reference reporter gene (thymidine kinase promoter TK-RL plasmid, Promega) into PC12 using lipofection method (GenePorter, Gene Therapy Systems, Inc.). At 48 hours after DNA transfection, each luciferase activity was measured using Dua1-luciferase kit (Promega). Both unmethylated 0.6 kb (CpG0.6) and 1.2 kb (CpG1.2) promoter has significantly higher promoter activity (3.56 and 12.6 fold increase, respectively) compared to control vector without DNA insert. However, both CpG methylated 0.6 and 1.2 kb promoter lose its transcriptional activity (99.88% and 99.95% inhibition compared to umethylated CpG promoter, respectively). This data demonstrated that the BDTK promoter activity is regulated by the methylation of its CpG island.

An assay was conducted to identify promoters and inhibitors of BDTK activity. BDTK peptides may be used to inhibit BDTK activity. Two synthetic peptides (N21: KDRWKVWKKIGGGGFGEIYEA (SEQ ID NO:21) and AA21: KDRWKVWKKIAGAGFGEIYEA) (SEQ ID NO:22) are synthesized to test if N21 and A21, where conserved two glycine residues are substituted with alanine, has inhibitory effect of BDTK kinase activity in vitro. Increasing amounts of peptides (0-1 mM) were tested for BDTK and tau phosphorylation, in vitro. As shown in FIG. 10, N21 peptide showed inhibitory effect from 100 μM-1 mM up to 70% inhibition of BDTK phosphorylation (N21-BDTK). N21 peptide also partially inhibited tau phosphorylation from 300 μM to 1 μM (N21-tau). AA21 mutated peptide increased both BDTK (AA21-BDTK, from 30 to 300 μM) and tau phosphorylation (AA21-tau, from 30 μM to 1 μM) in dose response manner.

Assay for the Effect of Kinase Inhibitors on BDTK

An assay was conducted to measure the effect of kinase inhibitors on BDTK. 0.2-100 μM of roscovitine (IC50: 130 μM for GSK-3beta and 160 nM for CDK-5), 75 nM-75 μM of puralanol A (IC50: 13 μM for GSK-3beta and 75 nM for CDK-5), 4 nM-4 μM of alterpaullone (IC50: 40 nM for GSK-3beta and 4 nM for CDK-5), 4 nM-400 nM of staurosporine (IC50: 15 nM for GSK-3beta and 4 nM for CDK-5), 3-100 μM of genistein (control tyrosine kinase inhibitor), and 3-100 μM of H-7 (control protein kinase A inhibitor, all from Calbiochem) were tested for their effect on BDTK-mediated tau phosphorylation. As shown in FIG. 10, only rosovitine inhibited tau phosphorylation in dose-response manner (IC50 is about 3 μM), which is 43-fold lower than IC50 of GSK-3beta (130 μM) but 19-fold higher than that of CDK-5 (160 nM). Other inhibitors have no effect on tau phosphorylation by BDTK. (See Current Topics in Medical Chemistry 2:395-415 for IC50s-appendix)

EXAMPLES

The following examples are provided to illustrate certain embodiments of the invention. They are not intended to limit the invention in any way.

Example I

Isolation and Characterization of Human BDTK

The Kazusa DNA bank was screened to isolated a gene which was both human specific and brain specific. A sequence was obtained that fit these criteria. mRNA from the brains of Alzheimer's disease patients and control patients was isolated and evaluated. The full cDNA sequence of BDTK was cloned using 5' rapid amplification of cDNA ends (RACE). The BDTK protein was expressed, isolated, and purified as set forth above.

BDTK protein sequence has 88% similarity and 81% identity with mouse tau/tublin kinase (Ttbk, GenBank accession: AB046593) for the first 328 amino acid sequence. However, the rest of the amino acid sequence (329-1321) has no homologous sequence with other mammals but has weak similarity with *D. melanogster* (AE003843) and *C. elegans* (T24262 and T26716). The gene expression is exclusive to brains (both adult and fetal brains) and very low in the other tissues, including heart, lung, liver, skeletal muscle, kidney, pancreas, spleen, testis, ovary, and fetal liver. BDTK expression is high in certain brains regions, including amygdala, corpus callosum, cerebellum, and caudaute nucleus and relatively high in other regions, such as hippocampus, substantia nigra, subthalamic nucleus, thalamus, and spinal cord. ProfileScan revealed BDTK has putative protein kinase domain at the N-terminus (52-319), NULL domain (poly E domain) in the center of the molecule, and a proline-rich region at the C-terminal end.

TABLE II

| 5'-RACE SEQUENCE |
|---|
| (SEQ ID NO:23) |
| CAGCCGCAGC CGCAGCGGGC ACAGAGCAGG TAGATGGCCC |
| CCTCAGGGCA GGCCCGGCGG ACACCCCTCC CTCTGGCTGG |
| CGG**ATG**CAGT GCCTAGCGGC CGCCCTTAAG GACGAAACCA |
| ACATGAGTGG GGGAGGGGAG CAGGCCGACA TCCTGCCGGC |
| CAACTACGTG GTCAAGGATC GCTGGAAGGT GGTGAAAAAG |
| ATCGGGGGCG GGGGCTTTGG TGAGATCTAC GAGGC |

The new sequence identified from 5'-RACE is composed of 3 segments, and is located on chromosome 6 (GenBank accession AL133375). The first exon (underlined) is 27 bp (65967-65993), followed by a 165 bp second exon (68892-69056), and a 43 bp third exon (underlined) (75027-75069), which is followed by KIAA1855 sequence. The two introns between exon 1-2 and exon 2-3 are 2898 bp and 5970 bp, respectively. The open reading frame starts from the exon 2 (68948, bold). An additional 51 amino acid sequence was found on its N-terminus.

The new amino acid sequence (MQCLAAALKDET-NMSGGGEQADILPANYVVKDRWKVVK-KIGGGGFGEIYEA) (SEQ ID NO:24) provides the missing region of the sequence isolated from the Kazusa bank. This region is important for BDTK kinase activity.

The kinase domain of BDTK can be isolated and purified, both to analyze it's kinase activity in vitro, and to generate kinase domain specific antibodies. This may be accomplished by recombinant expression of the kinase domain, as described previously, or by producing a full length peptide (for example, SEQ ID NO:2), and cleaving it at the kinase domain (for example, SEQ ID NO:3 or 4). Antibodies may be generated by methods known in the art, to unphosphorylated or phosphorylated BDTK.

Example II

BDTK Binding and Kinase Activity

The full length BDTK polypeptide, and the isolated BDTK kinase domain were evaluated for their tau interaction and phosphorylation activity. Full length BDTK (SEQ ID NO:1), and isolated BDTK kinase domain (amino acids 38-319, SEQ ID NO:4) are able to phosphorylate tau, however amino acids 52-319 (SEQ ID NO:5) do not possess this activity. Full length BDTK binds tau with higher affinity than the isolated kinase domain.

Figure 4:
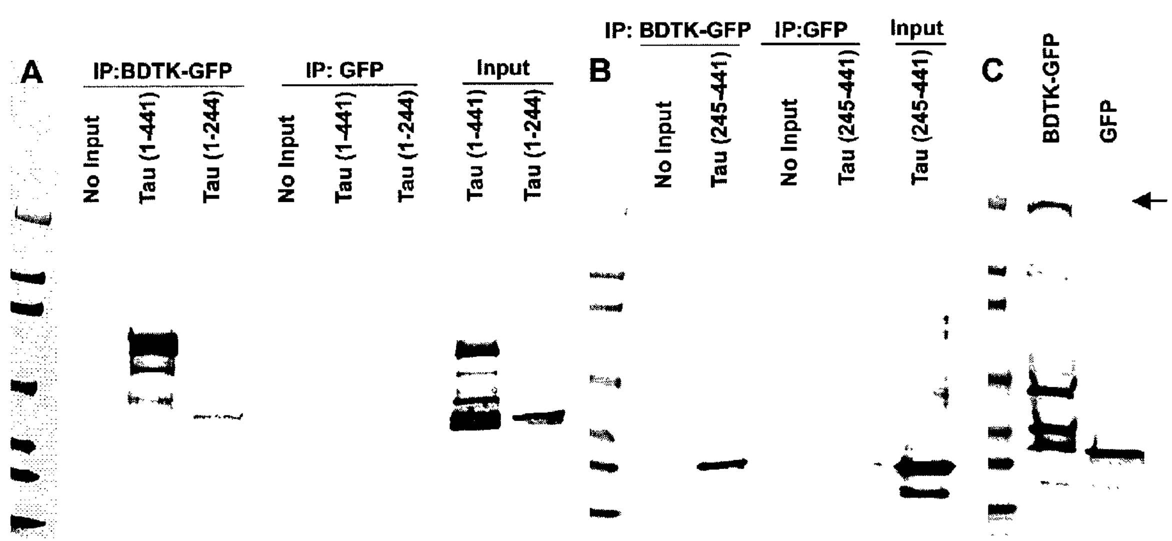
FIGS. 4A-4C are immunoblots showing that a BDTK-GFP fusion protein immunoprecipitated from stably transformed HEK293 cells interacts with Tau. Panel C is an immunoblot confirming the expression of recombinant proteins using anti-GFP polyclonal and monoclonal antibodies. BDTK(52-1261)-EGFP fusion protein was detected as an 180 kD protein (arrow indicates the full length protein) and GFP as a 30 kD protein. Panel A shows that BDTK(52-1261)-EGFP fusion protein can interact with full length tau (1-441) but only very weakly with the N-terminal tau mutant (1-244). Immunoprecipitated GFP does not bind to either tau mutants. Panel B shows that BDTK(52-1261)-EGFP fusion protein did bind to C-terminal tau (245-441) whereas again, GFP has no binding activity. This data demonstrates that BDTK binds to tau protein at its C-terminal region.

The binding and phosphorylation activity of BDTK and tau was analyzed as set forth above. To address if BDTK can interact with tau protein in vitro, recombinant BDTK(52-1261)-EGFP fusion protein or control GFP were generated. After immunoprecipitation of recombinant proteins from cells, the proteins were incubated with recombinant human tau proteins (1-441, 1-244, and 245-441). As shown in FIG. 4, Panel A, BDTK(52-1261)-EGFP fusion protein can interact with full length tau (1-441) but only very weakly with the N-terminal tau mutant (1-244). Immunoprecipitated GFP did not bind to either of the tau mutants. This data suggests that BDTK binds to tau protein at its C-terminal region. To further confirm the data, immunoprecipitated BDTK(52-1261)-EGFP fusion protein was incubated with tau(245-441). As shown in FIG. 4, Panel B, BDTK(52-1261)-EGFP fusion protein did bind to C-terminal tau (245-441) whereas GFP has no binding activity. This data demonstrates that BDTK binds to tau protein at its C-terminal region.

Figure 5:
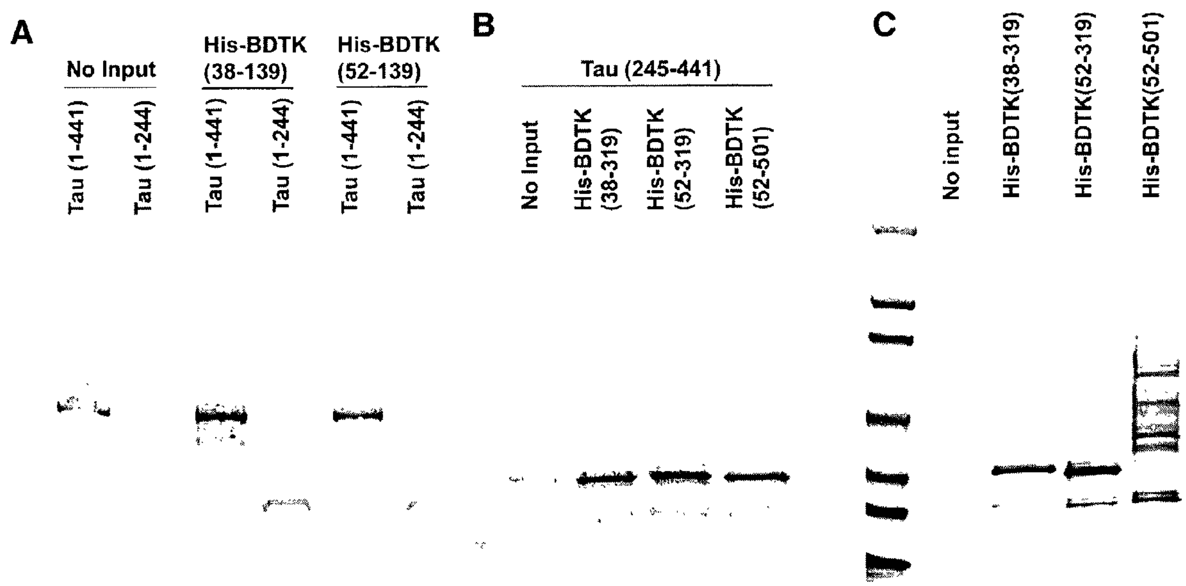
FIGS. 5A-5C are immunoblots showing that purified BDTK kinase domain, 38-319 (SEQ ID NO:4), and BDTK binding fragments 52-319 (SEQ ID NO:5), or 52-501 (SEQ ID NO:6) can bind to full length tau or C-terminal tau but not to N-terminal tau. Recombinant BDTK(38-319), BDTK(52-319), and BDTK(52-501) genes were constructed and the recombinant proteins were purified from *E. coli*. Each recombinant protein has a His-tag on its N-terminus, which enables the protein to bind to Ni-NTA resin. The expressed protein can be detected by anti-His antibody as shown in Panel C. BDTK(38-319), BDTK(52-319), and BDTK(52-501) were detected as 38 kD, 37 kD, and 70 kD, respectively. After binding of BDTK mutants to resin, tau mutants were applied to the resins and incubated with 2 μg of purified tau mutants (1-441, 1-244, and 245-441) in binding buffer (50 mM Tris-Cl, pH 7.4, 50 mM NaCl, 0.05% Tween-20, 0.3M sucrose, and 0.3% BSA) for 4 hr as consistent with the data with BDTK-EGFP fusion protein. As shown in Panel A, BDTK (38-319), BDTK(52-319), and BDTK(52-501) can bind to full length Tau but not N-terminal tau. As shown in Panel B, BDTK(38-319), BDTK(52-319), and BDTK(52-501) can bind to C-terminal tau (245-441) with similar binding activity. This data demonstrates that the binding domain of BDTK can bind to the C-terminal region of tau (245-441), in vitro. The binding affinity of full-length BDTK is higher than the binding fragment.
Figures 6A, 6B:
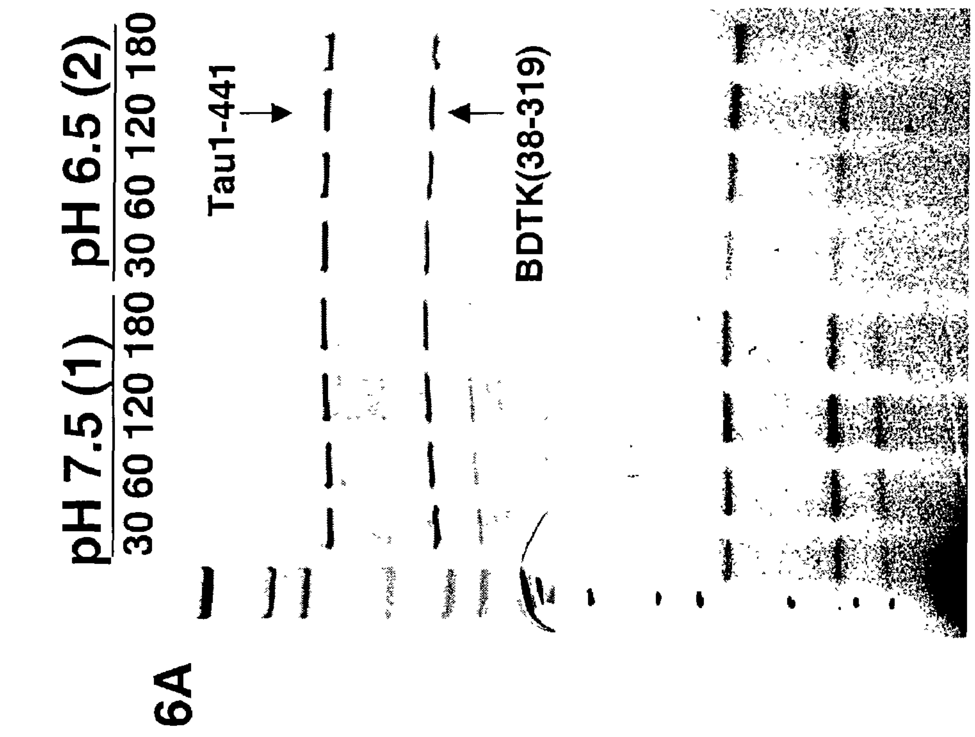
FIGS. 6A-6C show that tau protein and BDTK kinase domain are phosphorylated by BDTK, but not by BDTK binding fragment (52-319). BDTK (52-319) derived from published KIAA1855 gene failed to phosphorylate either tau or BDTK (6C). BDTK(38-319) did phosphorylate tau protein as well as BDTK itself (6B). BDTK autophosphorylation was saturated at 30 min at pH 7.5 (BDTK1 on graph) and at 60 min at pH 6.5 (BDTK2 on graph), whereas tau phosphorylation was saturated at 60 min at pH 7.5 (tau1 on graph) and 120 min at pH 6.5 (tau2 on graph) (6B). This data indicates that autophosphorylation of BDTK precedes tau phosphorylation, which may be important for its full activation. The kinetics of phosphorylation is faster at pH 7.5 than pH 6.5. This data indicates that BDTK is a tau kinase in neutral pH and that amino acids 38-51 are important for its kinase activity.
Figure 6C:
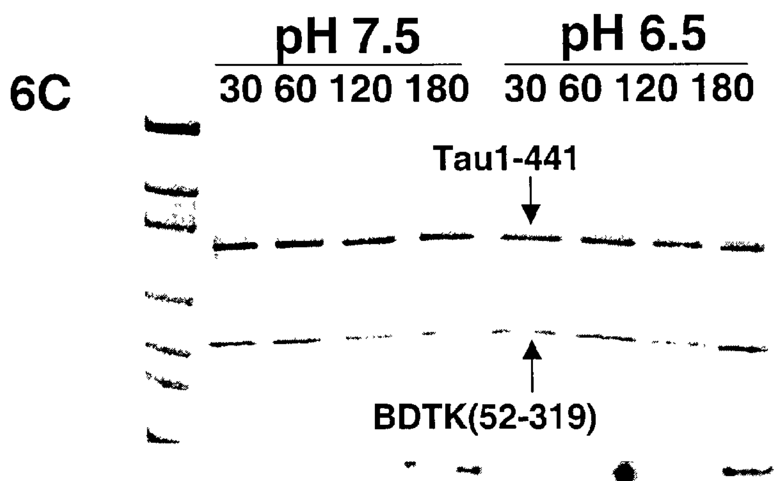
Figure 8:
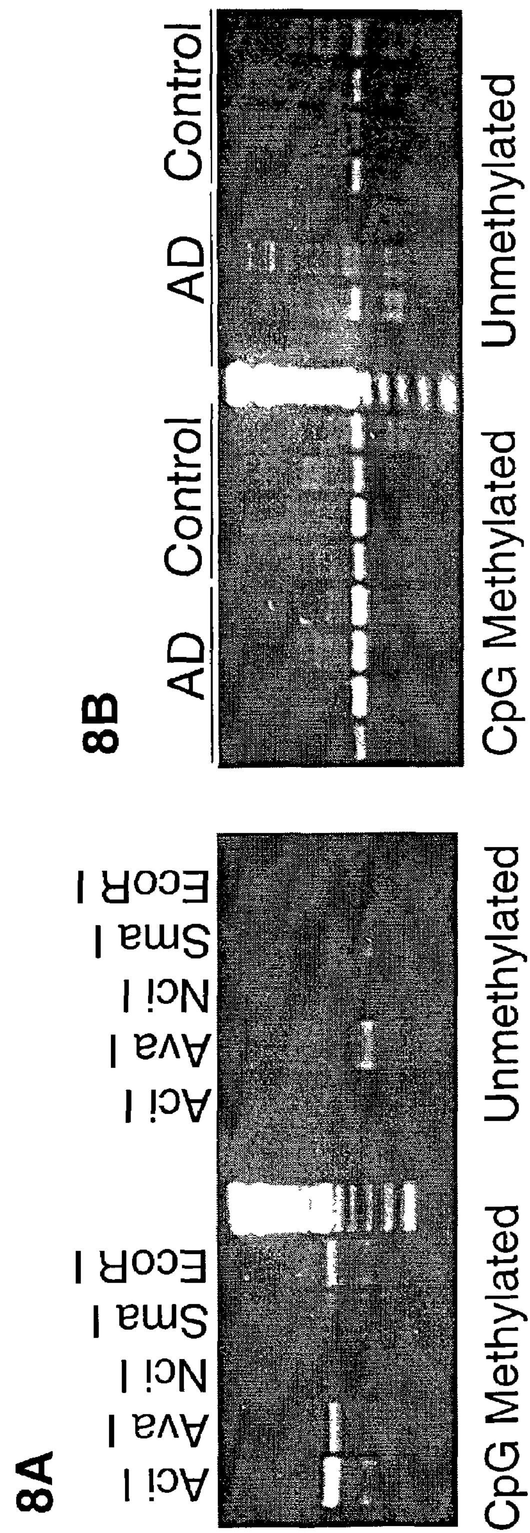
FIGS. 8A-8B depict polyacrylamide gels of the 5' genomic region of BDTK. Genomic DNA extracted from human cortex was methylated with CpG methylase (Sss I methylase) and S-adenosylmethionine (New England Biolabs) or left unmethylated, in vitro. After methylation, the CpG island genomic region located at the transcriptional initiation site was digested by methylation-sensitive restriction enzyme Aci I and Ava I. (8A) In vitro methylation of genomic DNA by CpG methylase protects the region from Aci I and Ava I digestion but not from Sma I digestion, which is methylation insensitive. (8B) Both AD and control brain samples are hypomethylated and sensitive to Ava I digestion (unmethylated group, right panel, 4 samples per group). CpG methylated genomic DNA shows PCR amplification (CpG methylated group, right panel). This data indicates that CpG island where BDTK gene transcription starts is hypomethylated and may serve as a promoter region.

Next, it was determined if the kinase domain of BDTK can bind to tau protein. Recombinant BDTK(38-319), BDTK(52-319), and BDTK(52-501) genes were constructed and the recombinant proteins were purified from *E. coli*. As shown in FIG. 5, panel A, both BDTK(38-319) and BDTK(52-319) can bind to full length tau protein (1-441) and very weakly with N-terminal tau (1-244), which is consistent with the data with BDTK-EGFP fusion protein. As shown in FIG. 5, Panel B, BDTK(38-319), BDTK(52-319), and BDTK(52-501) can bind to C-terminal tau (245-441) with similar binding activity. This data demonstrates that the kinase domain (52-319) of BDTK can bind to the C-terminal region of tau (245-441), in vitro.

Next, it was determined if the kinase domain of BDTK can phosphorylate tau as an interacting substrate, in vitro. According to the published tau kinases (Ttbk and GSK-3β) two different pH conditions were tested for the kinase activity of BDTK (pH 6.5 and 7.5). Using full length purified tau protein (1-441), the time course of phosphorylation kinetics was examined with BDTK(38-319) (SEQ ID NO:4) and BDTK(52-319) (SEQ ID NO:5) at 30, 60, 120, 180 minutes after incubation. BDTK(52-319), which is derived from the KIAA1855 sequence, failed to phosphorylate tau protein as well as BDTK itself (data not shown). However, BDTK(38-319), which contains the missing N-terminal sequence and two important glycine residues for structural assembly, did phosphorylate tau protein as well as BDTK itself. BDTK autophosphorylation was saturated at 30 min at pH 7.5 and at 60 min at pH 6.5, whereas tau phosphorylation was saturated at 60 min at pH 7.5 and 120 min at pH 6.5. This data indicates that autophosphorylation of BDTK precede tau phosphorylation, which may be important for its full activation. The kinetics of phosphorylation is faster at pH 7.5 than pH 6.5. This data indicates that BDTK is a tau kinase in neutral pH and amino acids 38-51 are important for its kinase activity.

Example III

Detection, Localization of BDTK and Corresponding Diagnostic Assays

Assays which measure BDTK mRNA or protein levels are conducted to assist in the diagnosis of Alzheimer's disease or other neurodegenerative tau related disorders. A sample may be isolated from a subject, and screening tests which measure levels of BDTK mRNA or protein are conducted in a normal versus a test patient, to aid in the diagnosis of Alzheimer's disease or other tau related disorders.

The BDTK polynucleotide was evaluated for it's expression in brains using mRNA in situ hybridization. In situ hybridization demonstrated that BDTK is expressed in the frontal cortex of human brains.

Although BDTK seems to be specifically expressed in brain tissues, it was not clear whether BDTK is expressed in neurons or other cell types, including glia, endothelial cells, or fibroblasts. To address this issue further, mRNA in situ hybridization was performed. Ten μm thickness brain slices were prepared from fresh frozen human brain cortex and were subjected to BDTK sense or antisense RNA probe hybridization. The data revealed that the BDTK antisense probe specifically stains neuronal cell bodies, which are co-registered with neuronal cell body marker NeuN. The sense probe showed no specific staining in the adjacent section (data not shown). This data indicates that BDTK is expressed in neurons.

BDTK may also be expressed in other body fluids, such as blood, serum, spinal fluid, saliva, urine, and other body tissues. Accordingly, these may be used to detect elevations in BDTK expression which correlate to Alzheimer's disease and other tau related disorders.

Example IV

Isolation of BDTK Promoter Region

A putative BDTK promoter region was determined and further studied. Exon 1 starts at a CpG island, which also contains a TATA box and transcription initiation site. CpG island is hypomethylated as demonstrated by methylation sensitive digestion and genomic PCR in both Alzheimer's disease and control brains, which suggest's it has promoter activity.

TABLE 2

The Isolated Upstream sequence, including Promoter Region of the BDTK Gene (SEQ ID NO:25)

```
gggggatgag ttgagaggaa ggcgatataa acatgtagag gatggagtgg ggaatcaggc

gagactgatg ggtcagatga ggaattttag acatgctagg agtggggaag ataaagggtg

atggagacag gtgagtttta tgggaacagg taaggagtga tggggctgtg ctgggagatg

gagtcaagcg ggtggcagag agctgtaagg agaacctgag agctggagcg ggacagccag

agagtcccag ggctggagga gageggagcg gggccgtcgg aacgtgatgt cagaggagga

gccgtgatgt cagagcgggc ggcgggcggt gatgtcaggg ctggtgctga tgctggcggc

gcggtgcatt gtgggcagct ccccgctctg ccgctgccgc cgccgtcgcc caaggaggat

cggggccggg ccgggccggg atgatccggg tcggaaggcc gccgccgccg gagggagcgg

gtcacccaac gccgcactga gccgccccg ccccgccccg gccccggggg atgcgccgcc

ccgagctgct gcctccgccg ccgccgcagc cgcagccgca gcgggcacag agcaggtgag

gcggggcggg gcgggccggg gtcggggcgg gggctccttc gtgggctcag ggggctccgc

ctggctcgcc tcccagcgca gccttcttgg gctcccctcc gcgctgctgt cgccgcccgc

tgggctggga cgctggccta caccgcctgg gccgcgccga ggcctggagc cg
```

As shown in the upper table, the BDTK gene transcription starts within CpG island (underlined sequence), which is followed by the first intron. It has been recently reported that some of the CpG islands function as transcriptional promoters and that its activity is regulated by CpG methylation. Since this region also contains a putative TATA box and transcriptional initiation signal, it is possible that this CpG island serves as BDTK promoter region.

To examine if the CpG island is transcriptionally active, we tested if it is hypomethylated using methylation-sensitive restriction enzyme and GC-rich PCR amplification system. Genomic DNA from human control and AD brains were extracted and treated with CpG methylated in vitro, or untreated. After methylation, DNA was digested by the methylation-sensitive restriction enzymes Aci I and Ava I. Hypomethylated CpG island will be digested and result in no PCR amplification of the target sequence, while the hypermethylated CpG island is protected from enzymatic digestion and detected by PCR amplification. Genomic DNA from control brain treated by CpG methylase can protect the region from Aci I and Ava I digestion but not by Sma I digestion, which is methylation insensitive. Both Alzheimer's Disease and control brain samples are hypomethylated and sensitive to Ava I digestion. CpG methylated genomic DNA shows PCR amplification. This data indicates that the CpG island where BDTK gene transcription starts is hypomethylated and may serve as a promoter region.

A luciferase assay was used to determine promoter activity. Briefly, to conduct this assay, the 1.2 kb and 0.6 kb promoter sequences (SEQ ID NO:8 and 8, respectively) were inserted into pGL3-control vector (Promega). At 48 hours, luciferase activity was measured using Dua1-luciferase kit (promega). Both the 0.6 kb and 1.2 kb promoter have significantly higher promoter activity compared to a control vector. This indicates that these regions have promoter activity.

Other reporter enzymes could be used to conduct similar assays, to determine promoter regions and measure promoter activity as exemplified above. Reporter enzymes are well known in the art and include, for example, chloramphenicol actylase transferase (CAT), green fluorescent protein (GFP), and the like.

Next, a luciferase/CPG methylation assay was conducted to determine if the promoters are regulated by CPG methylation. 1.2 kb and 0.6 kb promoter sequence were inserted into pGL3-control vector (Promega, named as CpG1.2 and CpG0.6, respectively). The luciferase constructs were methylated by CpG methylase (New Englash Biolabs) or untreated, and co-transfected with reference reporter gene (thymidine kinase promoter TK-RL plasmid, Promega) into PC12 using lipofection method (GenePorter, Gene Therapy Systems, Inc.). Both unmethylated 0.6 kb and 1.2 kb promoters has significantly higher promoter activity (3.56 and 12.6 fold increase, respectively) compared to control vector without DNA insert. However, both CpG methylated 0.6 and 1.2 kb promoters lose their transcriptional activity (99.88% and 99.95% inhibition compared to umethylated CpG promoter, respectively). This data demonstrated that the BDTK promoter activity is regulated by the methylation of its CpG island.

Example V

Drug Screening and Rational Drug Design

Assays are conducted which identify modulators of BDTK activity. BDTK modulators may include molecules which are agonists or antagonists of BDTK activity. BDTK modulators may include peptides, polynucleotides, small molecules, antibodies, receptors, and other molecules known in the art to modulate activity.

BDTK peptides may be used to inhibit BDTK activity. Two synthesis peptide (N21: KDRWKVVKKIGGGGFGEIYEA (SEQ ID NO:21) and AA21: KDRWKVWKKIAGAGFGEI-YEA (SEQ ID NO:22)) were synthesized to test if N21 and A21, where conserved two glycine residues are substituted with alanine, has inhibitory effect of BDTK kinase activity in vitro. Increasing amounts of peptides (0-1 mM) were tested for BDTK and tau phosphorylation, in vitro. As shown in FIG. 10, N21 peptide showed inhibitory effect from 100 )μM-1 mM up to 70% inhibition of BDTK phosphorylation (N21-BDTK). N21 peptide also partially inhibited tau phosphorylation from 300 μM to 1 μM (N21-tau). In contrast, AA21 mutated peptide rather increased both BDTK (AA21-BDTK, from 30 to 300 )μM) and tau phosphorylation (AA21-tau, from 30 μM to 1 μM) in dose response manner (See FIG. 10). These data suggest the potential use of N21 derivative as BDTK inhibitor, and the importance of two glycine residues for the inhibitory effect.

Additionally, known kinase inhibitors may be used to inhibit BDTK. Numerous kinase inhibitors were tested for their modulation effect on BDTK. As shown in FIG. 10, only rosovitine inhibited tau phosphorylation in dose-response manner.

In another embodiment, antisense molecules may be used to inhibit BDTK activity, for example those methods described previously.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated nucleic acid molecule comprising a sequence encoding a Brain Derived Tau Kinase (BDTK) protein, said BDTK protein having the amino acid sequence of SEQ ID NO: 2, wherein said nucleic acid molecule is a cDNA that encodes said BDTK protein.

2. An isolated nucleic acid molecule comprising a sequence encoding a Brain Derived Tau Kinase (BDTK) protein, said BDTK protein having the amino acid sequence of SEQ ID NO: 2, wherein said nucleic acid molecule is RNA.

3. A vector comprising the nucleic acid molecule of claim 1.

4. An isolated host cell comprising the vector of claim 3.

5. The nucleic acid molecule of claim 1, which comprises SEQ ID NO: 1.

6. An isolated nucleic acid molecule encoding a polypeptide, which is a fragment of SEQ ID NO:2, wherein the encoded polypeptide consists of the amino acid sequence of SEQ ID NO:3.

7. An isolated nucleic acid molecule comprising a sequence selected from the group consisting of:

a) SEQ ID NO: 1;

b) a sequence which is the complete complement of SEQ ID NO: 1; and c) a nucleic acid sequence encoding a polypeptide which is a fragment of a Brain Derived Tau Kinase (BDTK) protein of SEQ ID NO: 2, wherein the amino acid sequence of said polypeptide is amino acids 33-290 of SEQ ID NO: 2.

8. The nucleic acid molecule of claim 2, which is mRNA.

* * * * *

SEQUENCE LISTING

<160> NUMBER OF SEQ ID NOS: 25

<210> SEQ ID NO 1
<211> LENGTH: 7856
<212> TYPE: DNA
<213> ORGANISM: Homo Sapien

<400> SEQUENCE: 1
aaactgaaag agacaggcgg catgcagaat gtgttgttca aggaatgttg gaatgttgag 60
ttgttgagta acccaacatg tcagaagggg agtaatggcc taatgggtcc atgttgggaa 120
gatgttttga tgttacagta aagagtgtcc atcttatttg gtaagcagta aaaaccaatg 180
gcagagtttg tccacaaatg aaagaaaggg ccaaagaaag agagacacag attgagccaa 240
aagataaagc atataggtgg tgaggtgaga attgcacatg acgggtggtg ggtgcgagtg 300
tgggatggtc ccagaagtgg tgggtgatgg ggacgtatgg gaggatgggt acaggagagg 360
gggatgagtt gagaggaagg cgatataaac atgtagagga tggagtgggg aatcaggcga 420
gactgatggg tcagatgagg aattttagac atgctaggag tggggaagat aaagggtgat 480
ggagacaggt gagttttatg ggaacaggta aggagtgatg gggctgtgct gggagatgga 540
gtcaagcggg tggcagagag ctgtaaggag aacctgagag ctggagcggg acagccagag 600
agtcccaggg ctggaggaga gcggagcggg gccgtcggaa cgtgatgtca gaggaggagc 660
cgtgatgtca gagcgggcgg cgggcggtga tgtcagggct ggtgctgatg ctggcggcgc 720
ggtgcattgt gggcagctcc ccgctctgcc gctgccgccg ccgtcgccca aggaggatcg 780
gggccgggcc gggccgggat gatccgggtc ggaaggccgc cgccgccgga gggagcgggt 840
cacccaacgc cgcactgagc cgcccccgcc ccgccccggc cccgggggat gcgccgcccc 900
gagctgctgc ctccgccgcc gccgcagccg cagccgcagc gggcacagag caggtagatg 960 gcccccctcag ggcaggcccg gcggacaccc ctccctctgg ctggcggatg cagtgcctag 1020
cggccgccct taaggacgaa accaacatga gtgggggagg ggagcaggcc gacatcctgc 1080
cggccaacta cgtggtcaag gatcgctgga aggtggtgaa aaagatcggg ggcgggggct 1140
ttggtgagat ctacgaggcc atggacctgc tgaccaggga gaatgtggcc ctcaaggtgg 1200
agtcagccca gcagcccaag caggtcctca agatggaggt ggccgtgctc aagaagttgc 1260
aagggaagga ccatgtgtgc aggttcattg gctgtggcag gaacgagaag tttaactatg 1320
tagtgatgca gctccagggc cggaacctgg ccgacctgcg ccgtagccag ccgcgaggca 1380
ccttcacgct gagcaccaca ttgcggctgg gcaagcagat cttggagtcc atcgaggcca 1440

-continued

```
tccactctgt gggcttcctg caccgtgaca tcaagccttc aaactttgcc atgggcaggc   1500
tgccctccac ctacaggaag tgctatatgc tggacttcgg gctggcccgg cagtacacca   1560
acaccacggg ggatgtgcgg ccccctcgga atgtggccgg gtttcgagga acggttcgct   1620
atgcctcagt caatgcccac aagaaccggg agatgggccg ccacgacgac ctgtggtccc   1680
tcttctacat gctggtggag tttgcagtgg gccagctgcc ctggaggaag atcaaggaca   1740
aggaacaggt agggatgatc aaggagaagt atgagcaccg gatgctgctg aagcacatgc   1800
cgtcagagtt ccacctcttc ctggaccaca ttgccagcct cgactacttc accaagcccg   1860
actaccagtt gatcatgtca gtgtttgaga acagcatgaa ggagaggggc attgccgaga   1920
atgaggcctt tgactgggag aaggcaggca ccgatgccct cctgtccacg agcacctcta   1980
ccccgcccca gcagaacacc cggcagacgg cagccatgtt tggggtggtc aatgtgacgc   2040
cagtgcctgg ggacctgctc cgggagaaca ccgaggatgt gctacaggga gagcacctga   2100
gtgaccagga gaatgcaccc ccaattctgc ccgggaggcc ctctgagggg ctgggcccca   2160
gtccccacct tgtcccccac cccgggggtc ctgaggctga agtctgggag gagacagatg   2220
tcaaccggaa caaactccgg atcaacatcg gcaaaagccc ctgtgtggag gaggaacaga   2280
gccgaggcat gggggtcccc agctccccag tgcgtgcccc cccagactcc cccacaaccc   2340
cagtccgttc tctgcgctac cggagggtga acagccctga gtcagaaagg ctgtccacgg   2400
cggacgggcg agtggagcta cctgagagga ggtcacggat ggatctgcct ggctcgccct   2460
cgcgccaggc ctgctcctct cagccagccc agatgctgtc agtggacaca ggccacgctg   2520
accgacaggc cagtggccgc atggacgtgt cagcctctgt ggagcaggag gccctgagca   2580
acgccttccg ctcggtgccg ctggctgagg aggaggattt cgacagcaaa gagtgggtca   2640
tcatcgacaa ggagacggag ctcaaggact tccctccagg ggctgagccc agcacatcgg   2700
gcaccacgga tgaggagccc gaggagctgc ggccactgcc cgaggagggc gaagagcggc   2760
ggcggctggg ggcagagccc accgtccggc cccggggacg cagcatgcag gcgctggcgg   2820
aggaggacct gcagcatttg ccgccccagc ccctgccacc ccagctgagc cagggcgatg   2880
gccgttccga gacgtcacag ccccccacgc ctggcagccc ttcccactca cccctgcact   2940
cgggaccccg ccctcgacgg agagagtcgg accccacagg cccacagaga caggtgttct   3000
ccgtggcgcc cccatttgag gtgaatggcc tcccacgagc tgtgcctctg agtctgccct   3060
accaggactt caaaagagac ctctccgatt accgagaacg ggcgcggttg ctcaacaggg   3120
tccggagggt gggcttctcg cacatgctgc tcaccacccc ccaggtccca ctggctcctg   3180
ttcagcctca ggctaatggg aaggaggaag aggaggagga ggaggaagat gaggaagagg   3240
aagaagagga tgaggaagaa gaagaggagg aagaggaaga ggaggaggaa gaagaggagg   3300
aggaggaaga ggaggaggag gctgcagcgg cagttgcctt gggggaggtg ctggggcctc   3360
gtagtggctc cagcagtgag gggagtgaga ggagcactga ccggagccag gagggtgccc   3420
cgtccacgct gctggcagac gatcagaagg agtccagggg ccgggcctcc atggccgatg   3480
gggacctgga gcctgaggag ggctccaaaa cgctggtgct tgtctctcct ggcgacatga   3540
agaagtcgcc cgtcactgcc gaactggccc ccgaccccga cctgggcacc ctggctgccc   3600
tcactcctca gcatgagcgg ccccagccca cgggcagcca gctggacgta tctgagccag   3660
gcaccctgtc ctctgtcctc aagtctgagc ccaagccccc ggggcctggg gcagggctgg   3720
gggccgggac agtgaccaca ggggtcgggg gcgtggcagt cacctcctca cccttcacca   3780
aagttgagag gacctttgtg cacattgcgg agaaaaccca cctcaacgtc atgtcttccg   3840
```

-continued

```
gtggacaagc cttgcggtct gaggagttca gcgctggggg cgagctgggt ctggagctgg   3900
cctctgatgg gggcgctgtg gaggaggggg cccgagcgcc cctggagaac ggcctcgccc   3960
tgtcagggct gaatggggct gagatagagg gctctgccct gtctggggcc ccccgggaaa   4020
ccccctcaga gatggccaca aactcactgc ccaatggccc ggcccttgca gacgggccag   4080
ccccggtgtc ccgctggag ccaagccctg agaaagtggc caccatctcc cccagacgcc    4140
atgctatgcc aggctctcgc cccaggagcc gtatccctgt cctgctctct gaggaggaca   4200
cgggctcgga gccctcaggc tcactgtcgg ccaaagagcg gtggagcaag cgggctcggc   4260
cgcagcagga cctggcgcgg ctggtgatgg agaagaggca gggccgcctg ctgttgcggc   4320
tggcctcagg ggcctcgtcc tcctccagtg aggagcagcg ccgtgcctct gagaccctct   4380
caggcacggg ctctgaggag gacacgcccg cctctgagcc ggcagcggcc ttgcccagga   4440
agagcgggag ggcagccgcc accaggagcc ggattccccg ccccattggc ctccgcatgc   4500
ccatgcctgt tgcagcccag cagcccgcca gcagatccca tggcgcggcc ccagcattgg   4560
acacagccat caccagcagg ctccagctgc agacgccccc agggtcggcc actgctgctg   4620
acctccgccc caaacaacct cctggccgcg gcctgggccc agggcgagcc caagccggag   4680
ccaggccccc agcgccgcgc agcccgcgcc tccccgcgtc cacatccgcc gcgcgcaatg   4740
ccagcgcgtc cccccggagc cagtccctgt cccgcagaga gagcccctcc ccctcgcacc   4800
aggcccggcc cggggtcccc ccgccccggg gcgtcccgcc ggcccgggcc cagcctgatg   4860
gcaccccctc ccccgggggc tccaagaaag gacccagagg gaaactccag gctcagcgcg   4920
caacaaccaa aggccgggca ggaggcgcgg agggccgggc tggggccaga taatgacgcc   4980
cgctgctctc cgcggtcccc caccctcacc ccggcccccc acccgcagcc ggccacactg   5040
gagcagctcc cagcacagcc ttacgcgccc gacgcgcgcc acccgcggcc ccagctttcc   5100
gcctgcaccc gcgaggacgc gcgcgagcac acgcggcgcc ccgccaggcc ttagggcccg   5160
tgggggacgc ggccccgcgc cgcggggagg gtctgcctcc ccttcctcgc cctgtgtcct   5220
ctcatcctcc cgccgcccgt caggccggcc agcctcacat cagtctctcc gccccgggga   5280
aggctcagcc acttttcatc gaggactcca cttctgggga cgcctggttc gttcgcccac   5340
caggcctagg ctacgctcca tgctccccca gcaatctctg cctacacctc ctgcggcgcc   5400
ttgccctcct ccgacccctt tccagccaaa gtcccccac cccttcagag aagcagcctc    5460
aaattccaga agtggaggct ccagcctccc cgcgagggtc cagccccaca gtcttctggg   5520
agccattgtg gccagggacg gcctctggac tgccaggctg ggttggggac ccagggaaca   5580
tcggtctact caggtgtgag ggggcaggtc tgacctgccc caaagttggc tccatcctgg   5640
acaactcggt gagaggcagt gggcaagtga tcttggagat gggtgggcag gtgattctgt   5700
gggcagggga tgtgctcccc tgcacctctg gggtgcagaa acctcttgcc tccagatttg   5760
ggtggagcct ctgtgggaac cataggaagt gtgtgggctg ccttcctggg caagtatttc   5820
ccagtgggaa gttggagggg gctttaacaa agttttactc cctcccctgt tcccctgatc   5880
tagtgctcag gacccttcac catcaggaat tccttcctgt catctaacct cagtcctgcc   5940
tactgcagtt ccagccaacc tgctctttcc tgagttcaaa gcaggtggag actggctggt   6000
taccatcttt gcactggccc ttcggagatt cggggactca gttctggtgg ggtcaccctc   6060
cctgtcctcc cgcctgtggg agggagggag ggctggctca ggcatcgtct cccgcaatgg   6120
gcagagagag cagagacagg tggaccaaca gacagctggc ccctggaggc agaaaggccc   6180
```

-continued

```
ttctaacttc cagattgtat gcttgagtga tgggtcccca gcccaagccc actcttccct   6240

cagctcaccc ttcagcctgt tccttcttgc cctgacccca gcccgtgcag ctgctctact   6300

ccaggaatgg atgtggggac tcttcctggg ttctggctcc tgcatagctc accccacctc   6360

atcatgagcc tcaactgcct acatctgggg caagcagcac accggctgca gatgggacag   6420

ccagccctgc ctatctggac aggcccctgc agcctctgtc ccctggccta gcctctctgt   6480

ccttccctga gtcacagaga gcaagccaag acatccaggg aaagaggaag aaaggcctta   6540

gtgtgcccca gcagtctggc tgcgtccagc caccatcacc cggaaggatg cccacaaggc   6600

agctgaccct gaaagcagcc tccccctcat ggagagtcag cagcttgggc agccacttcc   6660

aggccagggt ggtggcttct ctgcagacca gctgagggga ggactcctgg gtggacagcc   6720

tttgacgtcc accccacgct gatgcagaag ctcccagaac actcaggaaa cttctccgga   6780

cagagccctc cttgtcaact tgaggccctc ccaaggccct ctactgccct ctgggtccag   6840

cagagggagt ggaggaaggg ccactgcctc ccacctagag cttctccgaa tgacaatcag   6900

ctcgtgccag gtggggacca ggatatgact cctggtgccc aggccctggg cctgctcctt   6960

gccaccaacc gaaccgtgaa tgtagggccc ccagcctcac ctctgcccca ggaccaacaa   7020

caccctggtt tggagctggg aggaagaagg gggcctgaga gagccccagg tccattctac   7080

ccccagcttc actcagcact ggagctggca gagacgcaaa acccagtctg cccttgggat   7140

tccaaacctc cctagggctc ccaactgacc tcaggcctct gagtcactga atgtcaccag   7200

gagaggtggg ggagggaaag tgggccagtg gggagggggt cacctagggg actgcctctg   7260

tgcctctccc caggaagcat ccagggcaga ggaagccaca tctcccggtg cccccaaccc   7320

cagctgcagc ctcctccccc tgagcattca ttctctccac caggcctcca ggtcctgagc   7380

ccttcctctg taaaagtgtc acaccacctc cctcagcact tccccatcac aacaacctat   7440

gtcactgact cagatgcagg gtctgctcac cccaacacat gccttccctc cccagccaca   7500

ccgtgcacga agggggcaca ggagaggaga ggggctgtgc cccaggctcc ccatttccca   7560

gctcctcaca gaggcctggt ttgctcagtc ttctgaactc cagggaccag ccctggtggg   7620

catggggtgg ggagcaggga gttgcccttc ccctccctcg ggaagccacc taagaatgtt   7680

tacatgccaa acagaatgta acacccctcc ccaagccctt cccagtcact gcatggcctc   7740

tgcccatcct gcacctgtcc accccacccc aacaccctgg aagccactgt caatgattag   7800

atcgggtctc ggaagggaag tagccatcac accattaaaa agcctgtgga cctttt       7856
```

<210> SEQ ID NO 2
<211> LENGTH: 1321
<212> TYPE: PRT
<213> ORGANISM: Homo Sapien

<400> SEQUENCE: 2

```
Met Gln Cys Leu Ala Ala Ala Leu Lys Asp Glu Thr Asn Met Ser Gly
1               5                   10                  15

Gly Gly Glu Gln Ala Asp Ile Leu Pro Ala Asn Tyr Val Val Lys Asp
            20                  25                  30

Arg Trp Lys Val Val Lys Lys Ile Gly Gly Gly Gly Phe Gly Glu Ile
        35                  40                  45

Tyr Glu Ala Met Asp Leu Leu Thr Arg Glu Asn Val Ala Leu Lys Val
    50                  55                  60

Glu Ser Ala Gln Gln Pro Lys Gln Val Leu Lys Met Glu Val Ala Val
65                  70                  75                  80
```

-continued

```
Leu Lys Lys Leu Gln Gly Lys Asp His Val Cys Arg Phe Ile Gly Cys
                85                  90                  95

Gly Arg Asn Glu Lys Phe Asn Tyr Val Val Met Gln Leu Gln Gly Arg
            100                 105                 110

Asn Leu Ala Asp Leu Arg Arg Ser Gln Pro Arg Gly Thr Phe Thr Leu
        115                 120                 125

Ser Thr Thr Leu Arg Leu Gly Lys Gln Ile Leu Glu Ser Ile Glu Ala
    130                 135                 140

Ile His Ser Val Gly Phe Leu His Arg Asp Ile Lys Pro Ser Asn Phe
145                 150                 155                 160

Ala Met Gly Arg Leu Pro Ser Thr Tyr Arg Lys Cys Tyr Met Leu Asp
                165                 170                 175

Phe Gly Leu Ala Arg Gln Tyr Thr Asn Thr Thr Gly Asp Val Arg Pro
            180                 185                 190

Pro Arg Asn Val Ala Gly Phe Arg Gly Thr Val Arg Tyr Ala Ser Val
        195                 200                 205

Asn Ala His Lys Asn Arg Glu Met Gly Arg His Asp Asp Leu Trp Ser
    210                 215                 220

Leu Phe Tyr Met Leu Val Glu Phe Ala Val Gly Gln Leu Pro Trp Arg
225                 230                 235                 240

Lys Ile Lys Asp Lys Glu Gln Val Gly Met Ile Lys Glu Lys Tyr Glu
                245                 250                 255

His Arg Met Leu Leu Lys His Met Pro Ser Glu Phe His Leu Phe Leu
            260                 265                 270

Asp His Ile Ala Ser Leu Asp Tyr Phe Thr Lys Pro Asp Tyr Gln Leu
        275                 280                 285

Ile Met Ser Val Phe Glu Asn Ser Met Lys Glu Arg Gly Ile Ala Glu
    290                 295                 300

Asn Glu Ala Phe Asp Trp Glu Lys Ala Gly Thr Asp Ala Leu Leu Ser
305                 310                 315                 320

Thr Ser Thr Ser Thr Pro Pro Gln Gln Asn Thr Arg Gln Thr Ala Ala
                325                 330                 335

Met Phe Gly Val Val Asn Val Thr Pro Val Pro Gly Asp Leu Leu Arg
            340                 345                 350

Glu Asn Thr Glu Asp Val Leu Gln Gly Glu His Leu Ser Asp Gln Glu
        355                 360                 365

Asn Ala Pro Pro Ile Leu Pro Gly Arg Pro Ser Glu Gly Leu Gly Pro
    370                 375                 380

Ser Pro His Leu Val Pro His Pro Gly Gly Pro Glu Ala Glu Val Trp
385                 390                 395                 400

Glu Glu Thr Asp Val Asn Arg Asn Lys Leu Arg Ile Asn Ile Gly Lys
                405                 410                 415

Ser Pro Cys Val Glu Glu Glu Gln Ser Arg Gly Met Gly Val Pro Ser
            420                 425                 430

Ser Pro Val Arg Ala Pro Pro Asp Ser Pro Thr Thr Pro Val Arg Ser
        435                 440                 445

Leu Arg Tyr Arg Arg Val Asn Ser Pro Glu Ser Glu Arg Leu Ser Thr
    450                 455                 460

Ala Asp Gly Arg Val Glu Leu Pro Glu Arg Arg Ser Arg Met Asp Leu
465                 470                 475                 480

Pro Gly Ser Pro Ser Arg Gln Ala Cys Ser Ser Gln Pro Ala Gln Met
                485                 490                 495

Leu Ser Val Asp Thr Gly His Ala Asp Arg Gln Ala Ser Gly Arg Met
```

-continued

```
            500                 505                 510

Asp Val Ser Ala Ser Val Glu Gln Glu Ala Leu Ser Asn Ala Phe Arg
        515                 520                 525

Ser Val Pro Leu Ala Glu Glu Glu Asp Phe Asp Ser Lys Glu Trp Val
    530                 535                 540

Ile Ile Asp Lys Glu Thr Glu Leu Lys Asp Phe Pro Pro Gly Ala Glu
545                 550                 555                 560

Pro Ser Thr Ser Gly Thr Thr Asp Glu Glu Pro Glu Glu Leu Arg Pro
                565                 570                 575

Leu Pro Glu Glu Gly Glu Glu Arg Arg Arg Leu Gly Ala Glu Pro Thr
            580                 585                 590

Val Arg Pro Arg Gly Arg Ser Met Gln Ala Leu Ala Glu Glu Asp Leu
        595                 600                 605

Gln His Leu Pro Pro Gln Pro Leu Pro Pro Gln Leu Ser Gln Gly Asp
    610                 615                 620

Gly Arg Ser Glu Thr Ser Gln Pro Pro Thr Pro Gly Ser Pro Ser His
625                 630                 635                 640

Ser Pro Leu His Ser Gly Pro Arg Pro Arg Arg Arg Glu Ser Asp Pro
                645                 650                 655

Thr Gly Pro Gln Arg Gln Val Phe Ser Val Ala Pro Pro Phe Glu Val
            660                 665                 670

Asn Gly Leu Pro Arg Ala Val Pro Leu Ser Leu Pro Tyr Gln Asp Phe
        675                 680                 685

Lys Arg Asp Leu Ser Asp Tyr Arg Glu Arg Ala Arg Leu Leu Asn Arg
    690                 695                 700

Val Arg Arg Val Gly Phe Ser His Met Leu Leu Thr Thr Pro Gln Val
705                 710                 715                 720

Pro Leu Ala Pro Val Gln Pro Gln Ala Asn Gly Lys Glu Glu Glu Glu
                725                 730                 735

Glu Glu Glu Glu Asp Glu Glu Glu Glu Glu Glu Asp Glu Glu Glu Glu
            740                 745                 750

Glu Glu Glu Glu Glu Glu Glu Glu Glu Glu Glu Glu Glu Glu Glu Glu
        755                 760                 765

Glu Glu Glu Ala Ala Ala Ala Val Ala Leu Gly Glu Val Leu Gly Pro
    770                 775                 780

Arg Ser Gly Ser Ser Ser Glu Gly Ser Glu Arg Ser Thr Asp Arg Ser
785                 790                 795                 800

Gln Glu Gly Ala Pro Ser Thr Leu Leu Ala Asp Asp Gln Lys Glu Ser
                805                 810                 815

Arg Gly Arg Ala Ser Met Ala Asp Gly Asp Leu Glu Pro Glu Glu Gly
            820                 825                 830

Ser Lys Thr Leu Val Leu Val Ser Pro Gly Asp Met Lys Lys Ser Pro
        835                 840                 845

Val Thr Ala Glu Leu Ala Pro Asp Pro Asp Leu Gly Thr Leu Ala Ala
    850                 855                 860

Leu Thr Pro Gln His Glu Arg Pro Gln Pro Thr Gly Ser Gln Leu Asp
865                 870                 875                 880

Val Ser Glu Pro Gly Thr Leu Ser Ser Val Leu Lys Ser Glu Pro Lys
                885                 890                 895

Pro Pro Gly Pro Gly Ala Gly Leu Gly Ala Gly Thr Val Thr Thr Gly
            900                 905                 910

Val Gly Gly Val Ala Val Thr Ser Ser Pro Phe Thr Lys Val Glu Arg
        915                 920                 925
```

-continued

```
Thr Phe Val His Ile Ala Glu Lys Thr His Leu Asn Val Met Ser Ser
    930                 935                 940

Gly Gly Gln Ala Leu Arg Ser Glu Glu Phe Ser Ala Gly Gly Glu Leu
945                 950                 955                 960

Gly Leu Glu Leu Ala Ser Asp Gly Gly Ala Val Glu Glu Gly Ala Arg
                965                 970                 975

Ala Pro Leu Glu Asn Gly Leu Ala Leu Ser Gly Leu Asn Gly Ala Glu
            980                 985                 990

Ile Glu Gly Ser Ala Leu Ser Gly Ala Pro Arg Glu Thr Pro Ser Glu
        995                 1000                1005

Met Ala Thr Asn Ser Leu Pro Asn Gly Pro Ala Leu Ala Asp Gly Pro
    1010                1015                1020

Ala Pro Val Ser Pro Leu Glu Pro Ser Pro Glu Lys Val Ala Thr Ile
1025                1030                1035                1040

Ser Pro Arg Arg His Ala Met Pro Gly Ser Arg Pro Arg Ser Arg Ile
                1045                1050                1055

Pro Val Leu Leu Ser Glu Glu Asp Thr Gly Ser Glu Pro Ser Gly Ser
            1060                1065                1070

Leu Ser Ala Lys Glu Arg Trp Ser Lys Arg Ala Arg Pro Gln Gln Asp
        1075                1080                1085

Leu Ala Arg Leu Val Met Glu Lys Arg Gln Gly Arg Leu Leu Leu Arg
    1090                1095                1100

Leu Ala Ser Gly Ala Ser Ser Ser Ser Ser Glu Glu Gln Arg Arg Ala
1105                1110                1115                1120

Ser Glu Thr Leu Ser Gly Thr Gly Ser Glu Glu Asp Thr Pro Ala Ser
                1125                1130                1135

Glu Pro Ala Ala Ala Leu Pro Arg Lys Ser Gly Arg Ala Ala Ala Thr
            1140                1145                1150

Arg Ser Arg Ile Pro Arg Pro Ile Gly Leu Arg Met Pro Met Pro Val
        1155                1160                1165

Ala Ala Gln Gln Pro Ala Ser Arg Ser His Gly Ala Ala Pro Ala Leu
    1170                1175                1180

Asp Thr Ala Ile Thr Ser Arg Leu Gln Leu Gln Thr Pro Pro Gly Ser
1185                1190                1195                1200

Ala Thr Ala Ala Asp Leu Arg Pro Lys Gln Pro Pro Gly Arg Gly Leu
                1205                1210                1215

Gly Pro Gly Arg Ala Gln Ala Gly Ala Arg Pro Pro Ala Pro Arg Ser
            1220                1225                1230

Pro Arg Leu Pro Ala Ser Thr Ser Ala Ala Arg Asn Ala Ser Ala Ser
        1235                1240                1245

Pro Arg Ser Gln Ser Leu Arg Arg Glu Ser Pro Ser Pro Ser His Gln
    1250                1255                1260

Ala Arg Pro Gly Val Pro Pro Pro Arg Gly Val Pro Pro Ala Arg Ala
1265                1270                1275                1280

Gln Pro Asp Gly Thr Pro Ser Pro Gly Gly Ser Lys Lys Gly Pro Arg
                1285                1290                1295

Gly Lys Leu Gln Ala Gln Arg Ala Thr Thr Lys Gly Arg Ala Gly Gly
            1300                1305                1310

Ala Glu Gly Arg Ala Gly Ala Arg Glx
        1315                1320
```

<210> SEQ ID NO 3
<211> LENGTH: 257

-continued

<212> TYPE: PRT
<213> ORGANISM: Homo Sapien

<400> SEQUENCE: 3

```
Trp Lys Val Val Lys Lys Ile Gly Gly Gly Gly Phe Gly Glu Ile Tyr
1               5                   10                  15

Glu Ala Met Asp Leu Leu Thr Arg Glu Asn Val Ala Leu Lys Val Glu
            20                  25                  30

Ser Ala Gln Gln Pro Lys Gln Val Leu Lys Met Glu Val Ala Val Leu
        35                  40                  45

Lys Lys Leu Gln Gly Lys Asp His Val Cys Arg Phe Ile Gly Cys Gly
    50                  55                  60

Arg Asn Glu Lys Phe Asn Tyr Val Val Met Gln Leu Gln Gly Arg Asn
65                  70                  75                  80

Leu Ala Asp Leu Arg Arg Ser Gln Pro Arg Gly Thr Phe Thr Leu Ser
                85                  90                  95

Thr Thr Leu Arg Leu Gly Lys Gln Ile Leu Glu Ser Ile Glu Ala Ile
            100                 105                 110

His Ser Val Gly Phe Leu His Arg Asp Ile Lys Pro Ser Asn Phe Ala
        115                 120                 125

Met Gly Arg Leu Pro Ser Thr Tyr Arg Lys Cys Tyr Met Leu Asp Phe
    130                 135                 140

Gly Leu Ala Arg Gln Tyr Thr Asn Thr Thr Gly Asp Val Arg Pro Pro
145                 150                 155                 160

Arg Asn Val Ala Gly Phe Arg Gly Thr Val Arg Tyr Ala Ser Val Asn
                165                 170                 175

Ala His Lys Asn Arg Glu Met Gly Arg His Asp Asp Leu Trp Ser Leu
            180                 185                 190

Phe Tyr Met Leu Val Glu Phe Ala Val Gly Gln Leu Pro Trp Arg Lys
        195                 200                 205

Ile Lys Asp Lys Glu Gln Val Gly Met Ile Lys Glu Lys Tyr Glu His
    210                 215                 220

Arg Met Leu Leu Lys His Met Pro Ser Glu Phe His Leu Phe Leu Asp
225                 230                 235                 240

His Ile Ala Ser Leu Asp Tyr Phe Thr Lys Pro Asp Tyr Gln Leu Ile
                245                 250                 255

Met
```

<210> SEQ ID NO 4
<211> LENGTH: 282
<212> TYPE: PRT
<213> ORGANISM: Homo Sapien

<400> SEQUENCE: 4

```
Lys Lys Ile Gly Gly Gly Gly Phe Gly Glu Ile Tyr Glu Ala Met Asp
1               5                   10                  15

Leu Leu Thr Arg Glu Asn Val Ala Leu Lys Val Glu Ser Ala Gln Gln
            20                  25                  30

Pro Lys Gln Val Leu Lys Met Glu Val Ala Val Leu Lys Lys Leu Gln
        35                  40                  45

Gly Lys Asp His Val Cys Arg Phe Ile Gly Cys Gly Arg Asn Glu Lys
    50                  55                  60

Phe Asn Tyr Val Val Met Gln Leu Gln Gly Arg Asn Leu Ala Asp Leu
65                  70                  75                  80

Arg Arg Ser Gln Pro Arg Gly Thr Phe Thr Leu Ser Thr Thr Leu Arg
```

```
                85                  90                  95

Leu Gly Lys Gln Ile Leu Glu Ser Ile Glu Ala Ile His Ser Val Gly
            100                 105                 110

Phe Leu His Arg Asp Ile Lys Pro Ser Asn Phe Ala Met Gly Arg Leu
        115                 120                 125

Pro Ser Thr Tyr Arg Lys Cys Tyr Met Leu Asp Phe Gly Leu Ala Arg
    130                 135                 140

Gln Tyr Thr Asn Thr Thr Gly Asp Val Arg Pro Pro Arg Asn Val Ala
145                 150                 155                 160

Gly Phe Arg Gly Thr Val Arg Tyr Ala Ser Val Asn Ala His Lys Asn
                165                 170                 175

Arg Glu Met Gly Arg His Asp Asp Leu Trp Ser Leu Phe Tyr Met Leu
            180                 185                 190

Val Glu Phe Ala Val Gly Gln Leu Pro Trp Arg Lys Ile Lys Asp Lys
        195                 200                 205

Glu Gln Val Gly Met Ile Lys Glu Lys Tyr Glu His Arg Met Leu Leu
    210                 215                 220

Lys His Met Pro Ser Glu Phe His Leu Phe Leu Asp His Ile Ala Ser
225                 230                 235                 240

Leu Asp Tyr Phe Thr Lys Pro Asp Tyr Gln Leu Ile Met Ser Val Phe
                245                 250                 255

Glu Asn Ser Met Lys Glu Arg Gly Ile Ala Glu Asn Glu Ala Phe Asp
            260                 265                 270

Trp Glu Lys Ala Gly Thr Asp Ala Leu Leu
        275                 280


<210> SEQ ID NO 5
<211> LENGTH: 268
<212> TYPE: PRT
<213> ORGANISM: Homo Sapien

<400> SEQUENCE: 5

Met Asp Leu Leu Thr Arg Glu Asn Val Ala Leu Lys Val Glu Ser Ala
1               5                   10                  15

Gln Gln Pro Lys Gln Val Leu Lys Met Glu Val Ala Val Leu Lys Lys
            20                  25                  30

Leu Gln Gly Lys Asp His Val Cys Arg Phe Ile Gly Cys Gly Arg Asn
        35                  40                  45

Glu Lys Phe Asn Tyr Val Val Met Gln Leu Gln Gly Arg Asn Leu Ala
    50                  55                  60

Asp Leu Arg Arg Ser Gln Pro Arg Gly Thr Phe Thr Leu Ser Thr Thr
65                  70                  75                  80

Leu Arg Leu Gly Lys Gln Ile Leu Glu Ser Ile Glu Ala Ile His Ser
                85                  90                  95

Val Gly Phe Leu His Arg Asp Ile Lys Pro Ser Asn Phe Ala Met Gly
            100                 105                 110

Arg Leu Pro Ser Thr Tyr Arg Lys Cys Tyr Met Leu Asp Phe Gly Leu
        115                 120                 125

Ala Arg Gln Tyr Thr Asn Thr Thr Gly Asp Val Arg Pro Pro Arg Asn
    130                 135                 140

Val Ala Gly Phe Arg Gly Thr Val Arg Tyr Ala Ser Val Asn Ala His
145                 150                 155                 160

Lys Asn Arg Glu Met Gly Arg His Asp Asp Leu Trp Ser Leu Phe Tyr
                165                 170                 175
```

-continued

```
Met Leu Val Glu Phe Ala Val Gly Gln Leu Pro Trp Arg Lys Ile Lys
            180                 185                 190

Asp Lys Glu Gln Val Gly Met Ile Lys Glu Lys Tyr Glu His Arg Met
        195                 200                 205

Leu Leu Lys His Met Pro Ser Glu Phe His Leu Phe Leu Asp His Ile
    210                 215                 220

Ala Ser Leu Asp Tyr Phe Thr Lys Pro Asp Tyr Gln Leu Ile Met Ser
225                 230                 235                 240

Val Phe Glu Asn Ser Met Lys Glu Arg Gly Ile Ala Glu Asn Glu Ala
                245                 250                 255

Phe Asp Trp Glu Lys Ala Gly Thr Asp Ala Leu Leu
            260                 265


<210> SEQ ID NO 6
<211> LENGTH: 450
<212> TYPE: PRT
<213> ORGANISM: Homo Sapien

<400> SEQUENCE: 6

Met Asp Leu Leu Thr Arg Glu Asn Val Ala Leu Lys Val Glu Ser Ala
1               5                   10                  15

Gln Gln Pro Lys Gln Val Leu Lys Met Glu Val Ala Val Leu Lys Lys
            20                  25                  30

Leu Gln Gly Lys Asp His Val Cys Arg Phe Ile Gly Cys Gly Arg Asn
        35                  40                  45

Glu Lys Phe Asn Tyr Val Val Met Gln Leu Gln Gly Arg Asn Leu Ala
    50                  55                  60

Asp Leu Arg Arg Ser Gln Pro Arg Gly Thr Phe Thr Leu Ser Thr Thr
65                  70                  75                  80

Leu Arg Leu Gly Lys Gln Ile Leu Glu Ser Ile Glu Ala Ile His Ser
                85                  90                  95

Val Gly Phe Leu His Arg Asp Ile Lys Pro Ser Asn Phe Ala Met Gly
            100                 105                 110

Arg Leu Pro Ser Thr Tyr Arg Lys Cys Tyr Met Leu Asp Phe Gly Leu
        115                 120                 125

Ala Arg Gln Tyr Thr Asn Thr Thr Gly Asp Val Arg Pro Pro Arg Asn
    130                 135                 140

Val Ala Gly Phe Arg Gly Thr Val Arg Tyr Ala Ser Val Asn Ala His
145                 150                 155                 160

Lys Asn Arg Glu Met Gly Arg His Asp Asp Leu Trp Ser Leu Phe Tyr
                165                 170                 175

Met Leu Val Glu Phe Ala Val Gly Gln Leu Pro Trp Arg Lys Ile Lys
            180                 185                 190

Asp Lys Glu Gln Val Gly Met Ile Lys Glu Lys Tyr Glu His Arg Met
        195                 200                 205

Leu Leu Lys His Met Pro Ser Glu Phe His Leu Phe Leu Asp His Ile
    210                 215                 220

Ala Ser Leu Asp Tyr Phe Thr Lys Pro Asp Tyr Gln Leu Ile Met Ser
225                 230                 235                 240

Val Phe Glu Asn Ser Met Lys Glu Arg Gly Ile Ala Glu Asn Glu Ala
                245                 250                 255

Phe Asp Trp Glu Lys Ala Gly Thr Asp Ala Leu Leu Ser Thr Ser Thr
            260                 265                 270

Ser Thr Pro Pro Gln Gln Asn Thr Arg Gln Thr Ala Ala Met Phe Gly
        275                 280                 285
```

-continued

```
Val Val Asn Val Thr Pro Val Pro Gly Asp Leu Leu Arg Glu Asn Thr
    290                 295                 300

Glu Asp Val Leu Gln Gly Glu His Leu Ser Asp Gln Glu Asn Ala Pro
305                 310                 315                 320

Pro Ile Leu Pro Gly Arg Pro Ser Glu Gly Leu Gly Pro Ser Pro His
                325                 330                 335

Leu Val Pro His Pro Gly Gly Pro Glu Ala Glu Val Trp Glu Glu Thr
            340                 345                 350

Asp Val Asn Arg Asn Lys Leu Arg Ile Asn Ile Gly Lys Ser Pro Cys
        355                 360                 365

Val Glu Glu Glu Gln Ser Arg Gly Met Gly Val Pro Ser Ser Pro Val
    370                 375                 380

Arg Ala Pro Pro Asp Ser Pro Thr Thr Pro Val Arg Ser Leu Arg Tyr
385                 390                 395                 400

Arg Arg Val Asn Ser Pro Glu Ser Glu Arg Leu Ser Thr Ala Asp Gly
                405                 410                 415

Arg Val Glu Leu Pro Glu Arg Arg Ser Arg Met Asp Leu Pro Gly Ser
            420                 425                 430

Pro Ser Arg Gln Ala Cys Ser Ser Gln Pro Ala Gln Met Leu Ser Val
        435                 440                 445

Asp Thr
    450
```

```
<210> SEQ ID NO 7
<211> LENGTH: 1198
<212> TYPE: DNA
<213> ORGANISM: Homo Sapien

<400> SEQUENCE: 7

aaactgaaag agacaggcgg catgcagaat gtgttgttca aggaatgttg gaatgttgag     60

ttgttgagta acccaacatg tcagaagggg agtaatggcc taatgggtcc atgttgggaa    120

gatgttttga tgttacagta aagagtgtcc atcttatttg gtaagcagta aaaaccaatg    180

gcagagtttg tccacaaatg aaagaaaggg ccaaagaaag agagacacag attgagccaa    240

aagataaagc atataggtgg tgaggtgaga attgcacatg acgggtggtg ggtgcgagtg    300

tgggatggtc ccagaagtgg tgggtgatgg ggacgtatgg gaggatgggt acaggagagg    360

gggatgagtt gagaggaagg cgatataaac atgtagagga tggagtgggg aatcaggcga    420

gactgatggg tcagatgagg aattttagac atgctaggag tggggaagat aaagggtgat    480

ggagacaggt gagttttatg ggaacaggta aggagtgatg gggctgtgct gggagatgga    540

gtcaagcggg tggcagagag ctgtaaggag aacctgagag ctggagcggg acagccagag    600

agtcccaggg ctggaggaga gcggagcggg gccgtcggaa cgtgatgtca gaggaggagc    660

cgtgatgtca gagcgggcgg cgggcggtga tgtcagggct ggtgctgatg ctggcggcgc    720

ggtgcattgt gggcagctcc ccgctctgcc gctgccgccg ccgtcgccca aggaggatcg    780

gggccgggcc gggccgggat gatccgggtc ggaaggccgc cgccgccgga gggagcgggt    840

cacccaacgc cgcactgagc cgcccccgcc ccgccccggc cccgggggat gcgccgcccc    900

gagctgctgc ctccgccgcc gccgcagccg cagccgcagc gggcacagag caggtgaggc    960

ggggcggggc gggccggggt cggggcgggg gctccttcgt gggctcaggg ggctccgcct   1020

ggctcgcctc ccagcgcagc cttcttgggc tcccctccgc gctgctgtcg ccgccccgctg   1080

ggctgggacg ctggcctaca ccgcctgggc cgcgccgagg cctggagccg ctccctgtcc   1140
```

ccagcacaca gacctccctc cccaacccgt cctccgggca ctttgctcct ccccactc 1198

<210> SEQ ID NO 8
<211> LENGTH: 551
<212> TYPE: DNA
<213> ORGANISM: Homo Sapien

<400> SEQUENCE: 8
tcagaggagg agccgtgatg tcagagcggg cggcgggcgg tgatgtcagg gctggtgctg 60
atgctggcgg cgcggtgcat tgtgggcagc tccccgctct gccgctgccg ccgccgtcgc 120
ccaaggagga tcggggccgg gccgggccgg gatgatccgg gtcggaaggc cgccgccgcc 180
ggagggagcg ggtcacccaa cgccgcactg agccgccccc gccccgcccc ggccccgggg 240
gatgcgccgc cccgagctgc tgcctccgcc gccgccgcag ccgcagccgc agcgggcaca 300
gagcaggtga ggcggggcgg ggcgggccgg ggtcggggcg ggggctcctt cgtgggctca 360
gggggctccg cctggctcgc ctcccagcgc agccttcttg ggctcccctc cgcgctgctg 420
tcgccgcccg ctgggctggg acgctggcct acaccgcctg ggccgcgccg aggcctggag 480
ccgctccctg tccccagcac acagacctcc ctccccaacc cgtcctccgg gcactttgct 540
cctccccact c 551

<210> SEQ ID NO 9
<211> LENGTH: 44
<212> TYPE: DNA
<213> ORGANISM: Artificial Sequence
<220> FEATURE:
<223> OTHER INFORMATION: oligo

<400> SEQUENCE: 9
cgacuggagc acgaggacac ugacauggac ugaaggagua gaaa 44

<210> SEQ ID NO 10
<211> LENGTH: 28
<212> TYPE: DNA
<213> ORGANISM: Homo Sapien
<220> FEATURE:
<223> OTHER INFORMATION: primer

<400> SEQUENCE: 10
tggcctcgat ggactccaag atctgctt 28

<210> SEQ ID NO 11
<211> LENGTH: 23
<212> TYPE: DNA
<213> ORGANISM: Homo Sapien
<220> FEATURE:
<223> OTHER INFORMATION: primer

<400> SEQUENCE: 11
cgactggagc acgaggacac tga 23

<210> SEQ ID NO 12
<211> LENGTH: 26
<212> TYPE: DNA
<213> ORGANISM: Homo Sapien
<220> FEATURE:
<223> OTHER INFORMATION: primer

<400> SEQUENCE: 12
ggacactgac atggactgaa ggagta 26

<210> SEQ ID NO 13
<211> LENGTH: 24
<212> TYPE: DNA
<213> ORGANISM: Homo Sapien
<220> FEATURE:
<223> OTHER INFORMATION: primer

<400> SEQUENCE: 13
caagatctgc ttgcccagcc gcaa 24

<210> SEQ ID NO 14
<211> LENGTH: 30
<212> TYPE: DNA
<213> ORGANISM: Homo Sapien
<220> FEATURE:
<223> OTHER INFORMATION: primer

<400> SEQUENCE: 14
ggaattccat atggacctgc tgaccaggga 30

<210> SEQ ID NO 15
<211> LENGTH: 27
<212> TYPE: DNA
<213> ORGANISM: Homo Sapien
<220> FEATURE:
<223> OTHER INFORMATION: primer

<400> SEQUENCE: 15
aaggatccca ggagggcatc ggtgcct 27

<210> SEQ ID NO 16
<211> LENGTH: 21
<212> TYPE: DNA
<213> ORGANISM: Homo Sapien
<220> FEATURE:
<223> OTHER INFORMATION: primer

<400> SEQUENCE: 16
gaagtccttg agctccgtct c 21

<210> SEQ ID NO 17
<211> LENGTH: 48
<212> TYPE: DNA
<213> ORGANISM: Homo Sapien
<220> FEATURE:
<223> OTHER INFORMATION: Oligo

<400> SEQUENCE: 17
tattcttaag aagatcgggg gcgggggctt tggtgaaatc tacgaggc 48

<210> SEQ ID NO 18
<211> LENGTH: 48
<212> TYPE: DNA
<213> ORGANISM: Homo Sapien
<220> FEATURE:
<223> OTHER INFORMATION: oligo

<400> SEQUENCE: 18
tagcctcgta gatttcacca aagcccccgc ccccgatctt cttaagaa 48

<210> SEQ ID NO 19
<211> LENGTH: 20
<212> TYPE: DNA
<213> ORGANISM: Homo Sapien
<220> FEATURE:
<223> OTHER INFORMATION: primer

<400> SEQUENCE: 19
tcagaggagg agccgtgatg 20

<210> SEQ ID NO 20
<211> LENGTH: 19
<212> TYPE: DNA
<213> ORGANISM: Homo Sapien
<220> FEATURE:
<223> OTHER INFORMATION: primer

<400> SEQUENCE: 20
agtggggagg agcaaagtg 19

<210> SEQ ID NO 21
<211> LENGTH: 21
<212> TYPE: PRT
<213> ORGANISM: Artificial Sequence
<220> FEATURE:
<223> OTHER INFORMATION: synthetic peptide

<400> SEQUENCE: 21

Lys Asp Arg Trp Lys Val Val Lys Lys Ile Gly Gly Gly Gly Phe Gly
1 5 10 15

Glu Ile Tyr Glu Ala
20

<210> SEQ ID NO 22
<211> LENGTH: 21
<212> TYPE: PRT
<213> ORGANISM: Artificial Sequence
<220> FEATURE:
<223> OTHER INFORMATION: synthetic peptide

<400> SEQUENCE: 22

Lys Asp Arg Trp Lys Val Trp Lys Lys Ile Ala Gly Ala Gly Phe Gly
1 5 10 15

Glu Ile Tyr Glu Ala
20

<210> SEQ ID NO 23
<211> LENGTH: 235
<212> TYPE: DNA
<213> ORGANISM: Homo Sapien

<400> SEQUENCE: 23
cagccgcagc cgcagcgggc acagagcagg tagatggccc cctcagggca ggcccggcgg 60
acacccctcc ctctggctgg cggatgcagt gcctagcggc cgcccttaag gacgaaacca 120
acatgagtgg gggaggggag caggccgaca tcctgccggc caactacgtg gtcaaggatc 180
gctggaaggt ggtgaaaaag atcgggggcg ggggctttgg tgagatctac gaggc 235

<210> SEQ ID NO 24
<211> LENGTH: 51
<212> TYPE: PRT
<213> ORGANISM: Homo Sapien

<400> SEQUENCE: 24

Met Gln Cys Leu Ala Ala Ala Leu Lys Asp Glu Thr Asn Met Ser Gly
1 5 10 15

Gly Gly Glu Gln Ala Asp Ile Leu Pro Ala Asn Tyr Val Val Lys Asp
20 25 30

-continued

```
Arg Trp Lys Val Val Lys Lys Ile Gly Gly Gly Gly Phe Gly Glu Ile
        35                  40                  45

Tyr Glu Ala
    50


<210> SEQ ID NO 25
<211> LENGTH: 772
<212> TYPE: DNA
<213> ORGANISM: Homo Sapien

<400> SEQUENCE: 25

gggggatgag ttgagaggaa ggcgatataa acatgtagag gatggagtgg ggaatcaggc      60

gagactgatg ggtcagatga ggaattttag acatgctagg agtggggaag ataaagggtg     120

atggagacag gtgagtttta tgggaacagg taaggagtga tggggctgtg ctgggagatg     180

gagtcaagcg ggtggcagag agctgtaagg agaacctgag agctggagcg ggacagccag     240

agagtcccag ggctggagga gagcggagcg gggccgtcgg aacgtgatgt cagaggagga     300

gccgtgatgt cagagcgggc ggcgggcggt gatgtcaggg ctggtgctga tgctggcggc     360

gcggtgcatt gtgggcagct ccccgctctg ccgctgccgc cgccgtcgcc caaggaggat     420

cggggccggg ccgggccggg atgatccggg tcggaaggcc gccgccgccg gagggagcgg     480

gtcacccaac gccgcactga gccgcccccg ccccgccccg gccccggggg atgcgccgcc     540

ccgagctgct gcctccgccg ccgccgcagc cgcagccgca gcgggcacag agcaggtgag     600

gcggggcggg gcgggccggg gtcggggcgg gggctccttc gtgggctcag gggctccgc      660

ctggctcgcc tcccagcgca gccttcttgg gctcccctcc gcgctgctgt cgccgcccgc     720

tgggctggga cgctggccta caccgcctgg gccgcgccga ggcctggagc cg             772
```